US007935801B2

(12) United States Patent
Campbell et al.

(10) Patent No.: US 7,935,801 B2
(45) Date of Patent: *May 3, 2011

(54) TEAL FLUORESCENT PROTEINS

(75) Inventors: Robert Earl Campbell, Edmonton (CA); Hu-Wang Ai, Edmonton (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 460 days.

This patent is subject to a terminal disclaimer.

(21) Appl. No.: 11/948,524

(22) Filed: Nov. 30, 2007

(65) Prior Publication Data

US 2009/0170194 A1    Jul. 2, 2009

Related U.S. Application Data

(63) Continuation-in-part of application No. 11/419,437, filed on May 19, 2006, now Pat. No. 7,790,868.

(51) Int. Cl.
   *C07H 21/04*   (2006.01)
   *C12N 15/63*   (2006.01)
   *C12N 15/85*   (2006.01)
   *C12N 15/86*   (2006.01)
   *C12N 1/20*    (2006.01)
   *C12N 1/21*    (2006.01)
   *C12N 1/15*    (2006.01)
   *C12N 5/14*    (2006.01)
   *C12N 1/19*    (2006.01)

(52) U.S. Cl. .................... 536/23.1; 435/320.1; 435/325; 435/252.1; 435/252.3; 435/254.11; 435/419; 435/254.2

(58) Field of Classification Search .................. None
See application file for complete search history.

(56) References Cited

U.S. PATENT DOCUMENTS

| | | | |
|---|---|---|---|
| 6,020,192 A | 2/2000 | Muzyczka et al. | |
| 6,969,597 B2 | 11/2005 | Lukyanov et al. | |
| 2003/0059835 A1 | 3/2003 | Tsien et al. | |
| 2006/0275827 A1* | 12/2006 | Campbell et al. | 435/7.1 |

FOREIGN PATENT DOCUMENTS

WO            01/27150          4/2001

OTHER PUBLICATIONS

Branden et al., "Introduction to Protein Structure Second Edition", Garland Publishing Inc., New York, 1999.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
James, Douglas R., et al. "Stoboscopic Optical Boxcar Technique for the Determination of Fluorescence Lifetimes", Review of Scientific Instruments 63, pp. 1710-1716 (1992).
Matz, Mikhail V. et al. "Fluorescent Proteins from Nonbioluminescent Anthozoa Species", Nat. Biotechnol 17, pp. 969-973 (1999).
Miyawaki, A., et al. "Fluorescent Indicators for Ca2+ based on green fluorescent proteins and calmodulin", Nature 388, pp. 882-887 (1997).
Nguyen, Annalee W., et al., "Evolutionary Optimization of Fluorescent Proteins for Intracellular FRET", Nat. Biotechnol 23, pp. 355-360 (2005).
Ormo, Mats, et al. "Crystal Structure of the Aequorea Victoria Green Fluorescent Protein", Science 273, pp. 1392-1395 (1996).
Shimomura, O. "Structure of the Chromophore of Aequorea Green Fluorescent Protein", Febs. Letters 104, pp. 220-222 (1979).
Sun, Yi, et al. "Biophysical Characterization of Natural and Mutant Fluorescent Proteins Cloned from Zooxanthellate Corals", FEBS Lett., 570:175-83, (2004).
Tsien, Roger Y.; "The Green Fluorescent Protein", Annual Rev. Biochem. 67:509-44 (1998).
Ward, William W., "Biochemical and Physical Properties of Green Fluorescent Protein", Properties, Applications and Protocols (ed. M.K. Chalfie, S.) 45-75 (Wiley, New York; 1998).
Yang, Fan, et al. "The Molecular Structure of Green Fluorescent Protein", Nat. Biotechnol 14, pp. 1246-1251 (1996).
Brannon, James H., et al. "Absolute Quantum Yield Determination by Thermal Blooming", Journal of Physical Chem. 82, pp. 705-709 (1978).
Formant, Michel, et al. "Direct Random Mutagenesis of Gene-Sized DNA Fragments Using Polymerase Chain Reaction", Anal. Biochem. 224, pp. 347-353 (1995).
Heim, Roger, et al. "Wavelength Mutations and Posttranslations autooxidation of green fluorescent protein", Proc. Nat. Acad. Sci. USA, 91: pp. 12501-12504 (1994).
Heim, Roger, et al. "Improved Green Fluorescence", Nature vol. 373, pp. 663-664 (1995).
Karasawa, S., et al. "Cyan-Emitting and Orange-Emitting Fluorescent Proteins as a donor/acceptor pair for fluorescence resonance energy transfer", Biochem. Journal, 381:307-12, (2004).
Karasawa, S., et al.; "A Green-emitting Fluorescent Protein from Galaxeidae Coral and its Monomeric Version for Use in Fluorescent Labelling", J. of Biochem. 278:34167-171, (2003).

(Continued)

*Primary Examiner* — Suzanne M Noakes
*Assistant Examiner* — Jae W Lee
(74) *Attorney, Agent, or Firm* — Bennett Jones LLP

(57) ABSTRACT

An isolated nucleic acid sequence encoding a non-oligomerizing *Clavularia* teal fluorescent protein (TFP) variant having a tyrosine-derived chromophore, and fragments and derivatives thereof. Also provided is a method for engineering the nucleic acid sequence, a vector comprising the nucleic acid sequence, a host cell comprising the vector, and use of the vector in a method for expressing the nucleic acid sequence. The present invention further provides an isolated nucleic acid, or mimetic or complement thereof, that hybridizes under stringent conditions to the nucleic acid sequence. Additionally, the present invention provides a non-oligomerizing TFP variant encoded by the nucleic acid sequence, as well as derivatives, fragments, and homologues thereof. Also provided is an antibody that specifically binds to the TFP variant. The present invention further provides a tandem dimer comprising two TFP dimers, operatively linked by a peptide linker.

13 Claims, 40 Drawing Sheets

OTHER PUBLICATIONS

Lukyanov, K.A., et al. "Photoactivatable Fluorescent Proteins", Nature Reviews/Molecular Cell Biology, vol. 6, pp. 885-891 (2005).
Rizzo, Mark A., et al. "An Improved Cyan Fluorescent Protein Variant Useful for FRET", Nat. Biotechnol 22, pp. 445-449 (2004).
Rizzo, Mark. A., et al. "High-Contrast Imaging of Fluorescent Protetin FRET by Fluorescence Polarization Microscopy", Biophys. J. 88, pp. L14-16 (2005).
Shaner, Nathan C., et al. "Improved Monomeric Red, Orange and Yellow Fluorescent Proteins Derived from Discosomas sp. Red Fluorescent Protein", Nat. Biotech 22: pp. 1567-1572, (2004).
Shaner, Nathan C., et al. "A guide to choosing fluorescent proteins", Nat. Methods 2, pp. 905-909 (2005).
Yarbrough, D., et al. "Refined Crystal Structure of DsRed, a red fluorescent protein from coral, at 2.0-A Resolution", Proc. Natl. Acad. Sci. USA, 98:462-67 (2001).
Bevis, Brooke, et al. (Rapidly Maturing Variants of Discosoma Red Fluorescent Protein (DsRed); Nat. Biotech. 20, pp. 83-87 (2002).
Campbell, Robert E., et al. "A Monomeric Red Fluorescent Protein", Proc. Natl. Acad. Sci USA, 99, pp. 7877-7882 (2002).
Griesbeck, Oliver, et al. "Reducing the Environmental Sensitivity of Yellow Fluorescent Protein", J. Biol. Chem. 276, pp. 29188-29194 (2001).
Heim, Roger et al. "Engineering Green Fluorescent Protein for Improved Brightness, Longer Wavelengths and Fluorescence Resonance Energy Transfer", Curr. Biol. 6, pp. 178-182, (1996).
Zacharias, David A. et al. "Partitoning of Lipid-Modified Monomeric GFPs into Membrane Microdominas of Live Cells", Science 296,pp. 913-916 (2002).
Zhang, J. et al. "Creating new Fluorescent Probes for Cell Biology", Nat. Rev. Mol. Cell Biol., 3:906-18 (2002).
Ngo, et al."Computational Complexity; Protein Structure Prediction, and Levinthal Paradox", pp. 433 and 492-495, 1994 Mertz et al. (ed) Birkhauser, Boston.

* cited by examiner

FIG. 3A

|  |  |  |  |  |  |  |  |  |  |  |  |  |  |  |  |
|---|---|---|---|---|---|---|---|---|---|---|---|---|---|---|---|
| Library | - | - | - | - | - | - | - | - | - | - | - | - | - | - | - |
| mTFP1 |  |  |  |  |  |  |  |  |  |  |  |  |  |  |  |
| cFP484 | M | K | C | K | F | V | F | C | L | S | F | L | V | L | A | I |
| dsFP483 | - | - | - | - | - | - | - | - | - | - | - | - | - | - | - |
| amFP486 | - | - | - | - | - | - | - | - | - | - | - | - | - | - | - |
| mCherry | - | - | - | - | - | - | - | - | - | - | - | - | - | - | - |
| EGFP | - | - | - | - | - | - | - | - | - | - | - | - | - | - | - |

|  |  |  |  |  |  |  |  |  |  |  |  |  |  |  |  |
|---|---|---|---|---|---|---|---|---|---|---|---|---|---|---|---|
| Library | - | - | - | - | - | - | - | - | - | - | - | - | - | - | - |
| mTFP1 |  |  |  |  |  |  |  |  |  |  |  |  |  |  |  |
| cFP484 | T | N | A | N | I | F | L | R | N | E | A | D | L | E | E | K |
| dsFP483 | - | - | - | - | - | - | - | - | - | - | - | - | - | - | - |
| amFP486 | - | - | - | - | - | - | - | - | - | - | - | - | - | - | - |
| mCherry | - | - | - | - | - | - | - | - | - | - | - | - | - | - | - |
| EGFP | - | - | - | - | - | - | - | - | - | - | - | - | - | - | - |

|  | 1 | 1a | 2 | 3 | 4 | 5 | 6 | 6a | 6b | 6c | 6d | 7 | 8 | 9 | 10 |
|---|---|---|---|---|---|---|---|---|---|---|---|---|---|---|---|
| Library | - | M | V | S | K | G | E | E | T | T | M | G | V | I | K | P |
| mTFP1 |  | M | V | S | K | G | E | E | T | T | M | G | V | I | K | P |
| cFP484 | T | L | R | I | P | K | A | L | T | T | M | G | V | I | K | P |
| dsFP483 | - | M | - | S | C | S | K | S | - | - | - | - | V | I | K | E |
| amFP486 | - | M | - | A | L | S | N | K | - | - | - | - | F | I | G | D |
| mCherry | - | M | V | S | K | G | E | E | D | N | M | A | I | I | K | E |
| EGFP | - | M | V | S | K | G | E | E | - | - | - | - | L | F | T | G |

FIG. 3B

|  | 11 | 12 | 13 | 14 | 15 | 16 | 17 | 18 | 19 | 20 | 21 | 22 | 23 | 24 | 25 | 26 |
|---|---|---|---|---|---|---|---|---|---|---|---|---|---|---|---|---|
| Library | D | M | K | I | K | L | K | M | E | G | N | V | N | G | H | A |
| mTFP1 | D | M | K | I | K | L | K | M | E | G | N | V | N | G | H | A |
| cFP484 | D | M | K | I | K | L | K | M | E | G | N | V | N | G | H | A |
| dsFP483 | E | M | L | I | D | L | H | L | E | G | T | F | N | G | H | Y |
| amFP486 | D | M | K | M | T | Y | H | M | D | G | C | V | N | G | H | Y |
| mCherry | F | M | R | F | K | V | H | M | E | G | S | V | N | G | H | E |
| EGFP | V | V | P | I | L | V | E | L | D | G | D | V | N | G | H | K |

|  | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|
| Library | F | V | I | E | G | E | G | E | G | K | P | Y | D | G | T | [HNQK] |
| mTFP1 | F | V | I | E | G | E | G | E | G | K | P | Y | D | G | T | N |
| cFP484 | F | V | I | E | G | E | G | E | G | K | P | Y | D | G | T | H |
| dsFP483 | F | E | I | K | G | K | G | K | G | Q | P | N | E | G | T | N |
| amFP486 | F | T | V | K | G | E | G | N | G | K | P | Y | E | G | T | Q |
| mCherry | F | E | I | E | G | E | G | E | G | R | P | Y | E | G | T | Q |
| EGFP | F | S | V | S | G | E | G | E | G | D | A | T | Y | G | K | L |

|  | 43 | 44 | 45 | 46 | 47 | 48 | 49 | 50 |  | 51 | 52 | 53 | 54 | 55 | 56 |
|---|---|---|---|---|---|---|---|---|---|---|---|---|---|---|---|
| Library | T | [LVAP] | N | L | E | V | K | E | - | - | G | A | P | L | P | F |
| mTFP1 | T | L | N | L | E | V | K | E | - | - | G | A | P | L | P | F |
| cFP484 | T | L | N | L | E | V | K | E | - | - | G | A | P | L | P | F |
| dsFP483 | T | V | T | L | E | V | T | K | - | - | G | G | P | L | P | F |
| amFP486 | T | S | T | F | K | V | T | M | A | N | G | G | P | L | A | F |
| mCherry | T | A | K | L | K | V | T | K | - | - | G | G | P | L | P | F |
| EGFP | T | L | K | F | I | C | T | T | - | - | - | G | K | L | P | V |

FIG. 3C

|  | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|
| Library | S | Y | D | I | L | S | N | A | F | [QKML] | Y | G | N | [KR] | [AV] | [LFI] |
| mTFP1 | S | Y | D | I | L | S | N | A | F | A | Y | G | N | R | A | F |
| cFP484 | S | Y | D | I | L | S | N | A | F | Q | Y | G | N | R | A | L |
| dsFP483 | G | W | H | I | L | C | P | Q | F | Q | Y | G | N | K | A | F |
| amFP486 | S | F | D | I | L | S | T | V | F | K | Y | G | N | R | C | F |
| mCherry | A | W | D | I | L | S | P | Q | F | M | Y | G | S | K | A | Y |
| EGFP | P | W | P | T | L | V | T | T | L | T | Y | G | V | Q | C | F |

|  | 73 | 74 | 75 | 76 | 77 | 78 | 79 | 80 |  |  | 81 | 82 | 83 | 84 | 85 | 86 |
|---|---|---|---|---|---|---|---|---|---|---|---|---|---|---|---|---|
| Library | T | K | Y | P | D | D | I | A | - | - | D | Y | [LFI] | K | Q | S |
| mTFP1 | T | K | Y | P | D | D | I | P | - | - | N | Y | F | K | Q | S |
| cFP484 | T | K | Y | P | D | D | I | A | - | - | D | Y | F | K | Q | S |
| dsFP483 | V | H | H | P | D | N | I | H | - | - | D | Y | L | K | L | S |
| amFP486 | T | A | Y | P | T | S | M | P | - | - | D | Y | F | K | Q | A |
| mCherry | V | K | H | P | A | D | I | P | - | - | D | Y | L | K | L | S |
| EGFP | S | R | Y | P | D | H | M | K | Q | H | D | F | F | K | S | A |

|  | 87 | 88 | 89 | 90 | 91 | 92 | 93 | 94 | 95 | 96 | 97 | 98 | 99 | 100 | 101 | 102 |
|---|---|---|---|---|---|---|---|---|---|---|---|---|---|---|---|---|
| Library | F | P | E | G | Y | S | W | E | R | T | M | T | F | E | D | K |
| mTFP1 | F | P | E | G | Y | S | W | E | R | T | M | T | F | E | D | K |
| cFP484 | F | P | E | G | Y | S | W | E | R | T | M | T | F | E | D | K |
| dsFP483 | F | P | E | G | Y | T | W | E | R | S | M | H | F | E | D | G |
| amFP486 | F | P | D | G | M | S | Y | E | R | T | F | T | Y | E | D | G |
| mCherry | F | P | E | G | F | K | W | E | R | V | M | N | F | E | D | G |
| EGFP | M | P | E | G | Y | V | Q | E | R | T | I | F | F | K | D | D |

FIG. 3D

|  | 103 | 104 | 105 | 106 | 107 | 108 | 109 | 110 | 111 | 112 | 113 | 114 | 115 | 116 | 117 | 118 |
|---|---|---|---|---|---|---|---|---|---|---|---|---|---|---|---|---|
| Library | G | [IT] | V | K | V | K | S | D | I | S | M | E | E | D | S | F |
| mTFP1 | G | I | V | K | V | K | S | D | I | S | M | E | E | D | S | F |
| cFP484 | G | I | V | K | V | K | S | D | I | S | M | E | E | D | S | F |
| dsFP483 | G | L | C | C | I | T | N | D | I | S | L | T | G | N | C | F |
| amFP486 | G | V | A | T | A | S | W | E | I | S | L | K | G | N | C | F |
| mCherry | G | V | V | T | V | T | Q | D | S | S | L | Q | D | G | E | F |
| EGFP | G | N | Y | K | T | R | A | E | V | K | F | E | G | D | T | L |

|  | 119 | 120 | 121 | 122 | 123 | 124 | 125 | 126 | 127 | 128 | 129 | 130 | 131 | 132 | 133 | 134 |
|---|---|---|---|---|---|---|---|---|---|---|---|---|---|---|---|---|
| Library | I | Y | E | I | R | [LFI] | [KR] | G | [KR] | N | F | P | P | N | G | P |
| mTFP1 | I | Y | E | I | H | L | K | G | E | N | F | P | P | N | G | P |
| cFP484 | I | Y | E | I | R | F | D | G | M | N | F | P | P | N | G | P |
| dsFP483 | Y | Y | D | I | K | F | T | G | L | N | F | P | P | N | G | P |
| amFP486 | E | H | K | S | T | F | H | G | V | N | F | P | A | D | G | P |
| mCherry | I | Y | K | V | K | L | R | G | T | N | F | P | S | D | G | P |
| EGFP | V | N | R | I | E | L | K | G | I | D | F | K | E | D | G | N |

|  | 135 | 136 | 137 | 138 | 139 | 140 | 141 | 142 | 143 | 144 | 145 | 146 | 147 | 148 | 149 | 150 |
|---|---|---|---|---|---|---|---|---|---|---|---|---|---|---|---|---|
| Library | V | M | Q | K | K | T | L | K | W | E | P | S | T | E | I | [ML] |
| mTFP1 | V | M | Q | K | K | T | T | G | W | D | A | S | T | E | R | M |
| cFP484 | V | M | Q | K | K | T | L | K | W | E | P | S | T | E | I | M |
| dsFP483 | V | V | Q | K | K | T | T | G | W | E | P | S | T | E | R | L |
| amFP486 | V | M | A | K | K | T | T | G | W | D | P | S | F | E | K | M |
| mCherry | V | M | Q | K | K | T | M | G | W | E | A | S | S | E | R | M |
| EGFP | I | L | G | H | K | - | L | E | Y | N | Y | N | S | H | N | V |

FIG. 3E

|  | 151 | 152 | 153 | 154 | 155 | 156 | 157 | 158 | 159 | 160 | 161 | 162 | 163 | 164 | 165 | 166 |
|---|---|---|---|---|---|---|---|---|---|---|---|---|---|---|---|---|
| Library | Y | V | R | D | G | V | L | V | G | D | I | S | [HQ] | S | L | L |
| mTFP1 | Y | V | R | D | G | V | L | K | G | D | V | K | H | K | L | L |
| cFP484 | Y | V | R | D | G | V | L | V | G | D | I | S | H | S | L | L |
| dsFP483 | Y | P | R | D | G | V | L | I | G | D | I | H | H | A | L | T |
| amFP486 | T | V | C | D | G | I | L | K | G | D | V | T | A | F | L | M |
| mCherry | Y | P | E | D | G | A | L | K | G | E | I | K | Q | R | L | K |
| EGFP | Y | I | M | A | D | K | Q | K | N | G | I | K | V | N | F | K |

|  | 167 | 168 |  |  |  |  |  | 169 | 170 | 171 | 172 | 173 | 174 | 175 | 176 | 177 |
|---|---|---|---|---|---|---|---|---|---|---|---|---|---|---|---|---|
| Library | L | E | - | - | - | - | - | G | G | G | H | Y | R | C | D | F |
| mTFP1 | L | E | - | - | - | - | - | G | G | G | H | H | R | V | D | F |
| cFP484 | L | E | - | - | - | - | - | G | G | G | H | Y | R | C | D | F |
| dsFP483 | V | E | - | - | - | - | - | G | G | G | H | Y | A | C | D | I |
| amFP486 | L | Q | - | - | - | - | - | G | G | G | N | Y | R | C | Q | F |
| mCherry | L | K | - | - | - | - | - | D | G | G | H | Y | D | A | E | V |
| EGFP | I | R | H | N | I | E | D | G | S | V | Q | L | A | D | H | Y |

|  | 178 | 179 | 180 | 181 | 182 | 183 | 184 | 185 | 186 | 187 | 188 | 189 | 190 | 191 | 192 |
|---|---|---|---|---|---|---|---|---|---|---|---|---|---|---|---|
| Library | K | [ST] | I | Y | K | A | K | K | - | V | V | K | L | P | D | Y |
| mTFP1 | K | T | I | Y | R | A | K | K | - | A | V | K | L | P | D | Y |
| cFP484 | K | S | I | Y | K | A | K | K | - | V | V | K | L | P | D | Y |
| dsFP483 | K | T | V | Y | R | A | K | K | A | A | L | K | M | P | G | Y |
| amFP486 | H | T | S | Y | K | T | K | K | - | P | V | T | M | P | P | N |
| mCherry | K | T | T | Y | K | A | K | K | - | P | V | Q | L | P | G | A |
| EGFP | Q | Q | N | T | P | I | G | D | G | P | V | L | L | P | D | N |

FIG. 3F

|  | 193 | 194 | 195 | 196 | 197 | 198 | 199 | 200 | 201 | 202 | 203 | 204 |  | 205 | 206 | 207 |
|---|---|---|---|---|---|---|---|---|---|---|---|---|---|---|---|---|
| Library | H | F | V | D | H | R | I | E | I | L | N | H | - | D | K | D |
| mTFP1 | H | F | V | D | H | R | I | E | I | L | N | H | - | D | K | D |
| cFP484 | H | F | V | D | H | R | I | E | I | L | N | H | - | D | K | D |
| dsFP483 | H | Y | V | D | T | K | L | V | I | W | N | N | - | D | K | E |
| amFP486 | H | V | V | E | H | R | I | A | R | T | D | L | - | D | K | G |
| mCherry | Y | N | V | N | I | K | L | D | I | T | S | H | - | N | E | D |
| EGFP | H | Y | L | S | T | Q | S | A | L | S | K | D | P | N | E | K |

|  | 208 | 209 | 210 | 211 | 212 | 213 | 214 | 215 | 216 | 217 | 218 | 219 | 220 | 221 | 222 | 223 |
|---|---|---|---|---|---|---|---|---|---|---|---|---|---|---|---|---|
| Library | Y | N | K | V | T | L | Y | E | N | A | V | A | R | Y | S | L |
| mTFP1 | Y | N | K | V | T | V | Y | E | S | A | V | A | R | N | S | T |
| cFP484 | Y | N | K | V | T | L | Y | E | N | A | V | A | R | Y | S | L |
| dsFP483 | F | M | K | V | E | E | H | E | I | A | V | A | R | H | H | P |
| amFP486 | G | N | S | V | Q | L | T | E | H | A | V | A | H | I | T | S |
| mCherry | Y | T | I | V | E | Q | Y | E | R | A | E | G | R | H | S | T |
| EGFP | R | D | H | M | V | L | L | E | F | V | T | A | A | G | I | T |

|  | 224 | 225 | 226 | 227 | 228 | 229 | 230 | 231 | 232 | 233 | 234 | 235 |
|---|---|---|---|---|---|---|---|---|---|---|---|---|
| Library | L | P | S | Q | A | G | M | D | E | L | Y | K |
| mTFP1 | D | G | M | D | E | L | Y | K | - | - | - | - |
| cFP484 | L | P | S | Q | A | - | - | - | - | - | - | - |
| dsFP483 | F | Y | E | P | K | K | D | K | - | - | - | - |
| amFP486 | V | V | P | F | - | - | - | - | - | - | - | - |
| mCherry | G | G | M | D | E | L | Y | K | - | - | - | - |
| EGFP | L | G | M | D | E | L | Y | K | - | - | - | - |

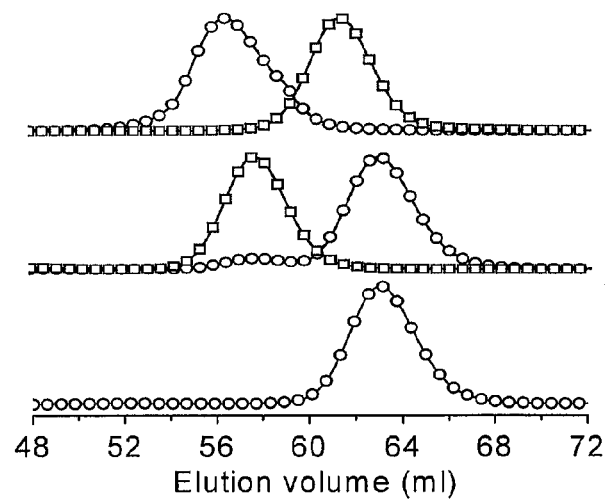
Figure 4: Characterization of mTFP1 by Gel Filtration Chromatography.

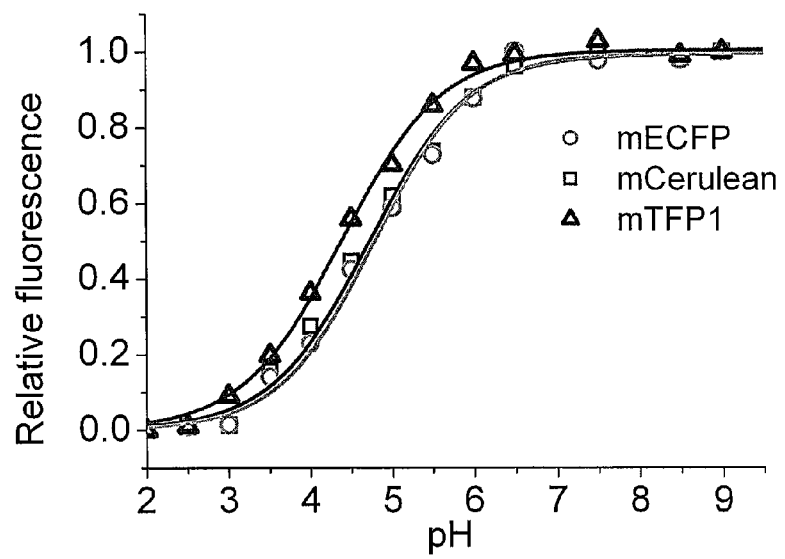
Figure 5: pH-Dependence of the fluorescence emission of mECFP, mCerulean, and mTFP1.

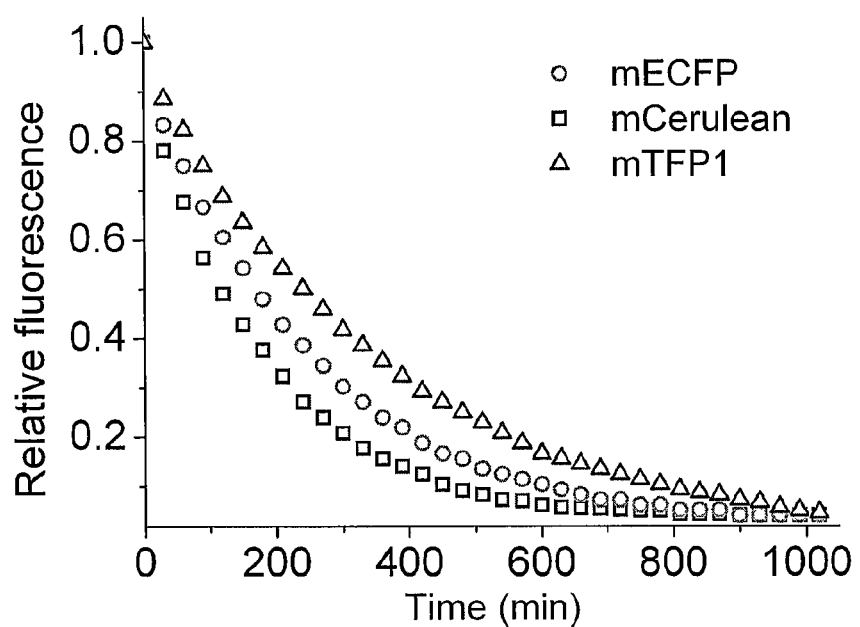
Figure 6: Relative rates of photobleaching of mECFP, mCerulean, and mTFP1.

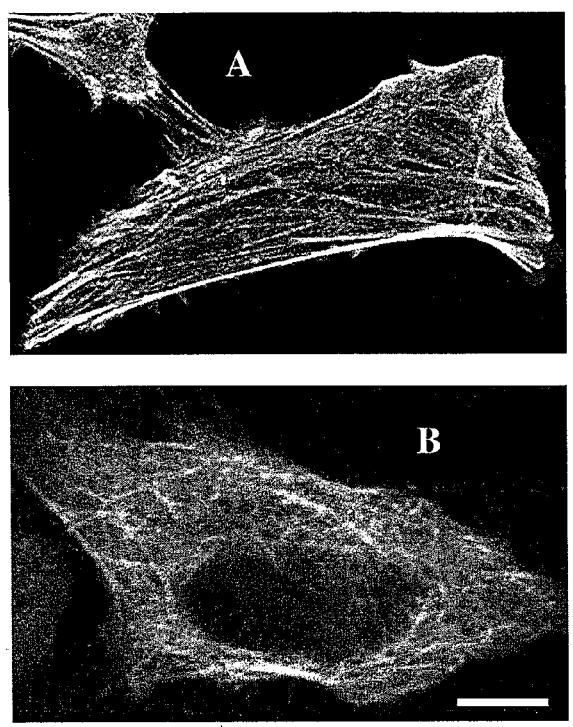
Figure 7: Confocal fluorescence image of a Hela cell expressing mTFP1-actin (scale bar = 10 μm).

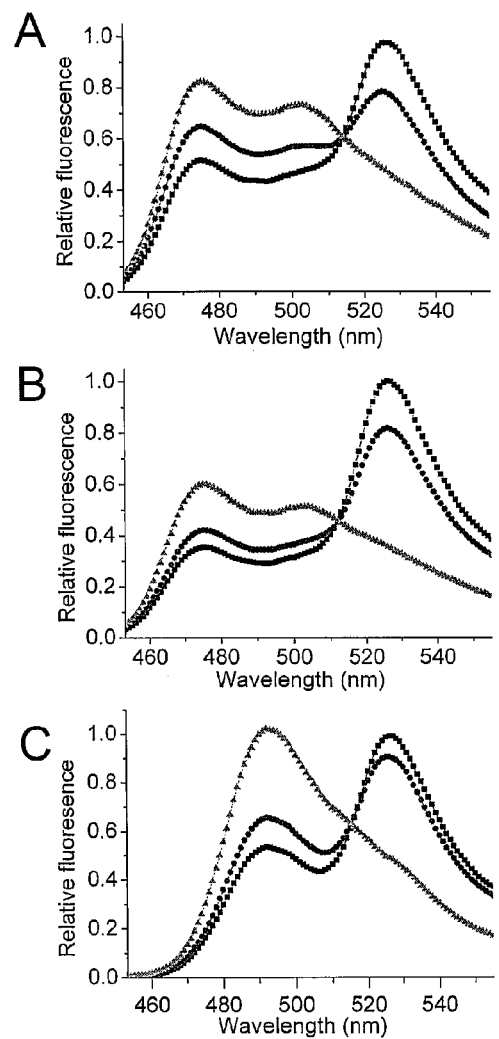
Figure 8: *In vitro* FRET responses for Cameleon constructs containing (A) mECFP, (B) mCerulean, and (C) mTFP1.

FIG. 9A
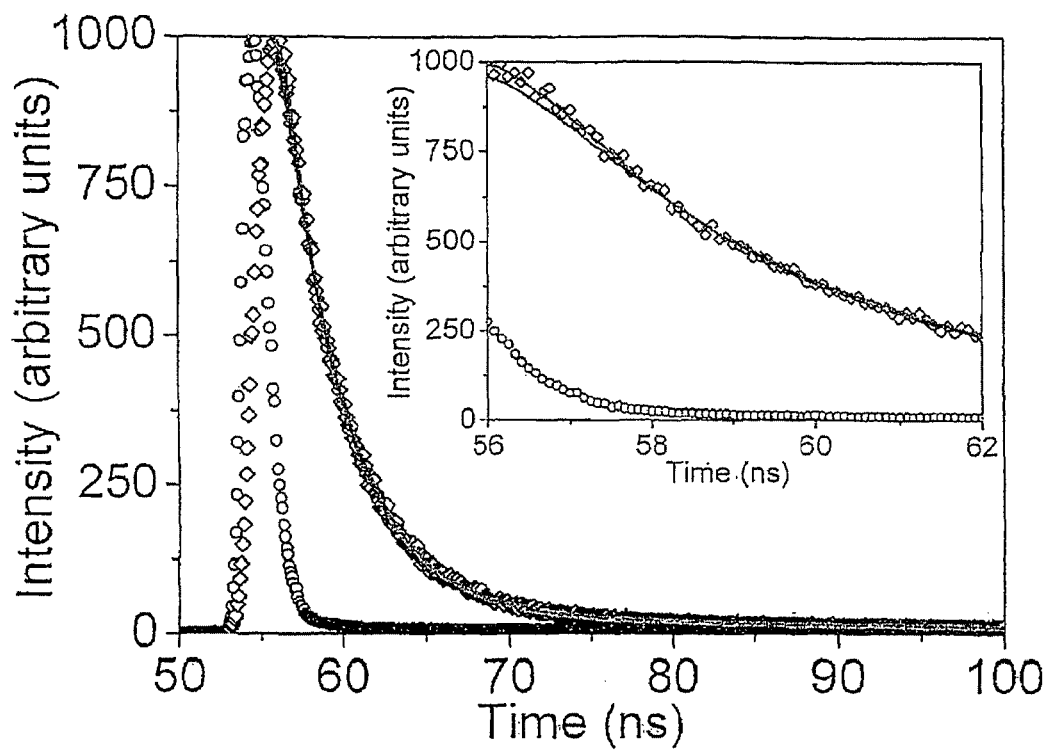
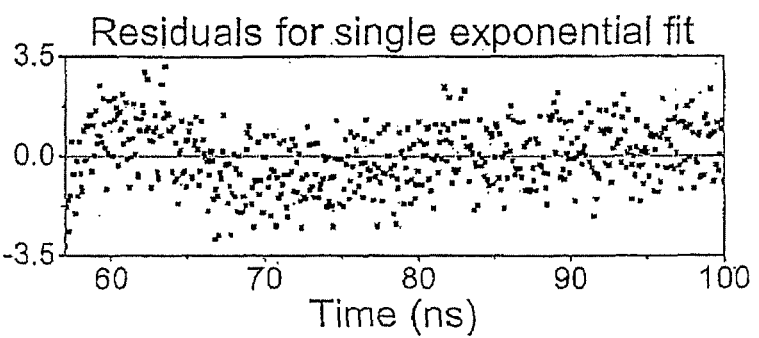
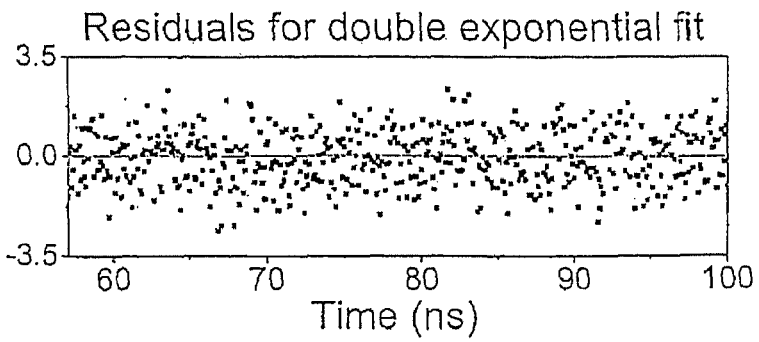

FIG. 9B
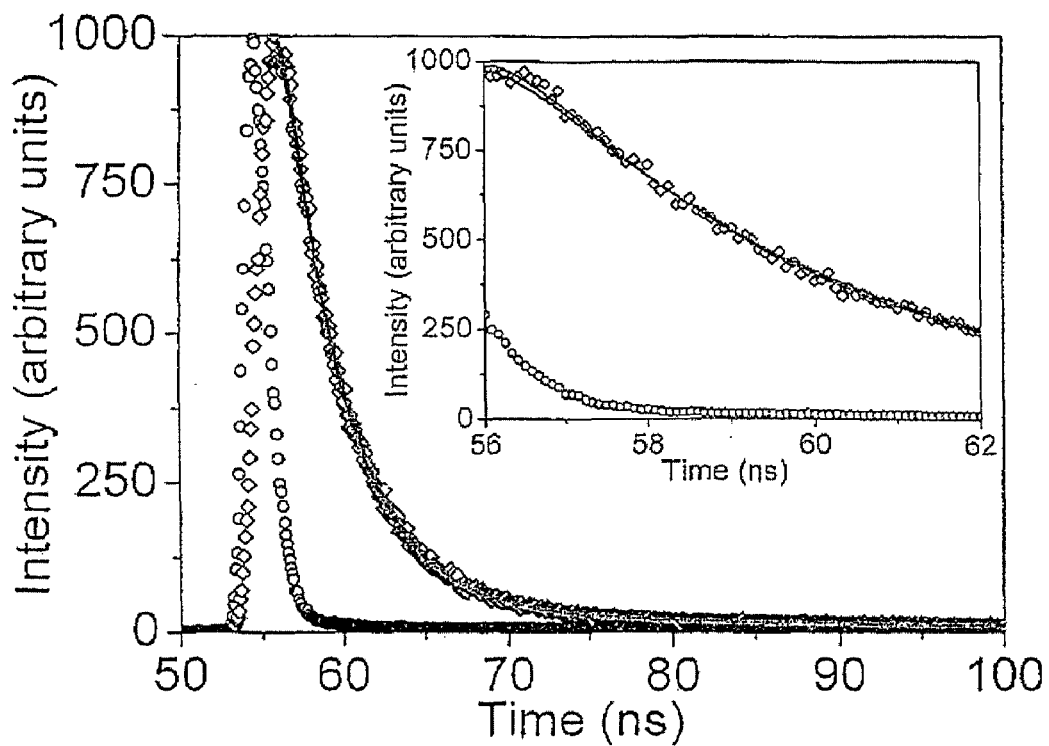
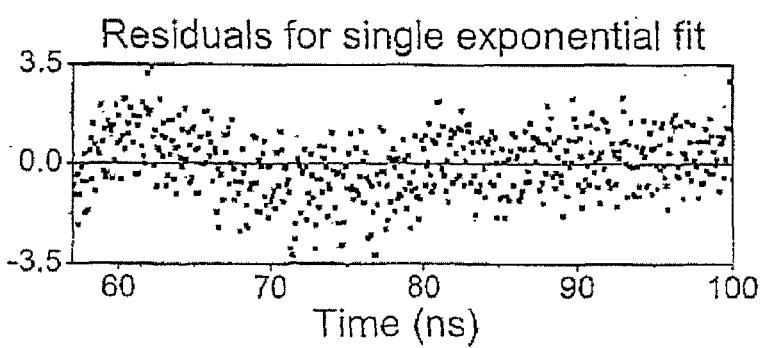
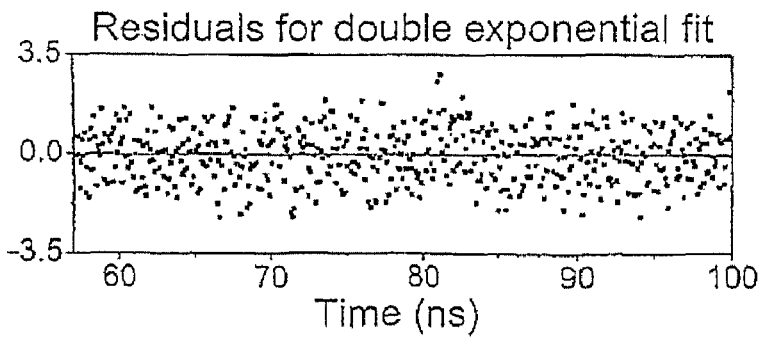

FIG. 9C
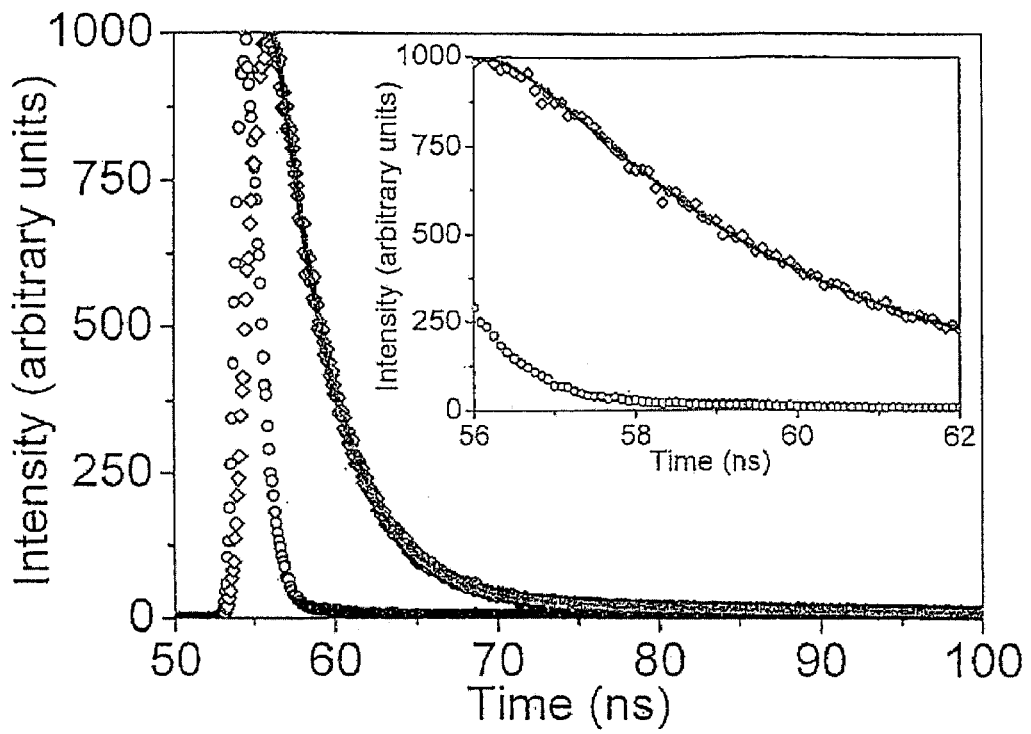
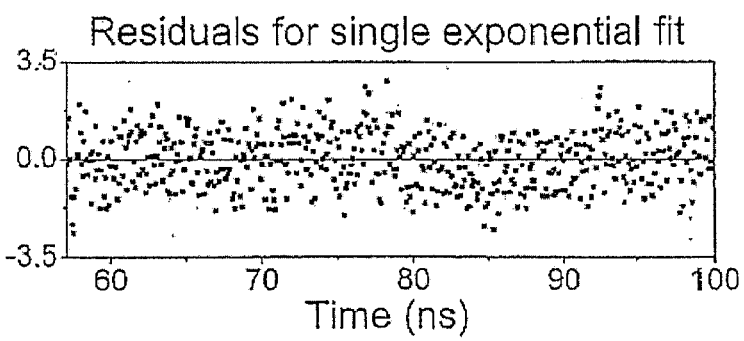
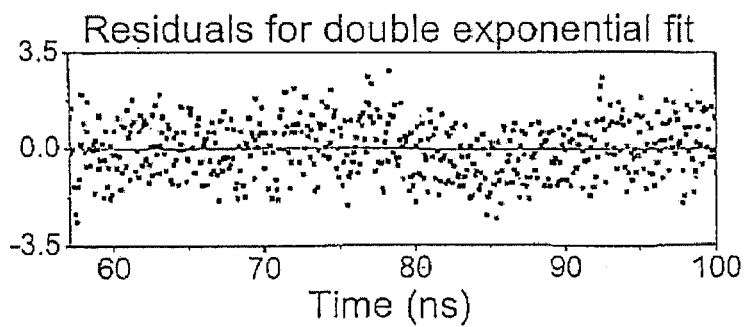

FIG. 10A

SEQ ID NO: 2 (mTFP0.86)

atggtgagcaagggcgaggagaccacaatgggcgtaatcaagcccgacatgaagatcaag
ctgaagatggagggcaacgtgaatggccacgccttcgtgatcgagggcgagggcgagggc
aagccctacgacggcaccaacaccatcaacctggaggtgaaggagggagccccccctgccc
ttctcctacgacattctgaccaacgccttcgcttacggcaacagggccttcaccaagtac
cccgacgacatccccaactacttcaagcagtccttccccgagggctactcttgggagcgc
accatgaccttcgaggacaagggcatcgtgaaggtgaagtccgacatctccatggaggag
gactccttcatctacgagatacgcctcaagggcgagaacttccccccccaacggccccgtg
atgcagaagaagaccctgaagtgggagcctccaccgagatcctgtacgtgcgcgacggc
gtgctggtgggcgacatcaagcacaagctgctgctggagggcggcggccactaccgcgtt
gacttcaagaccatctacagggccaagaaggcggtgaagctgcccgactaccacttcgtg
gaccaccgcatcgagatcctgaaccacgacaaggactacaacaaggtgaccgtttacgag
agcgccgtggcccgctactccaccggcggcatggacgagctgtacaag

FIG. 10B

SEQ ID NO: 6 (mTFP1)

atggtgagcaagggcgaggagaccacaatgggcgtaatcaagcccgacatgaagatcaag
ctgaagatggagggcaacgtgaatggccacgccttcgtgatcgagggcgagggcgagggc
aagccctacgacggcaccaacaccatcaacctggaggtgaaggagggagccccccctgccc
ttctcctacgacattctgaccaccgcgttcgcctacggcaacagggccttcaccaagtac
cccgacgacatccccaactacttcaagcagtccttccccgagggctactcttgggagcgc
accatgaccttcgaggacaagggcatcgtgaaggtgaagtccgacatctccatggaggag
gactccttcatctacgagatacacctcaagggcgagaacttccccccccaacggccccgtg
atgcagaagaagaccaccggctgggacgcctccaccgagaggatgtacgtgcgcgacggc
gtgctgaagggcgacgtcaagcacaagctgctgctggagggcggcggccaccaccgcgtt
gacttcaagaccatctacagggccaagaaggcggtgaagctgcccgactatcactttgtg
gaccaccgcatcgagatcctgaaccacgacaaggactacaacaaggtgaccgtttacgag
agcgccgtggcccgcaactccaccgacggcatggacgagctgtacaagtaa

Fig. 10

SEQ ID NO: 3 (mTFP0.86)

AGCAGGTCTAGACTCGAGCATGGTGAGCAAGGGCGAGGAGACCACAATGGGCGTA
ATCAAGCCCGACATGAAGATCAAGCTGAAGATGGAGGGCAACGTGAACGGCCACG
CCTTCGTGATCGAGGGCGAGGGCGAGGGCAAGCCCTACGACGGCACCMASACCSYC
AACCTGGAGGTGAAGGAGGGAGCCCCCCTGCCCTTCTCCTACGACATCCTGTCCAAC
GCCTTCMWGTACGGCAACARGGYCHTCACCAAGTACCCCGACGACATCGCCGACTA
CHTCAAGCAGTCCTTCCCCGAGGGCTACTCCTGGGAGCGCACCATGACCTTCGAGGA
CAAGGGCAYCGTGAAGGTGAAGTCCGACATCTCCATGGAGGAGGACTCCTTCATCT
ACGAGATCCGCHTCARGGGCARGAACTTCCCCCCCAACGGCCCCGTGATGCAGAAG
AAGACCCTGAAGTGGGAGCCCTCCACCGAGATCMTGTACGTGCGCGACGGCGTGCT
GGTGGGCGACATCTCCCASTCCCTGCTGCTGGAGGGCGGCGGCCACTACCGCTGCGA
CTTCAAGWCCATCTACAAGGCCAAGAAGGTGGTGAAGCTGCCCGACTACCACTTCG
TGGACCACCGCATCGAGATCCTGAACCACGACAAGGACTACAACAAGGTGACCCTG
TACGAGAACGCCGTGGCCCGCTACTCCCTGCTGCCCTCCCAGGCAGGCATGGACGA
GCTGTACAAGTAAGAATTCGGATCCTGCGTA

SEQ ID NO: 3 (mTFP0.86)

MVSKGEETTMGVIKPDMKIKLKMEGNVNGHAFVIEGEGEGKPYDGTNTINLEVKEGAP
LPFSYDILTNAFAYGNRAFTKYPDDIPNYFKQSFPEGYSWERTMTFEDKGIVKVKSDISM
EEDSFIYEIRLKGENFPPNGPVMQKKTLKWEPSTEILYVRDGVLVGDIKHKLLLEGGGHY
RVDFKTIYRAKKAVKLPDYHFVDHRIEILNHDKDYNKVTVYESAVARYSTGGMDELYK

FIG. 12B

SEQ ID NO: 7 (mTFP1)

MVSKGEETTMGVIKPDMKIKLKMEGNVNGHAFVIEGEGEGKPYDGTNTINLEVKEGAP
LPFSYDILTTAFAYGNRAFTKYPDDIPNYFKQSFPEGYSWERTMTFEDKGIVKVKSDISM
EEDSFIYEIHLKGENFPPNGPVMQKKTTGWDASTERMYVRDGVLKGDVKHKLLLEGGG
HHRVDFKTIYRAKKAVKLPDYHFVDHRIEILNHDKDYNKVTVYESAVARNSTDGMDEL
YK

Fig. 12

SEQ ID NO: 4 (tdTFP0.3)

atggtgagcaagggcgaggagaccacaatgggcgtaatcaagcccgacatgaagatcaagctgaagatggagggcaacgtgaatggcc
acgccttcgtgatcgagggcgagggcgagggcaagccctacgacggcaccaacaccgtcaacctggaggtgaaggagggagccccc
ctgcccttctcctacgacattctgtccaacgccttcgggtacggcaacagggccttcaccaagtaccccgacgacatcgccaactacttcaa
gcagtccttccccgagggctactcctgggagcgcaccatgaccttcgaggacaagggcatcgtgaaggtgaagtccgacatctccatgga
ggaggactccttcatctacgagatccgcctcaagggcaagaacttcccccccaacggccccgtgatgcagaagaagaccctgaagtggg
agccctccaccgagatcctgtacgtgcgcgacggcgtgctggtgggcgacatctcccactccctgctgctggagggcggcggccactac
cgctgcgacttcaagaccatctacagggccaagaaggtggtgaagctgcccgactaccacttcgtggaccaccgcatcgagatcctgaac
cacgacaaggactacaacaaggtgaccctgtacgagaacgccgtggcccgctactccctgctgcccctcccaggcaaccggcagcactct
agtcagcggctccggcaccgccaccacaatgggcgtaatcaagcccgacatgaagatcaagctgaagatggagggcaacgtgaatggc
cacgccttcgtgatcgagggcgagggcgagggcaagccctacgacggcaccaacaccgtcaacctggaggtgaaggagggagccccc
cctgcccttctcctacgacattctgtccaacgccttcgggtacggcaacagggccttcaccaagtaccccgacgacatcgccaactacttca
agcagtccttccccgagggctactcctgggagcgcaccatgaccttcgaggacaagggcatcgtgaaggtgaagtccgacatctccatgg
aggaggactccttcatctacgagatccgcctcaagggcaagaacttcccccccaacggccccgtgatgcagaagaagaccctgaagtgg
gagccctccaccgagatcctgtacgtgcgcgacggcgtgctggtgggcgacatctcccactccctgctgctggagggcggcggccacta
ccgctgcgacttcaagaccatctacagggccaagaaggtggtgaagctgcccgactaccacttcgtggaccaccgcatcgagatcctgaa
ccacgacaaggactacaacaaggtgaccctgtacgagaacgccgtggcccgctactccctgctgccccccaggcaggcatggacgag
ctgtacaag

Fig. 13

SEQ ID NO: 5 (tdTFP0.3)

MVSKGEETTMGVIKPDMKIKLKMEGNVNGHAFVIEGEGEGKPYDGTNTVNLEVKEGAP
LPFSYDILSNAFGYGNRAFTKYPDDIANYFKQSFPEGYSWERTMTFEDKGIVKVKSDISM
EEDSFIYEIRLKGKNFPPNGPVMQKKTLKWEPSTEILYVRDGVLVGDISHSLLLEGGGHY
RCDFKTTYRAKKVVKLPDYHFVDHRIEILNHDKDYNKVTLYENAVARYSLLPSQATGST
LVSGSGTATTMGVIKPDMKIKLKMEGNVNGHAFVIEGEGEGKPYDGTNTVNLEVKEGA
PLPFSYDILSNAFGYGNRAFTKYPDDIANYFKQSFPEGYSWERTMTFEDKGIVKVKSDIS
MEEDSFIYEIRLKGKNFPPNGPVMQKKTLKWEPSTEILYVRDGVLVGDISHSLLLEGGGH
YRCDFKTTYRAKKVVKLPDYHFVDHRIEILNHDKDYNKVTLYENAVARYSLLPPQAGM
DELYK

| | 20 | | | | | | | | | 30 | | | | | | | | 40 | |
|---|---|---|---|---|---|---|---|---|---|---|---|---|---|---|---|---|---|---|---|
| Library | G | N | V | N | G | H | A | F | V | I | E | G | E | G | K | P | Y | D | G | T |
| ClavCFP | G | N | V | N | G | H | A | F | V | I | E | G | E | G | K | P | Y | D | G | T |
| amFP486 | G | C | V | N | G | H | Y | F | T | V | K | G | E | N | G | K | Y | E | G | T |
| dsFP483 | G | T | F | N | G | H | Y | F | E | I | K | G | K | G | Q | P | N | E | G | T |
| dsFP583 | G | T | V | N | G | H | E | F | E | I | E | G | E | G | R | P | Y | E | G | H |
| mRFP1 | G | S | V | N | G | H | E | F | S | I | E | G | E | G | R | P | Y | E | G | T |
| avGFP | G | D | V | N | G | H | K | F | S | V | S | G | E | G | D | A | T | Y | G | K |

| | | | | | | | 50 | | | | | | | | | |
|---|---|---|---|---|---|---|---|---|---|---|---|---|---|---|---|---|---|
| Library | [HKNQ] | T | [ALPV] | N | L | E | V | K | E | - | - | G | A | P | L | P | F | S |
| ClavCFP | H | T | L | N | L | E | V | K | E | - | - | G | A | P | L | P | F | S |
| amFP486 | Q | T | S | T | F | K | V | T | M | A | N | G | G | P | L | A | F | S |
| dsFP483 | N | T | V | T | L | E | V | T | K | - | - | G | G | P | L | P | F | G |
| dsFP583 | N | T | V | K | L | K | V | T | K | - | - | G | G | P | L | P | F | A |
| mRFP1 | Q | T | A | K | L | K | V | T | K | - | - | G | G | P | L | P | F | A |
| avGFP | L | T | L | K | F | I | C | T | T | - | - | - | G | K | L | P | V | P |

FIG. 15C

|          | 60    |   |   |   |   |   | [KLMQ] | Y | G | N | [KR] | [AV] | [FIL] | T | K |
|----------|-------|---|---|---|---|---|--------|---|---|---|------|------|-------|---|---|
| Library  | Y     | D | I | L | S | N | A      | F |   |   | 70   |      |       |   |   |
| ClavCFP  | Y     | D | I | L | S | N | A      | F | Y | N | R    | A    | L     | T | K |
| amFP486  | F     | D | I | L | S | T | V      | F | Y | N | R    | C    | F     | T | A |
| dsFP483  | W     | H | I | L | C | P | Q      | F | Y | S | K    | A    | F     | V | H |
| dsFP583  | W     | D | I | L | S | P | Q      | F | A | S | K    | V    | Y     | V | K |
| mRFP1    | W     | D | I | L | S | P | Q      | F | A | S | K    | A    | Y     | V | K |
| avGFP    | W     | P | T | L | V | T | T      | F | Y | V | Q    | C    | F     | S | R |

|          | 80    |   |   |   |   | Y | [FIL] | K | Q | S | F | P | E | G | Y | S | W | E |
|----------|-------|---|---|---|---|---|-------|---|---|---|---|---|---|---|---|---|---|---|
| Library  | Y     | P | D | D | I | - | A     | D |   |   |   |   |   | 90|   |   |   |   |
| ClavCFP  | Y     | P | D | D | I | - | A     | D | Y | F | K | Q | S | F | P | E | G | Y | S | W | E |
| amFP486  | Y     | P | T | S | M | - | P     | D | Y | F | K | Q | A | F | P | D | G | M | S | Y | E |
| dsFP483  | H     | P | D | N | I | - | H     | D | Y | L | K | L | S | F | P | E | G | Y | T | W | E |
| dsFP583  | H     | P | A | D | I | - | P     | D | Y | L | K | K | L | S | F | P | E | G | F | K | W | E |
| mRFP1    | H     | P | A | D | I | - | P     | D | Y | L | K | L | S | F | P | E | G | F | K | W | E |
| avGFP    | Y     | P | D | H | M | K | Q     | H | F | K | S | A | M | P | E | G | Y | V | Q | E |

|          |   |   |   |   | 100 |   |   | D | K | G | [IT] | V | K | S | D | I | S |
|----------|---|---|---|---|-----|---|---|---|---|---|------|---|---|---|---|---|---|
| Library  | R | T | M | T | F   | E | D |   |   |   |  110 |   |   |   |   |   |   |
| ClavCFP  | R | T | M | T | F   | E | D | K | G | I | V    | K | S | D | I | S |
| amFP486  | R | T | F | T | Y   | E | D | G | G | V | A    | T | W | E | I | S |
| dsFP483  | R | S | M | H | F   | E | D | G | G | V | A    | T | C | I | T | D | I | S |
| dsFP583  | R | V | M | N | F   | E | D | G | G | V | V    | T | V | T | Q | D | S |
| mRFP1    | R | V | M | N | F   | E | D | G | G | V | V    | T | V | T | Q | D | S |
| avGFP    | R | T | I | F | F   | K | D | D | G | N | Y    | K | T | R | A | E | V | K |

FIG. 15D

| | | | | | | | | | | 120 | | | | | | | |
|---|---|---|---|---|---|---|---|---|---|---|---|---|---|---|---|---|---|
| Library | M | E | E | D | S | F | I | Y | E | I | R | [F/L] | [K/R] | G | [K/R] | N | F |
| ClavCFP | M | E | E | D | S | F | I | Y | E | I | R | F | D | G | M | N | F |
| amFP486 | L | K | G | N | C | F | E | H | K | S | T | F | H | G | V | N | F |
| dsFP483 | L | T | G | N | C | F | Y | Y | D | I | K | F | T | G | L | N | F |
| dsFP583 | L | Q | D | G | G | C | F | I | K | V | K | F | I | G | V | N | F |
| mRFP1 | L | Q | D | D | G | E | F | I | K | V | K | L | R | G | T | N | F |
| avGFP | F | E | G | D | T | L | V | N | R | I | E | L | K | G | I | D | F |

| | | | | | 130 | | | | | | | 140 | | | | | | | | 150 | |
|---|---|---|---|---|---|---|---|---|---|---|---|---|---|---|---|---|---|---|---|---|---|
| Library | P | P | N | G | P | V | M | Q | K | T | - | L | K | W | E | P | S | T | E | I | [L/M] |
| ClavCFP | P | P | N | G | P | V | M | Q | K | T | - | L | K | W | E | P | S | T | E | I | M |
| amFP486 | P | A | D | G | P | V | M | A | K | T | - | T | G | W | D | P | S | F | E | K | M |
| dsFP483 | P | P | N | G | P | V | V | Q | K | T | - | T | G | W | E | P | S | T | E | R | L |
| dsFP583 | P | S | D | G | P | V | M | Q | K | T | - | M | G | W | E | A | S | T | E | R | L |
| mRFP1 | P | S | D | G | P | V | M | Q | K | T | - | M | G | W | E | A | S | T | E | R | M |
| avGFP | K | E | D | G | N | I | L | G | H | K | L | E | Y | N | Y | N | S | H | N | V | I |

FIG. 15E

Block 1 (positions ~155–171):

| | | | | | | | | | 160 | | | | | | | | | |
|---|---|---|---|---|---|---|---|---|---|---|---|---|---|---|---|---|---|---|
| Library | Y | - | - | - | R | D | G | V | L | V | G | D | I | S | [HQ] | S | L | L |
| ClavCFP | Y | - | - | - | R | D | G | V | L | V | G | D | I | S | H | S | L | L |
| amFP486 | T | - | - | - | C | D | G | I | L | K | D | V | T | A | F | L | M | T |
| dsFP483 | Y | - | - | - | R | D | G | V | L | I | G | D | I | H | H | A | L | T |
| dsFP583 | Y | - | - | - | R | D | G | V | L | K | G | D | I | H | H | A | L | K |
| mRFP1 | Y | - | - | - | E | D | G | A | L | K | G | E | I | K | M | R | L | K |
| avGFP | M | A | D | K | Q | K | N | G | I | K | V | N | F | K | I | R | H | N |

Block 2 (positions ~172–187):

| | | | | | | | | | | | 180 | | | | | |
|---|---|---|---|---|---|---|---|---|---|---|---|---|---|---|---|---|
| Library | L | E | G | G | H | Y | R | C | D | F | K | [ST] | I | Y | K | A |
| ClavCFP | L | E | G | G | H | Y | R | C | D | F | K | S | I | Y | K | A |
| amFP486 | L | Q | G | G | N | Y | R | C | Q | F | H | T | S | Y | K | T |
| dsFP483 | V | E | D | G | H | Y | A | V | D | I | K | T | V | Y | R | A |
| dsFP583 | L | K | D | G | H | Y | L | V | E | F | K | S | I | Y | M | A |
| mRFP1 | L | K | D | G | H | Y | D | A | E | V | K | T | T | Y | M | A |
| avGFP | I | E | D | G | S | V | Q | L | A | D | H | Y | Q | Q | N | T | P |

Block 3 (positions ~188–205):

| | | | | | | | | | 190 | | | | | | | | 200 | | | | |
|---|---|---|---|---|---|---|---|---|---|---|---|---|---|---|---|---|---|---|---|---|---|
| Library | K | K | - | - | V | V | K | L | P | D | Y | H | F | V | D | H | R | I | E | I | L | N |
| ClavCFP | K | K | - | - | V | V | K | L | P | D | Y | H | F | V | D | H | R | I | E | I | L | N |
| amFP486 | K | K | - | - | P | V | T | M | P | P | N | H | V | V | E | H | R | I | A | R | T | D |
| dsFP483 | K | K | A | - | A | L | K | M | P | G | Y | H | Y | V | D | T | K | L | V | I | W | N |
| dsFP583 | K | K | - | - | P | V | Q | L | P | G | Y | Y | Y | V | D | S | K | L | D | I | T | S |
| mRFP1 | K | K | - | - | P | V | Q | L | P | G | A | Y | K | T | D | I | K | L | D | I | T | S |
| avGFP | I | G | D | G | P | V | L | L | P | D | N | H | Y | L | S | T | Q | S | A | L | S | K |

FIG. 15F

| | | | | 210 | | | | | | | 220 | |
|---|---|---|---|---|---|---|---|---|---|---|---|---|
| Library | H | D | K | D | Y | N | K | V | T | L | Y | E | N | A | V | A | R |
| ClavCFP | H | D | D | K | D | Y | N | - | K | V | T | L | Y | E | N | A | V | A | R |
| amFP486 | L | L | D | K | G | G | N | - | S | V | Q | L | T | E | H | A | V | A | H |
| dsFP483 | N | S | D | K | E | F | M | - | K | V | E | E | H | E | I | A | V | A | R |
| dsFP583 | H | P | E | E | D | Y | T | - | I | V | E | Q | Y | E | R | T | E | G | R |
| mRFP1 | H | L | N | E | E | D | Y | T | - | I | V | E | Q | Y | E | R | A | E | G | R |
| avGFP | D | P | P | N | E | K | R | D | H | M | V | L | L | E | F | V | T | A | A |

| | | | | | | | 230 | | | | |
|---|---|---|---|---|---|---|---|---|---|---|---|
| Library | Y | S | L | L | P | S | Q | A | G | M | D | E | L | Y | K |
| ClavCFP | Y | S | L | L | P | S | Q | A | - | - | - | - | - | - | - |
| amFP486 | I | T | S | V | V | P | F | - | - | - | - | - | - | - | - |
| dsFP483 | H | H | P | F | Y | E | P | K | K | D | K | - | - | - | - |
| dsFP583 | H | H | L | F | L | - | - | - | - | - | - | - | - | - | - |
| mRFP1 | H | S | T | G | A | - | - | - | Y | - | - | - | - | - | - |
| avGFP | G | I | T | H | G | M | D | E | L | Y | K | - | - | - | - |

A.

B.

| Residue | Mutated to | Codon | Cumulative library size |
|---------|------------|-------|-------------------------|
| Ile104  | I,T        | AYC   | $2^1 = 2$               |
| Asp125  | K,R        | ARG   | $2^2 = 4$               |
| Met127  | K,R        | ARG   | $2^3 = 8$               |
| His42   | H,N,Q,K    | MAS   | $2^3 * 4^1 = 32$        |
| Leu44   | L,V,A,P    | SYC   | $2^3 * 4^2 = 128$       |
| Gln66   | Q,K,M,L    | MWG   | $2^3 * 4^3 = 512$       |
| Arg70   | K,R        | ARG   | $2^4 * 4^3 = 1024$      |
| Val71   | A,V        | GYC   | $2^5 * 4^3 = 2048$      |
| Leu72   | L,F,I      | HTC   | $2^5 * 3^1 * 4^3 = 6144$ |
| Phe83   | L,F,I      | HTC   | $2^5 * 3^2 * 4^3 = 18432$ |
| Phe124  | L,F,I      | HTC   | $2^5 * 3^3 * 4^3 = 55296$ |
| Met150  | M,L        | MTG   | $2^6 * 3^3 * 4^3 = 110592$ |
| His163  | H,Q        | CAS   | $2^7 * 3^3 * 4^3 = 221184$ |
| Ser179  | S,T        | WCC   | $2^8 * 3^3 * 4^3 = 442368$ |

SEQUENCE LISTING

```
<160> NUMBER OF SEQ ID NOS: 20

<210> SEQ ID NO 1
<211> LENGTH: 760
<212> TYPE: DNA
<213> ORGANISM: Artificial
<220> FEATURE:
<223> OTHER INFORMATION: DNA sequence of the synthetic gene library

<400> SEQUENCE: 1
agcaggtcta gactcgagca tggtgagcaa gggcgaggag accacaatgg gcgtaatcaa      60
gcccgacatg aagatcaagc tgaagatgga gggcaacgtg aacggccacg ccttcgtgat     120
cgagggcgag ggcgagggca agccctacga cggcaccmas accsycaacc tggaggtgaa     180
ggagggagcc cccctgccct tctcctacga catcctgtcc aacgccttcm wgtacggcaa     240
carggychtc accaagtacc ccgacgacat cgccgactac htcaagcagt ccttccccga     300
gggctactcc tgggagcgca ccatgacctt cgaggacaag ggcaycgtga aggtgaagtc     360
cgacatctcc atggaggagg actccttcat ctacgagatc cgchtcargg gcargaactt     420
cccccccaac ggccccgtga tgcagaagaa gacccctgaag tgggagccct ccaccgagat     480
cmtgtacgtg cgcgacggcg tgctggtggg cgacatctcc castccctgc tgctggaggg     540
cggcggccac taccgctgcg acttcaagwc catctacaag gccaagaagg tggtgaagct     600
gcccgactac cacttcgtgg accaccgcat cgagatcctg aaccacgaca aggactacaa     660
```

```
caaggtgacc ctgtacgaga acgccgtggc ccgctactcc ctgctgccct cccaggcagg    720
catggacgag ctgtacaagt aagaattcgg atcctgcgta                          760

<210> SEQ ID NO 2
<211> LENGTH: 708
<212> TYPE: DNA
<213> ORGANISM: Artificial
<220> FEATURE:
<223> OTHER INFORMATION: Complete DNA sequence of mTFP0.86

<400> SEQUENCE: 2
atggtgagca agggcgagga gaccacaatg ggcgtaatca gcccgacat gaagatcaag     60 ctgaagatgg agggcaacgt gaatggccac gccttcgtga tcgagggcga gggcgagggc   120
aagccctacg acggcaccaa caccatcaac ctggaggtga aggagggagc cccctgccc    180 ttctcctacg acattctgac caacgccttc gcttacggca cagggcctt caccaagtac    240 cccgacgaca tccccaacta cttcaagcag tccttccccg agggctactc ttgggagcgc   300
accatgacct tcgaggacaa gggcatcgtg aaggtgaagt ccgacatctc catggaggag   360
gactccttca tctacgagat acgcctcaag ggcgagaact ccccccccaa cggccccgtg   420
atgcagaaga agaccctgaa gtgggagccc tccaccgaga tcctgtacgt gcgcgacggc   480
gtgctggtgg gcgacatcaa gcacaagctg ctgctggagg gcggcggcca ctaccgcgtt   540
gacttcaaga ccatctacag ggccaagaag gcggtgaagc tgcccgacta ccacttcgtg   600
gaccaccgca tcgagatcct gaaccacgac aaggactaca acaaggtgac cgtttacgag   660
agcgccgtgg cccgctactc caccggcggc atggacgagc tgtacaag              708

<210> SEQ ID NO 3
<211> LENGTH: 236
<212> TYPE: PRT
<213> ORGANISM: Artificial
<220> FEATURE:
<223> OTHER INFORMATION: Complete protein sequence of mTFP0.86

<400> SEQUENCE: 3

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Asn Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile Arg
        115                 120                 125

Leu Lys Gly Glu Asn Phe Pro Pro Asn Gly Pro Val Met Gln Lys Lys
    130                 135                 140

Thr Leu Lys Trp Glu Pro Ser Thr Glu Ile Leu Tyr Val Arg Asp Gly
145                 150                 155                 160

Val Leu Val Gly Asp Ile Lys His Lys Leu Leu Leu Glu Gly Gly Gly
                165                 170                 175
```

His Tyr Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Tyr Ser Thr Gly Gly Met Asp Glu Leu Tyr Lys
225                 230                 235

<210> SEQ ID NO 4
<211> LENGTH: 1434
<212> TYPE: DNA
<213> ORGANISM: Artificial
<220> FEATURE:
<223> OTHER INFORMATION: Complete DNA sequence of a tandem dimer of TFP,
      abbreviated tdTFP0.3

<400> SEQUENCE: 4
atggtgagca agggcgagga gaccacaatg gcgtaatca agcccgacat gaagatcaag      60
ctgaagatgg agggcaacgt gaatggccac gccttcgtga tcgagggcga gggcgagggc     120
aagccctacg acgcaccaa caccgtcaac ctggaggtga aggagggagc ccccctgccc     180
ttctcctacg acattctgtc caacgccttc gggtacggca cagggccttt caccaagtac     240
cccgacgaca tcgccaacta cttcaagcag tccttccccg agggctactc ctgggagcgc     300
accatgacct tcgaggacaa gggcatcgtg aaggtgaagt ccgacatctc catggaggag     360
gactccttca tctacgagat ccgcctcaag ggcaagaact ccccccccaa cggcccgtg      420 atgcagaaga agaccctgaa gtgggagccc tccaccgaga tcctgtacgt gcgcgacggc     480
gtgctggtgg cgacatctc ccactccctg ctgctggagg cggcggcca ctaccgctgc      540 gacttcaaga ccatctacag ggccaagaag gtggtgaagc tgcccgacta ccacttcgtg     600
gaccaccgca tcgagatcct gaaccacgac aaggactaca acaaggtgac cctgtacgag     660
aacgccgtgg cccgctactc cctgctgccc tcccaggcaa ccggcagcac tctagtcagc     720
ggctccggca ccgccaccac aatgggcgta atcaagcccg acatgaagat caagctgaag     780
atggagggca acgtgaatgg ccacgccttc gtgatcgagg gcgagggcga gggcaagccc     840
tacgacggca ccaacaccgt caacctggag gtgaaggagg gagccccccct gcccttctcc     900 tacgacattc tgtccaacgc cttcgggtac ggcaacaggg ccttcaccaa gtaccccgac     960
gacatcgcca actacttcaa gcagtccttc cccgagggct actcctggga gcgcaccatg    1020
accttcgagg acaagggcat cgtgaaggtg aagtccgaca tctccatgga ggaggactcc    1080
ttcatctacg agatccgcct caagggcaag aacttccccc caacggcccc cgtgatgcag    1140
aagaagaccc tgaagtggga gccctccacc gagatcctgt acgtgcgcga cggcgtgctg    1200
gtgggcgaca tctcccactc cctgctgctg gagggcggcg ccactaccg ctgcgacttc    1260 aagaccatct acagggccaa gaaggtggtg aagctgcccg actaccactt cgtggaccac    1320
cgcatcgaga tcctgaacca cgacaaggac tacaacaagg tgaccctgta cgagaacgcc    1380
gtggcccgct actccctgct gccccccag gcaggcatgg acgagctgta caag          1434

<210> SEQ ID NO 5
<211> LENGTH: 478
<212> TYPE: PRT
<213> ORGANISM: Artificial
<220> FEATURE:
<223> OTHER INFORMATION: Complete protein sequence of tdTFP0.3

<400> SEQUENCE: 5

```
Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Val Asn Leu Glu Val Lys Glu Gly Ala Pro Leu Pro Phe Ser Tyr Asp
    50                  55                  60

Ile Leu Ser Asn Ala Phe Gly Tyr Gly Asn Arg Ala Phe Thr Lys Tyr
65                  70                  75                  80

Pro Asp Asp Ile Ala Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile Arg
        115                 120                 125

Leu Lys Gly Lys Asn Phe Pro Pro Asn Gly Pro Val Met Gln Lys Lys
    130                 135                 140

Thr Leu Lys Trp Glu Pro Ser Thr Glu Ile Leu Tyr Val Arg Asp Gly
145                 150                 155                 160

Val Leu Val Gly Asp Ile Ser His Ser Leu Leu Leu Glu Gly Gly Gly
                165                 170                 175

His Tyr Arg Cys Asp Phe Lys Thr Ile Tyr Arg Ala Lys Lys Val Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Leu Tyr Glu Asn Ala Val Ala
    210                 215                 220

Arg Tyr Ser Leu Leu Pro Ser Gln Ala Thr Gly Ser Thr Leu Val Ser
225                 230                 235                 240

Gly Ser Gly Thr Ala Thr Thr Met Gly Val Ile Lys Pro Asp Met Lys
                245                 250                 255

Ile Lys Leu Lys Met Glu Gly Asn Val Asn Gly His Ala Phe Val Ile
            260                 265                 270

Glu Gly Glu Gly Glu Gly Lys Pro Tyr Asp Gly Thr Asn Thr Val Asn
        275                 280                 285

Leu Glu Val Lys Glu Gly Ala Pro Leu Pro Phe Ser Tyr Asp Ile Leu
    290                 295                 300

Ser Asn Ala Phe Gly Tyr Gly Asn Arg Ala Phe Thr Lys Tyr Pro Asp
305                 310                 315                 320

Asp Ile Ala Asn Tyr Phe Lys Gln Ser Phe Pro Glu Gly Tyr Ser Trp
                325                 330                 335

Glu Arg Thr Met Thr Phe Glu Asp Lys Gly Ile Val Lys Val Lys Ser
            340                 345                 350

Asp Ile Ser Met Glu Glu Asp Ser Phe Ile Tyr Glu Ile Arg Leu Lys
        355                 360                 365

Gly Lys Asn Phe Pro Pro Asn Gly Pro Val Met Gln Lys Lys Thr Leu
    370                 375                 380

Lys Trp Glu Pro Ser Thr Glu Ile Leu Tyr Val Arg Asp Gly Val Leu
385                 390                 395                 400

Val Gly Asp Ile Ser His Ser Leu Leu Leu Glu Gly Gly Gly His Tyr
                405                 410                 415
```

```
Arg Cys Asp Phe Lys Thr Ile Tyr Arg Ala Lys Lys Val Val Lys Leu
            420                 425                 430

Pro Asp Tyr His Phe Val Asp Arg Ile Glu Ile Leu Asn His Asp
            435                 440                 445

Lys Asp Tyr Asn Lys Val Thr Leu Tyr Glu Asn Ala Val Ala Arg Tyr
    450                 455                 460

Ser Leu Leu Pro Pro Gln Ala Gly Met Asp Glu Leu Tyr Lys
465                 470                 475

<210> SEQ ID NO 6
<211> LENGTH: 711
<212> TYPE: DNA
<213> ORGANISM: Artificial
<220> FEATURE:
<223> OTHER INFORMATION: Complete DNA sequence of mTFP1 (SEQ ID NO: 6)

<400> SEQUENCE: 6
atggtgagca agggcgagga gaccacaatg ggcgtaatca agcccgacat gaagatcaag      60
ctgaagatgg agggcaacgt gaatggccac gccttcgtga tcgagggcga gggcgagggc     120
aagccctacg acggcaccaa caccatcaac ctggaggtga aggagggagc ccccctgccc     180
ttctcctacg acattctgac caccgcgttc gcctacggca cagggccttt caccaagtac     240
cccgacgaca tccccaacta cttcaagcag tccttccccg agggctactc ttgggagcgc     300
accatgacct tcgaggacaa gggcatcgtg aaggtgaagt ccgacatctc catggaggag     360
gactccttca tctacgagat acacctcaag ggcgagaact ccccccccaa cggcccgtg      420 atgcagaaga agaccaccgg ctgggacgcc tccaccgaga ggatgtacgt gcgcgacggc     480
gtgctgaagg gcgacgtcaa gcacaagctg ctgctggagg cggcggcca ccaccgcgtt      540 gacttcaaga ccatctacag ggccaagaag gcggtgaagc tgcccgacta tcactttgtg     600
gaccaccgca tcgagatcct gaaccacgac aaggactaca acaaggtgac cgtttacgag     660
agcgccgtgg cccgcaactc caccgacggc atggacgagc tgtacaagta a              711

<210> SEQ ID NO 7
<211> LENGTH: 236
<212> TYPE: PRT
<213> ORGANISM: Artificial
<220> FEATURE:
<223> OTHER INFORMATION: Complete protein sequence of mTFP1 (SEQ ID
      NO: 7)

<400> SEQUENCE: 7

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Asn Thr
        35                  40                  45

Ile Asn Leu Glu Val Lys Glu Gly Ala Pro Leu Pro Phe Ser Tyr Asp
    50                  55                  60

Ile Leu Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
            100                 105                 110

Lys Ser Asp Ile Ser Met Glu Glu Asp Ser Phe Ile Tyr Glu Ile His
        115                 120                 125
```

```
Leu Lys Gly Glu Asn Phe Pro Pro Asn Gly Pro Val Met Gln Lys Lys
        130                 135                 140

Thr Thr Gly Trp Asp Ala Ser Thr Glu Arg Met Tyr Val Arg Asp Gly
145                 150                 155                 160

Val Leu Lys Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
            180                 185                 190

Lys Leu Pro Asp Tyr His Phe Val Asp His Arg Ile Glu Ile Leu Asn
        195                 200                 205

His Asp Lys Asp Tyr Asn Lys Val Thr Val Tyr Glu Ser Ala Val Ala
    210                 215                 220

Arg Asn Ser Thr Asp Gly Met Asp Glu Leu Tyr Lys
225                 230                 235

<210> SEQ ID NO 8
<211> LENGTH: 240
<212> TYPE: PRT
<213> ORGANISM: synthetic gene library
<220> FEATURE:
<223> OTHER INFORMATION: Complete protein sequence of the synthetic gene
      library (Figure 3)
<220> FEATURE:
<221> NAME/KEY: misc_feature
<222> LOCATION: (47)..(47)
<223> OTHER INFORMATION: "Xaa" is H, N, Q or K
<220> FEATURE:
<221> NAME/KEY: misc_feature
<222> LOCATION: (49)..(49)
<223> OTHER INFORMATION: "Xaa" is L, V, A or P
<220> FEATURE:
<221> NAME/KEY: misc_feature
<222> LOCATION: (71)..(71)
<223> OTHER INFORMATION: "Xaa" is Q, K, M,  or L
<220> FEATURE:
<221> NAME/KEY: misc_feature
<222> LOCATION: (75)..(75)
<223> OTHER INFORMATION: "Xaa" is K or R
<220> FEATURE:
<221> NAME/KEY: misc_feature
<222> LOCATION: (76)..(76)
<223> OTHER INFORMATION: "Xaa" is A or V
<220> FEATURE:
<221> NAME/KEY: misc_feature
<222> LOCATION: (77)..(77)
<223> OTHER INFORMATION: "Xaa" is L, F or I
<220> FEATURE:
<221> NAME/KEY: misc_feature
<222> LOCATION: (88)..(88)
<223> OTHER INFORMATION: "Xaa" is L, F or I
<220> FEATURE:
<221> NAME/KEY: misc_feature
<222> LOCATION: (109)..(109)
<223> OTHER INFORMATION: "Xaa" is I or T
<220> FEATURE:
<221> NAME/KEY: misc_feature
<222> LOCATION: (129)..(129)
<223> OTHER INFORMATION: "Xaa" is L, F or I
<220> FEATURE:
<221> NAME/KEY: misc_feature
<222> LOCATION: (130)..(130)
<223> OTHER INFORMATION: "Xaa" is K or R
<220> FEATURE:
<221> NAME/KEY: misc_feature
<222> LOCATION: (132)..(132)
<223> OTHER INFORMATION: "Xaa" is K or R
<220> FEATURE:
<221> NAME/KEY: misc_feature
<222> LOCATION: (155)..(155)
<223> OTHER INFORMATION: "Xaa" is M or L
```

```
<220> FEATURE:
<221> NAME/KEY: misc_feature
<222> LOCATION: (168)..(168)
<223> OTHER INFORMATION: "Xaa" is H or Q
<220> FEATURE:
<221> NAME/KEY: misc_feature
<222> LOCATION: (184)..(184)
<223> OTHER INFORMATION: "Xaa" is S or T

<400> SEQUENCE: 8
```

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
            20                  25                  30

Val Ile Glu Gly Glu Gly Glu Gly Lys Pro Tyr Asp Gly Thr Xaa Thr
        35                  40                  45

Xaa Asn Leu Glu Val Lys Glu Gly Ala Pro Leu Pro Phe Ser Tyr Asp
    50                  55                  60

Ile Leu Ser Asn Ala Phe Xaa Tyr Gly Asn Xaa Xaa Xaa Thr Lys Tyr
65                  70                  75                  80

Pro Asp Asp Ile Ala Asp Tyr Xaa Lys Gln Ser Phe Pro Glu Gly Tyr
                85                  90                  95

Ser Trp Glu Arg Thr Met Thr Phe Glu Asp Lys Gly Xaa Val Lys Val
            100                 105                 110

Lys Ser Asp Ile Ser Met Glu Glu Asp Ser Phe Ile Tyr Glu Ile Arg
            115                 120                 125

Xaa Xaa Gly Xaa Asn Phe Pro Pro Asn Gly Pro Val Met Gln Lys Lys
130                 135                 140

Thr Leu Lys Trp Glu Pro Ser Thr Glu Ile Xaa Tyr Val Arg Asp Gly
145                 150                 155                 160

Val Leu Val Gly Asp Ile Ser Xaa Ser Leu Leu Leu Glu Gly Gly Gly
                165                 170                 175

His Tyr Arg Cys Asp Phe Lys Xaa Ile Tyr Lys Ala Lys Lys Val Val
            180                 185                 190

Lys Leu Pro Asp Tyr His Phe Val Asp His Arg Ile Glu Ile Leu Asn
            195                 200                 205

His Asp Lys Asp Tyr Asn Lys Val Thr Leu Tyr Glu Asn Ala Val Ala
    210                 215                 220

Arg Tyr Ser Leu Leu Pro Ser Gln Ala Gly Met Asp Glu Leu Tyr Lys
225                 230                 235                 240

```
<210> SEQ ID NO 9
<211> LENGTH: 266
<212> TYPE: PRT
<213> ORGANISM: Clavularia sp.
<220> FEATURE:
<223> OTHER INFORMATION: Complete protein sequence of cFP484 (Figure 3)
<300> PUBLICATION INFORMATION:
<301> AUTHORS: Matz,M.V., Fradkov,A.F., Labas,Y.A., Savitsky,A.P.,
      Zaraisky,A.G., Markelov,M.L. and Lukyanov,S.A.
<302> TITLE: Fluorescent proteins from nonbioluminescent Anthozoa
      species
<303> JOURNAL: Nat. Biotechnol.
<304> VOLUME: 17
<305> ISSUE: 10
<306> PAGES: 969-973
<307> DATE: 1999
<308> DATABASE ACCESSION NUMBER: AAF03374
<309> DATABASE ENTRY DATE: 2004-02-17
<313> RELEVANT RESIDUES IN SEQ ID NO: (1)..(266)
```

```
<400> SEQUENCE: 9

Met Lys Cys Lys Phe Val Phe Cys Leu Ser Phe Leu Val Leu Ala Ile
1               5                   10                  15

Thr Asn Ala Asn Ile Phe Leu Arg Asn Glu Ala Asp Leu Glu Glu Lys
            20                  25                  30

Thr Leu Arg Ile Pro Lys Ala Leu Thr Thr Met Gly Val Ile Lys Pro
        35                  40                  45

Asp Met Lys Ile Lys Leu Lys Met Glu Gly Asn Val Asn Gly His Ala
    50                  55                  60

Phe Val Ile Glu Gly Glu Gly Lys Pro Tyr Asp Gly Thr His
65                  70                  75                  80

Thr Leu Asn Leu Glu Val Lys Glu Gly Ala Pro Leu Pro Phe Ser Tyr
                85                  90                  95

Asp Ile Leu Ser Asn Ala Phe Gln Tyr Gly Asn Arg Ala Leu Thr Lys
            100                 105                 110

Tyr Pro Asp Asp Ile Ala Asp Tyr Phe Lys Gln Ser Phe Pro Glu Gly
        115                 120                 125

Tyr Ser Trp Glu Arg Thr Met Thr Phe Glu Asp Lys Gly Ile Val Lys
    130                 135                 140

Val Lys Ser Asp Ile Ser Met Glu Glu Asp Ser Phe Ile Tyr Glu Ile
145                 150                 155                 160

Arg Phe Asp Gly Met Asn Phe Pro Pro Asn Gly Pro Val Met Gln Lys
                165                 170                 175

Lys Thr Leu Lys Trp Glu Pro Ser Thr Glu Ile Met Tyr Val Arg Asp
            180                 185                 190

Gly Val Leu Val Gly Asp Ile Ser His Ser Leu Leu Leu Glu Gly Gly
        195                 200                 205

Gly His Tyr Arg Cys Asp Phe Lys Ser Ile Tyr Lys Ala Lys Lys Val
    210                 215                 220

Val Lys Leu Pro Asp Tyr His Phe Val Asp His Arg Ile Glu Ile Leu
225                 230                 235                 240

Asn His Asp Lys Asp Tyr Asn Lys Val Thr Leu Tyr Glu Asn Ala Val
                245                 250                 255

Ala Arg Tyr Ser Leu Leu Pro Ser Gln Ala
            260                 265

<210> SEQ ID NO 10
<211> LENGTH: 232
<212> TYPE: PRT
<213> ORGANISM: Discosoma striata
<220> FEATURE:
<223> OTHER INFORMATION: Complete protein sequence of dsFP483 (Figure 3)
<300> PUBLICATION INFORMATION:
<301> AUTHORS: Matz,M.V., Fradkov,A.F., Labas,Y.A., Savitsky,A.P.,
      Zaraisky,A.G., Markelov,M.L. and Lukyanov,S.A.
<302> TITLE: Fluorescent proteins from nonbioluminescent Anthozoa
       species
<303> JOURNAL: Nat. Biotechnol.
<304> VOLUME: 17
<305> ISSUE: 10
<306> PAGES: 969-973
<307> DATE: 1999
<308> DATABASE ACCESSION NUMBER: AAF03370
<309> DATABASE ENTRY DATE: 2001-07-27
<313> RELEVANT RESIDUES IN SEQ ID NO: (1)..(232)
```

<400> SEQUENCE: 10

```
Met Ser Cys Ser Lys Ser Val Ile Lys Glu Glu Met Leu Ile Asp Leu
1               5                   10                  15

His Leu Glu Gly Thr Phe Asn Gly His Tyr Phe Glu Ile Lys Gly Lys
            20                  25                  30

Gly Lys Gly Gln Pro Asn Glu Gly Thr Asn Thr Val Thr Leu Glu Val
        35                  40                  45

Thr Lys Gly Gly Pro Leu Pro Phe Gly Trp His Ile Leu Cys Pro Gln
    50                  55                  60

Phe Gln Tyr Gly Asn Lys Ala Phe Val His His Pro Asp Asn Ile His
65                  70                  75                  80

Asp Tyr Leu Lys Leu Ser Phe Pro Glu Gly Tyr Thr Trp Glu Arg Ser
                85                  90                  95

Met His Phe Glu Asp Gly Gly Leu Cys Cys Ile Thr Asn Asp Ile Ser
            100                 105                 110

Leu Thr Gly Asn Cys Phe Tyr Tyr Asp Ile Lys Phe Thr Gly Leu Asn
        115                 120                 125

Phe Pro Pro Asn Gly Pro Val Val Gln Lys Lys Thr Thr Gly Trp Glu
130                 135                 140

Pro Ser Thr Glu Arg Leu Tyr Pro Arg Asp Gly Val Leu Ile Gly Asp
145                 150                 155                 160

Ile His His Ala Leu Thr Val Glu Gly Gly His Tyr Ala Cys Asp
                165                 170                 175

Ile Lys Thr Val Tyr Arg Ala Lys Lys Ala Ala Leu Lys Met Pro Gly
            180                 185                 190

Tyr His Tyr Val Asp Thr Lys Leu Val Ile Trp Asn Asn Asp Lys Glu
        195                 200                 205

Phe Met Lys Val Glu Glu His Glu Ile Ala Val Ala Arg His His Pro
    210                 215                 220

Phe Tyr Glu Pro Lys Lys Asp Lys
225                 230
```

<210> SEQ ID NO 11
<211> LENGTH: 229
<212> TYPE: PRT
<213> ORGANISM: Anemonia majano
<220> FEATURE:
<223> OTHER INFORMATION: Complete protein sequence of amFP486 (Figure 3)
<300> PUBLICATION INFORMATION:
<301> AUTHORS: Matz,M.V., Fradkov,A.F., Labas,Y.A., Savitsky,A.P.,
    Zaraisky,A.G., Markelov,M.L. and Lukyanov,S.A.
<302> TITLE: Fluorescent proteins from nonbioluminescent Anthozoa
    species
<303> JOURNAL: Nat. Biotechnol.
<304> VOLUME: 17
<305> ISSUE: 10
<306> PAGES: 969-973
<307> DATE: 1999
<308> DATABASE ACCESSION NUMBER: Q9U6Y6
<309> DATABASE ENTRY DATE: 2004-12-21
<313> RELEVANT RESIDUES IN SEQ ID NO: (1)..(229)

<400> SEQUENCE: 11

```
Met Ala Leu Ser Asn Lys Phe Ile Gly Asp Asp Met Lys Met Thr Tyr
1               5                   10                  15

His Met Asp Gly Cys Val Asn Gly His Tyr Phe Thr Val Lys Gly Glu
            20                  25                  30

Gly Asn Gly Lys Pro Tyr Glu Gly Thr Gln Thr Ser Thr Phe Lys Val
        35                  40                  45
```

```
Thr Met Ala Asn Gly Gly Pro Leu Ala Phe Ser Phe Asp Ile Leu Ser
 50                  55                  60

Thr Val Phe Lys Tyr Gly Asn Arg Cys Phe Thr Ala Tyr Pro Thr Ser
 65                  70                  75                  80

Met Pro Asp Tyr Phe Lys Gln Ala Phe Pro Asp Gly Met Ser Tyr Glu
                 85                  90                  95

Arg Thr Phe Thr Tyr Glu Asp Gly Gly Val Ala Thr Ala Ser Trp Glu
                100                 105                 110

Ile Ser Leu Lys Gly Asn Cys Phe Glu His Lys Ser Thr Phe His Gly
            115                 120                 125

Val Asn Phe Pro Ala Asp Gly Pro Val Met Ala Lys Lys Thr Thr Gly
    130                 135                 140

Trp Asp Pro Ser Phe Glu Lys Met Thr Val Cys Asp Gly Ile Leu Lys
145                 150                 155                 160

Gly Asp Val Thr Ala Phe Leu Met Leu Gln Gly Gly Asn Tyr Arg
                165                 170                 175

Cys Gln Phe His Thr Ser Tyr Lys Thr Lys Pro Val Thr Met Pro
                180                 185                 190

Pro Asn His Val Val Glu His Arg Ile Ala Arg Thr Asp Leu Asp Lys
                195                 200                 205

Gly Gly Asn Ser Val Gln Leu Thr Glu His Ala Val Ala His Ile Thr
    210                 215                 220

Ser Val Val Pro Phe
225

<210> SEQ ID NO 12
<211> LENGTH: 236
<212> TYPE: PRT
<213> ORGANISM: synthetic construct
<220> FEATURE:
<223> OTHER INFORMATION: Complete protein sequence of mCherry (Figure 3)
<300> PUBLICATION INFORMATION:
<301> AUTHORS: Shaner,N.C., Campbell,R.E., Steinbach,P.A.,
       Giepmans,B.N., Palmer,A.E. and Tsien,R.Y.
<302> TITLE: Improved monomeric red, orange and yellow fluorescent
       proteins
<303> JOURNAL: Nat. Biotechnol.
<304> VOLUME: 22
<305> ISSUE: 12
<306> PAGES: 1567-1572
<307> DATE: 2004
<308> DATABASE ACCESSION NUMBER: AAV52164
<309> DATABASE ENTRY DATE: 2004-12-17
<313> RELEVANT RESIDUES IN SEQ ID NO: (1)..(236)

<400> SEQUENCE: 12

Met Val Ser Lys Gly Glu Glu Asp Asn Met Ala Ile Ile Lys Glu Phe
  1              5                  10                  15

Met Arg Phe Lys Val His Met Glu Gly Ser Val Asn Gly His Glu Phe
                 20                  25                  30

Glu Ile Glu Gly Glu Gly Glu Gly Arg Pro Tyr Glu Gly Thr Gln Thr
             35                  40                  45

Ala Lys Leu Lys Val Thr Lys Gly Gly Pro Leu Pro Phe Ala Trp Asp
 50                  55                  60

Ile Leu Ser Pro Gln Phe Met Tyr Gly Ser Lys Ala Tyr Val Lys His
 65                  70                  75                  80

Pro Ala Asp Ile Pro Asp Tyr Leu Lys Leu Ser Phe Pro Glu Gly Phe
                 85                  90                  95

Lys Trp Glu Arg Val Met Asn Phe Glu Asp Gly Gly Val Val Thr Val
                100                 105                 110
```

```
Thr Gln Asp Ser Ser Leu Gln Asp Gly Glu Phe Ile Tyr Lys Val Lys
            115                 120                 125

Leu Arg Gly Thr Asn Phe Pro Ser Asp Gly Pro Val Met Gln Lys Lys
        130                 135                 140

Thr Met Gly Trp Glu Ala Ser Ser Glu Arg Met Tyr Pro Glu Asp Gly
145                 150                 155                 160

Ala Leu Lys Gly Glu Ile Lys Gln Arg Leu Lys Leu Lys Asp Gly Gly
                165                 170                 175

His Tyr Asp Ala Glu Val Lys Thr Thr Tyr Lys Ala Lys Lys Pro Val
            180                 185                 190

Gln Leu Pro Gly Ala Tyr Asn Val Asn Ile Lys Leu Asp Ile Thr Ser
        195                 200                 205

His Asn Glu Asp Tyr Thr Ile Val Glu Gln Tyr Glu Arg Ala Glu Gly
    210                 215                 220

Arg His Ser Thr Gly Gly Met Asp Glu Leu Tyr Lys
225                 230                 235

<210> SEQ ID NO 13
<211> LENGTH: 239
<212> TYPE: PRT
<213> ORGANISM: Artificial
<220> FEATURE:
<223> OTHER INFORMATION: Complete protein sequence of EGFP (Figure 3)

<400> SEQUENCE: 13

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235
```

<210> SEQ ID NO 14
<211> LENGTH: 225
<212> TYPE: PRT
<213> ORGANISM: Artificial
<220> FEATURE:
<223> OTHER INFORMATION: Complete protein sequence of dsFP583
      (Figure 15)

<400> SEQUENCE: 14

Met Arg Ser Ser Lys Asn Val Ile Lys Glu Phe Met Arg Phe Lys Val
1               5                   10                  15

Arg Met Glu Gly Thr Val Asn Gly His Glu Phe Glu Ile Glu Gly Glu
                20                  25                  30

Gly Glu Gly Arg Pro Tyr Glu Gly His Asn Thr Val Lys Leu Lys Val
            35                  40                  45

Thr Lys Gly Gly Pro Leu Pro Phe Ala Trp Asp Ile Leu Ser Pro Gln
50                  55                  60

Phe Gln Tyr Gly Ser Lys Val Tyr Val Lys His Pro Ala Asp Ile Pro
65                  70                  75                  80

Asp Tyr Lys Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
                100                 105                 110

Leu Gln Asp Gly Cys Phe Ile Tyr Lys Val Lys Phe Ile Gly Val Asn
            115                 120                 125

Phe Pro Ser Asp Gly Pro Val Met Gln Lys Lys Thr Met Gly Trp Glu
130                 135                 140

Ala Ser Thr Glu Arg Leu Tyr Pro Arg Asp Gly Val Leu Lys Gly Glu
145                 150                 155                 160

Ile His Lys Ala Leu Lys Leu Lys Asp Gly Gly His Tyr Leu Val Glu
                165                 170                 175

Phe Lys Ser Ile Tyr Met Ala Lys Lys Pro Val Gln Leu Pro Gly Tyr
                180                 185                 190

Tyr Tyr Val Asp Ser Lys Leu Asp Ile Thr Ser His Asn Glu Asp Tyr
            195                 200                 205

Thr Ile Val Glu Gln Tyr Glu Arg Thr Glu Gly Arg His His Leu Phe
210                 215                 220

Leu
225

<210> SEQ ID NO 15
<211> LENGTH: 225
<212> TYPE: PRT
<213> ORGANISM: Artificial
<220> FEATURE:
<223> OTHER INFORMATION: Complete protein sequence of mRFP1 (Figure 15)

<400> SEQUENCE: 15

Met Ala Ser Ser Glu Asp Val Ile Lys Glu Phe Met Arg Phe Lys Val
1               5                   10                  15

Arg Met Glu Gly Ser Val Asn Gly His Glu Phe Glu Ile Glu Gly Glu
                20                  25                  30

Gly Glu Gly Arg Pro Tyr Glu Gly Thr Gln Thr Ala Lys Leu Lys Val
            35                  40                  45

Thr Lys Gly Gly Pro Leu Pro Phe Ala Trp Asp Ile Leu Ser Pro Gln
50                  55                  60

Phe Gln Tyr Gly Ser Lys Ala Tyr Val Lys His Pro Ala Asp Ile Pro
65                  70                  75                  80

```
Asp Tyr Leu Lys Leu Ser Phe Pro Glu Gly Phe Lys Trp Glu Arg Val
                85                  90                  95

Met Asn Phe Glu Asp Gly Gly Val Val Thr Val Thr Gln Asp Ser Ser
            100                 105                 110

Leu Gln Asp Gly Glu Phe Ile Tyr Lys Val Lys Leu Arg Gly Thr Asn
        115                 120                 125

Phe Pro Ser Asp Gly Pro Val Met Gln Lys Lys Thr Met Gly Trp Glu
    130                 135                 140

Ala Ser Thr Glu Arg Met Tyr Pro Glu Asp Gly Ala Leu Lys Gly Glu
145                 150                 155                 160

Ile Lys Met Arg Leu Lys Leu Lys Asp Gly Gly His Tyr Asp Ala Glu
                165                 170                 175

Val Lys Thr Thr Tyr Met Ala Lys Lys Pro Val Gln Leu Pro Gly Ala
            180                 185                 190

Tyr Lys Thr Asp Ile Lys Leu Asp Ile Thr Ser His Asn Glu Asp Tyr
        195                 200                 205

Thr Ile Val Glu Gln Tyr Glu Arg Ala Glu Gly Arg His Ser Thr Gly
    210                 215                 220

Ala
225

<210> SEQ ID NO 16
<211> LENGTH: 235
<212> TYPE: PRT
<213> ORGANISM: Artificial
<220> FEATURE:
<223> OTHER INFORMATION: Complete protein sequence of avGFP (Figure 15)

<400> SEQUENCE: 16

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Val Gln Cys Phe Ser Arg Tyr Pro Asp His Met Lys Gln His Asp Phe
65                  70                  75                  80

Phe Lys Ser Ala Met Pro Glu Gly Tyr Val Gln Glu Arg Thr Ile Phe
                85                  90                  95

Phe Lys Asp Asp Gly Asn Tyr Lys Thr Arg Ala Glu Val Lys Phe Glu
            100                 105                 110

Gly Asp Thr Leu Val Asn Arg Ile Glu Leu Lys Gly Ile Asp Phe Lys
        115                 120                 125

Glu Asp Gly Asn Ile Leu Gly His Lys Leu Glu Tyr Asn Tyr Asn Ser
    130                 135                 140

His Asn Val Tyr Ile Met Ala Asp Lys Gln Lys Asn Gly Ile Lys Val
145                 150                 155                 160

Asn Phe Lys Ile Arg His Asn Ile Glu Asp Gly Ser Val Gln Leu Ala
                165                 170                 175

Asp His Tyr Gln Gln Asn Thr Pro Ile Gly Asp Gly Pro Val Leu Leu
            180                 185                 190

Pro Asp Asn His Tyr Leu Ser Thr Gln Ser Ala Leu Ser Lys Asp Pro
        195                 200                 205
```

```
Asn Glu Lys Arg Asp His Met Val Leu Leu Glu Phe Val Thr Ala Ala
    210                 215                 220
Gly Ile Thr His Gly Met Asp Glu Leu Tyr Lys
225                 230                 235

<210> SEQ ID NO 17
<211> LENGTH: 13
<212> TYPE: DNA
<213> ORGANISM: Artificial
<220> FEATURE:
<223> OTHER INFORMATION: Kozak sequence
<220> FEATURE:
<221> NAME/KEY: misc_feature
<222> LOCATION: (10)..(12)
<223> OTHER INFORMATION: "ATG" is the start codon

<400> SEQUENCE: 17
gccaccgcca tgc                                                        13

<210> SEQ ID NO 18
<211> LENGTH: 18
<212> TYPE: PRT
<213> ORGANISM: Artificial
<220> FEATURE:
<223> OTHER INFORMATION: endoplasmic reticulum targeting sequence of
      calreticulin

<400> SEQUENCE: 18

Met Leu Leu Ser Val Pro Leu Leu Leu Gly Leu Leu Gly Leu Ala Ala
1               5                   10                  15
Ala Asp

<210> SEQ ID NO 19
<211> LENGTH: 711
<212> TYPE: DNA
<213> ORGANISM: Artificial
<220> FEATURE:
<223> OTHER INFORMATION: DNA sequence of mWasabi

<400> SEQUENCE: 19
atggtgagca agggcgagga gaccacaatg ggcgtaatca gcccgacat gaagatcaag        60 ctgaagatgg agggcaacgt gaatggccac gccttcgtga tcgagggcga gggcgagggc       120
aagccctacg acgcaccaa caccatcaac ctggaggtga aggagggagc cccctgccc        180 ttctcctacg acattctgac caccgcgttc agttacggca cagggcctt caccaagtac       240 cccgacgaca tccccaacta cttcaagcag tccttccccg agggctactc ttgggagcgc      300
accatgacct tcgaggacaa gggcatcgtg aaggtgaagt ccgacatctc catggaggag      360
gactccttca tctacgagat acacctcaag ggcgagaact tcccccccaa cggccccgtg      420
atgcagaagg agaccaccgg ctgggacgcc tccaccgaga ggatgtacgt gcgcgacggc      480
gtgctgaagg gcgacgtcaa gatgaagctg ctgctggagg gcggcggcca ccaccgcgtt      540
gacttcaaga ccatctacag ggccaagaag gcggtgaagc tgcccgacta tcactttgtg      600
gaccaccgca tcgagatcct gaaccacgac aaggactaca caaggtgac cgtttacgag       660 atcgccgtgg cccgcaactc caccgacggc atggacgagc tgtacaagta a               711

<210> SEQ ID NO 20
<211> LENGTH: 236
<212> TYPE: PRT
<213> ORGANISM: Artificial
<220> FEATURE:
<223> OTHER INFORMATION: Complete protein sequence of mWasabi
```

-continued

```
<400> SEQUENCE: 20

Met Val Ser Lys Gly Glu Glu Thr Thr Met Gly Val Ile Lys Pro Asp
1               5                   10                  15

Met Lys Ile Lys Leu Lys Met Glu Gly Asn Val Asn Gly His Ala Phe
                20                  25                  30

Val Ile Glu Gly Glu Gly Glu Gly Lys Pro Tyr Asp Gly Thr Asn Thr
            35                  40                  45

Ile Asn Leu Glu Val Lys Glu Gly Ala Pro Leu Pro Phe Ser Tyr Asp
    50                  55                  60

Ile Ser Thr Thr Ala Phe Ala Tyr Gly Asn Arg Ala Phe Thr Lys Tyr
65                  70                  75                  80

Pro Asp Asp Ile Pro Asn Tyr Phe Lys Gln Ser Phe Pro Glu Gly Tyr
                85                  90                  95

Ser Trp Glu Arg Thr Met Thr Phe Glu Asp Lys Gly Ile Val Lys Val
                100                 105                 110

Lys Ser Asp Ile Ser Met Glu Glu Asp Ser Phe Ile Tyr Glu Ile His
            115                 120                 125

Leu Lys Gly Glu Asn Phe Pro Pro Asn Gly Glu Val Met Gln Lys Lys
    130                 135                 140

Thr Thr Gly Trp Asp Ala Ser Thr Glu Arg Met Tyr Val Arg Asp Gly
145                 150                 155                 160

Val Leu Met Gly Asp Val Lys His Lys Leu Leu Leu Glu Gly Gly Gly
                165                 170                 175

His His Arg Val Asp Phe Lys Thr Ile Tyr Arg Ala Lys Lys Ala Val
                180                 185                 190

Lys Leu Pro Asp Tyr His Phe Val Asp His Arg Ile Glu Ile Leu Asn
    195                 200                 205

His Asp Lys Asp Tyr Asn Lys Ile Thr Val Tyr Glu Ser Ala Val Ala
    210                 215                 220

Arg Asn Ser Thr Asp Gly Met Asp Glu Leu Tyr Lys
225                 230                 235
```

US 7,935,801 B2

TEAL FLUORESCENT PROTEINS

CROSS REFERENCE TO RELATED APPLICATIONS

The present application is a Continuation-In-Part of co-pending U.S. patent application Ser. No. 11/419,437 filed on May 19, 2006 which claims priority from U.S. Provisional Patent Application No. 60/682,848 filed on May 20, 2005. Each of the aforementioned applications is incorporated herein in its entirety by reference.

FIELD OF THE INVENTION

The present invention relates to fluorescent proteins and, in particular, monomeric teal fluorescent proteins.

BACKGROUND

The *Aequorea victoria* green fluorescent protein (GFP), along with its various homologues and mutants (Shaner, 2005; Shimomura, 1979), has enabled live-cell fluorescence imaging of recombinant fusion proteins to become a popular and widely-accessible technique in cell-biology research (Tsien, 1998; Zhang, 2002). The defining feature of *Aequorea* GFP is its ability to autonomously generate a green fluorophore within the confines of its distinctive β-barrel structure (Shimomura, 1979; Yang, 1996; Ormo, 1996). The chromophore of GFP is post-translationally and autonomously generated, through a stepwise process that involves a main-chain cyclization (Gly67 N to Ser65 C), a dehydration (Ser65 C—N), and an oxidation (Tyr66 Ca—C) that effectively conjugates the phenolic side chain of tyrosine 66 to a five-membered ring heterocycle formed from the main-chain atoms of serine 65, tyrosine 66, and glycine 67 (FIG. 1). In the ground state of the wild-type GFP, the chromophore exists as a mixture of neutral phenol (maximum absorbance at 395 nm) and anionic phenolate forms (maximum absorbance at 475 nm). In the excited state, the neutral phenol form deprotonates to form the phenolic anion; therefore, only a single fluorescence emission peak (maximum fluorescence at 504 nm) is observed.

The steric, electrostatic, and hydrogen-bonding environment imposed upon the chromophore by the surrounding residues strongly influences the fluorescence properties. The GFP chromophore has proven remarkably amenable to genetic modification of both its covalent structure and its local environment, and this tolerance has been exploited for the creation of wavelength-shifted variants (Tsien, 1998). *Aequorea* GFP variants (Shaner, 2005) have been engineered with altered colors, brightness, photostability, ion-sensitivity (Hanson, 2002), and photoswitching properties (Lukyanov, 2005). Amino-acid substitutions at position 65 and at several other residues in the immediate vicinity of the chromophore (e.g., position 203) have resulted in GFP variants (i.e., enhanced GFP (EGFP) with maximum fluorescence at 510 nm). A particularly important class of useful variants that have resulted from such efforts is the yellow fluorescent proteins (YFPs) that are defined by the Thr203Tyr mutation (Ormo, 1996) and an emission peak that is ~25 nm red-shifted from the wild type emission peak of ~504-509 nm. However, at present, there is no known report of an *Aequorea* GFP mutant with a tyrosine-derived chromophore and fluorescence that is blue-shifted relative to the wild-type protein (i.e., it has a maximum fluorescence that is less than 504 nm).

The term "cyan fluorescent protein", or "CFP", is generally reserved for any GFP homologue with maximum fluorescence emission between approximately 470 nm and 495 nm. To date, substitutions of tyrosine 66 to other aromatic amino acids have proved to be the only approach for blue-shifting the fluorescence emission relative to the wild-type protein, in order to produce a CFP. For example, the widely used *Aequorea* GFP-derived CFP known as avCFP (also commonly known as ECFP or CFP) was engineered by replacing Tyr66 of *Aequorea* GFP with a tryptophan, to give an indole-containing chromophore (FIG. 1) (Heim, 1994) that had an emission peak in the cyan region (~480 nm) of the visible spectrum. Although the original Tyr66Trp mutant of *Aequorea* GFP was only weakly fluorescent, efforts to improve the brightness yielded the widely used variant ECFP (Heim, 1994; Miyawaki, 1997) and more recently Cerulean (Rizzo, 2004) and CyPet (Nguyen, 2005). While avCFP has been proven as a useful fluorophore in multicolor labeling applications, and as the preferred Forster resonance energy transfer (FRET) donor to a YFP acceptor, its spectral properties limit its utility in some applications. Specifically, avCFP is relatively dim, has broad excitation and emission peaks (FIG. 2), and has a multi-exponential fluorescence lifetime. The multi-exponential fluorescence lifetime of avCFP complicates the use of this protein in fluorescence lifetime imaging (FLIM) applications. Some limitations have been partially addressed in the newer variants; Cerulean is twofold brighter and has a more homogenous fluorescence lifetime (Rizzo, 2004), while CyPet exhibits high FRET to the YFP variant YPet (Nguyen, 2005). However, despite these improvements, Cerulean and CyPet remain limited by fluorescent brightness that is less than 50% of the popular YFP variant Citrine (Shaner, 2005) and that is inferior to EGFP, and by fluorescence lifetimes that are poorly fit as single-exponentials, and a very broad fluorescence emission relative to other popular variants (FIG. 2) (Rizzo, 2004).

Thus, there is a need in the art for a fluorescent protein which mitigates the difficulties of the prior art.

SUMMARY OF THE INVENTION

In view of the problems associated with known fluorescent proteins, as described above, the inventors have engineered a novel non-oligomerizing CFP with a tyrosine-derived chromophore that has unexpectedly superior fluorescence properties, and have adopted the name 'teal fluorescent proteins (TFP)' with a preceding 'd' for dimeric or 'm' for monomeric, and a succeeding numerical identifier, to identify certain variants of the present invention.

Accordingly, in one aspect, the present invention comprises an isolated nucleic acid sequence encoding a non-oligomerizing *Clavularia* teal fluorescent protein (TFP) variant having a tyrosine-derived chromophore. In certain embodiments, the nucleic acid sequence may be compatible with mammalian (e.g., human) codon usage. In one embodiment, the nucleic acid sequence has at least about 60% homology with the nucleotide sequence of SEQ ID NO: 2, SEQ ID NO: 6 or SEQ ID NO: 19. In another embodiment, the nucleic acid sequence has at least about 75% homology with the nucleotide sequence of SEQ ID NO: 2, SEQ ID NO: 6 or SEQ ID NO: 19. In still another embodiment, the nucleic acid sequence is substantially the same as, or identical to, the nucleotide sequence of SEQ ID NO: 2, SEQ ID NO: 6 or SEQ ID NO: 19. In another embodiment, the nucleic acid sequence is one that encodes the amino acid sequence of SEQ ID NO: 3, SEQ ID NO: 7 or SEQ ID NO: 20. Also provided is a fragment or derivative of the nucleic acid sequence of the invention. The present invention further provides an isolated nucleic acid, or mimetic or complement thereof, which hybridizes under stringent conditions to the nucleic acid sequence of the invention.

In one embodiment, the present invention provides a nucleic acid sequence comprising the nucleic acid sequence of SEQ ID NO: 19 (Genbank Accession EU024648) which encodes the amino acid sequence of mWasabi (SEQ ID NO: 20).

In another aspect, the present invention provides a method of engineering an isolated nucleic acid sequence encoding a non-oligomerizing *Clavularia* teal fluorescent protein (TFP) variant having a tyrosine-derived chromophore, by screening a fully-synthetic gene library. In one embodiment, the gene library comprises the nucleotide sequence of SEQ ID NO: 1.

In still another aspect, the present invention provides a vector that includes a nucleic acid sequence encoding a non-oligomerizing teal fluorescent protein (TFP) variant having a tyrosine-derived chromophore. In one embodiment, the vector is a plasmid. In another embodiment, the nucleic acid sequence of the vector is cDNA. Also provided is a host cell comprising the vector. The present invention further provides use of the vector in a method for expressing the nucleic acid sequence in mammalian cells. In one embodiment, the nucleic acid sequence is expressed as a tandem genetic fusion to another protein.

In a further aspect, the present invention provides a *Clavularia* teal fluorescent protein (TFP) variant having a tyrosine-derived chromophore and having an amino acid sequence selected from:
  a) the sequence depicted in SEQ ID NO: 20;
  b) a sequence having at least 60% homology with the amino acid sequence depicted in SEQ ID NO: 20 and comprising a mutation at H163 and H42;
  (c) a sequence having at least 75% homology with the amino acid sequence depicted in SEQ ID NO: 20 and comprising a mutation at H163 and H42.

In one embodiment, the *Clavularia* TFP variant may be a monomer or dimer. In one embodiment, the chromophore comprises the amino acid sequence tyrosine-glycine (YG). For example, the chromophore may comprise the amino acid sequence glutamine-tyrosine-glycine (QYG); the chromophore may also comprise the amino acid sequence alanine-tyrosine-glycine (AYG), cysteine-tyrosine-glycine (CYG), glycine-tyrosine-glycine (GYG) or serine-tyrosine-glycine (SYG).

In another embodiment, the TFP variant comprises at least one or more of the following mutations: histidine 42 replaced with asparagine; leucine 44 replaced with valine or isoleucine; serine 62 replaced with threonine; asparagine 63 replaced with threonine; glutamine 66 replaced with cysteine or glycine or alanine; leucine 72 replaced with phenylalanine; alanine 80 replaced with proline; aspartate 81 replaced with asparagine; arginine 123 replaced with histidine; phenylalanine 124 replaced with leucine; aspartate 125 replaced with lysine; methionine 127 replaced with lysine or glutamate; leucine 141 replaced with threonine; lysine 142 replaced with glycine; glutamate 144 replaced with aspartate; proline 145 replaced with alanine; isoleucine 149 replaced with arginine; leucine 150 replaced with methionine; valine 158 replaced with lysine; isoleucine 161 replaced with valine; serine 162 replaced with lysine; serine 164 replaced with lysine; tyrosine 173 replaced with histidine; cysteine 175 replaced with valine; serine 179 replaced with threonine; lysine 182 replaced with arginine; valine 186 replaced with alanine; leucine 213 replaced with valine; asparagine 216 replaced with serine; tyrosine 221 replaced with asparagine; glycine 224 replaced with aspartate; or serine 226 replaced with proline.

In another embodiment, in addition to the one or more mutations referred to above, the TFP variant may comprise at least one or more of the following mutations: alanine 66 replaced with serine, lysine 139 replaced with glutamic acid, histidine 163 replaced with methionine, or serine 216 replaced with isoleucine.

In a further embodiment, the present invention comprises the TFP variant comprising the amino acid sequence of SEQ ID NO: 20, referred to herein as mWasabi.

The TFP variant of the present invention may comprise an amino acid sequence having at least about 60% homology with the amino acid sequence of SEQ ID NO: 3, SEQ ID NO: 7 or SEQ ID NO: 20. In one embodiment, the TFP variant comprises an amino acid sequence having at least about 75% homology with the amino acid sequence of SEQ ID NO: 3, SEQ ID NO: 7 or SEQ ID NO: 20. In another embodiment, the TFP variant comprises an amino acid sequence which is substantially the same as, or identical to, the amino acid sequence of SEQ ID NO: 3, SEQ ID NO: 7 or SEQ ID NO: 20.

In one embodiment, the TFP variant of the present invention has a fluorescence emission that is blue-shifted relative to wild-type cFP484 protein. In one embodiment, the TFP variant has a wavelength of maximum fluorescence emission that is less than about 504 nm. The TFP variant may also have an excitation spectrum ranging from about 350 to 500 nm and an emission spectrum ranging from about 450 to 600 nm. In one embodiment, the TFP variant has an excitation maximum ranging from about 450 to 460 nm and an emission maximum ranging from about 485 to 495 nm. In one embodiment, the TFP variant has an excitation maximum of about 493 nm and an emission maximum of about 509 nm.

In yet another aspect, the present invention provides an antibody that specifically binds to the TFP variant of the invention. In one embodiment, the antibody is a polyclonal antibody; in another embodiment, the antibody is a monoclonal antibody.

In a further aspect, the present invention provides a tandem dimer comprising two TFP dimers, operatively linked by a peptide linker. In one embodiment, the tandem dimer comprises the amino acid sequence of SEQ ID NO: 5.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 3: Protein sequence alignments of mTFP1, coral CFPs, and relevant homologues. The aligned sequences are the designed synthetic gene library (SEQ ID NO: 8), mTFP1 (SEQ ID NO: 7), cFP484 from *Clavularia* sp. (Genbank accession AAF03374) (SEQ ID NO: 9), dsFP483 from *Discosoma striata* (Genbank accession AAF03370) (SEQ ID NO: 10), amFP486 from *Anemonia majano* (Genbank accession Q9U6Y6) (SEQ ID NO: 11), mCherry derived from *Discosoma striata* dsFP583 (Genbank accession AAV52164) (SEQ ID NO: 12) and EGFP derived from *Aequorea* GFP (SEQ ID NO: 13) (from Clontech vector pEGFP) (Shaner, 2004; Matz, 1999). Residues shaded cyan are changes or point mutations that were beneficial for mTFP1. Residues 66, 67, and 68 (enclosed in black box) are the precursors of the chromophore. Of the 227 structurally aligned residues of the 3 coral CFPs, there are 78 residues that are conserved in all 3 and an additional 91 residues that are conserved in 2 of the 3. Considering only those positions of two-thirds conservation, the inventors determined that cFP484 is the variant at 19%, dsFP483 at 34%, and amFP486 at 47% of the positions, and, cFP484 is the closest to the consensus sequence. The rationale behind the design of the gene library is summarized in Table 1. Numbering is consistent with DsRed and its monomeric variants that have no internal insertions or deletions relative to cFP484.

FIG. 4: Characterization of mTFP1 by Gel Filtration Chromatography. Gel filtration chromatography elution profile with detection at either 450 nm or 550 nm. The upper profile is a co-injection of dTFP0.2 and mCherry (Shaner, 2004) (a red monomer), the middle profile is dTomato (Shaner, 2004) (a red dimer) and mTFP1, and the lower profile is mTFP1 alone. The small 450 nm peak at the dimer elution volume is due to the weak absorbance of dTomato at this wavelength.

FIG. 5: pH-Dependence of the fluorescence emission of mECFP, mCerulean, and mTFP1. Each protein (stock solution of 1 mg/ml in 5 mM Tris pH 7) was diluted 1:100 in a 96-well plate containing 0.1 ml buffer (100 mM) at the indicated pH. Complete emission spectra at each pH were acquired in a plate reader equipped with monochromators.

FIG. 6: Relative rates of photo-bleaching of mECFP, mCerulean, and mTFP1. Photo-bleaching experiments were done directly on live colonies of *E. coli* on agar plates using the LED-based illumination system as described in the examples herein. Each data point represents the averaged mean fluorescence of 5 individual bacterial colonies expressing the indicated protein.

FIG. 7: Confocal fluorescence image of a Hela cell expressing mTFP1-actin (scale bar=10 µm). (A) HeLa cell expressing mTFP1-β-actin (scale bar=10 µm). (B) HeLa cell expressing mTFP1-α-tubulin (scale bar=10 µm).

FIG. 8: In vitro FRET responses for Cameleon (Miyawaki, 1997) constructs containing (A) mECFP, (B) mCerulean, and (C) mTFP1. For each protein the 3 spectra represent no $Ca^{2+}$ (red), 10 mM $Ca^{2+}$ (black), and no FRET (green). To obtain the 'no FRET' spectra, the linkers between the two fluorescent proteins were digested with trypsin under conditions where the fluorescent proteins themselves remain intact. The FRET efficiencies (E) in Table 1 were calculated using the formula E=1−(fluorescence at 490 nm before trypsin/fluorescence at 490 nm after trypsin).

FIG. 9: Fluorescence lifetime decay data for (A) mECFP, (B) mCerulean, and (C) mTFP1. Shown in each panel is the experimental data for the lifetime decay (open diamonds) and the instrument response function (IRF) for a scattering solution (open circles). The lifetime decay, convolved with the IRF, has been fitted with both single (green) and double (red) exponential decay functions. The inset is an expanded version of the region from 56 to 62 nm. For each protein, the residuals of the best fits are also shown. Excitation wavelength (nitrogen dye laser at 440 nm), emission wavelength (490 nm), and slits (1 nm) were the same for all experiments. Repeating the experiment under 'magic angle' conditions had no effect on the observed lifetimes.

FIG. 10A sets forth the complete DNA sequence of mTFP0.86 (SEQ ID NO:2) and 10B sets forth the complete DNA sequence of mTFP1 (SEQ ID NO: 6).

FIG. 11 sets forth the complete DNA sequence of the synthetic gene library (SEQ ID NO:1). The synthetic gene library was digested with XbaI and BamHI, and ligated into pUC18 digested with the same enzymes. Transformation of *E. coli* with the ligated product gave at least $10^6$ transformants. Plasmid DNA was prepared from the transformed *E. coli*, and digested with XhoI and EcoRI; the 736-bp fragment was then purified. This fragment was inserted into suitably-digested pBAD/HisB (Invitrogen) to create the final library suitable for expression and screening in colonies of *E. coli* strain LMG194.

FIG. 12A sets forth the complete protein sequence of mTFP0.86 (SEQ ID NO: 3) and 12B sets forth the complete protein sequence of mTFP1 (SEQ ID NO: 7).

FIG. 13 sets forth the complete DNA sequence of a tandem dimer of TFP, abbreviated as tdTFP0.3 (SEQ ID NO: 4).

FIG. 14 sets forth the complete protein sequence of tdTFP0.3 (SEQ ID NO: 5).

FIG. 15 shows the structure-based protein sequence alignment of the designed synthetic library (SEQ ID NO: 8), TFP (ClavCFP) (SEQ ID NO: 9), amFP486 (SEQ ID NO: 11), dsFP483 (SEQ ID NO: 10), dsFP583 (DsRed) (SEQ ID NO: 14), mRFP1 (SEQ ID NO: 15), and *Aequorea* GFP (avGFP) (SEQ ID NO: 16).

DETAILED DESCRIPTION OF PREFERRED EMBODIMENTS

Figure 1:
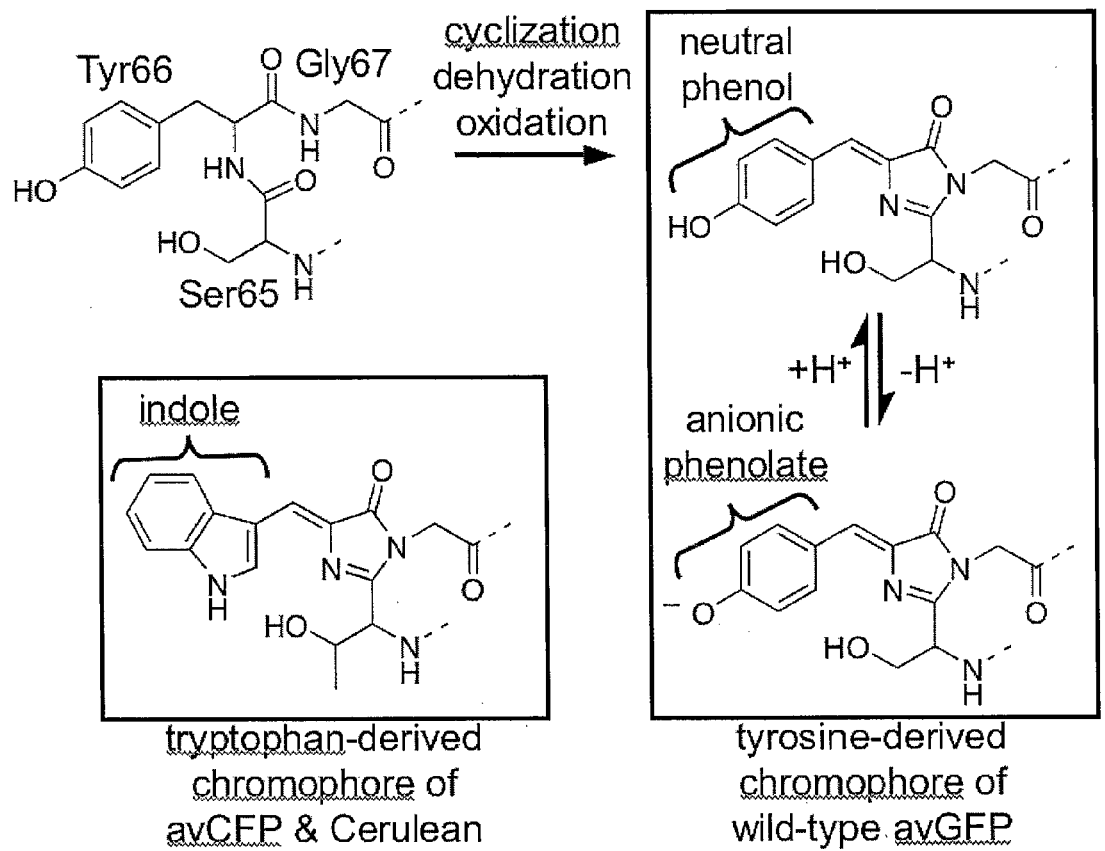
FIG. 1 (prior art) illustrates that, in wild-type avGFP, the green fluorescent chromophore arises from the post-translational modification of Ser65, Tyr66, and Gly67. The resulting chromophore contains either a neutral phenol or an anionic phenolate moiety. In avCFP and Cerulean, Tyr66 has been mutated to a tryptophan; thus, the resulting chromophore contains an indole moiety that is chemically distinct from either a phenol or phenolate group. TFP, a protein of the present invention, has a tyrosine-derived chromophore that differs from that of avGFP by the identity of the side chain at position 65, and the identity of the groups in near-spatial proximity to the fluorophore.
Figure 2:
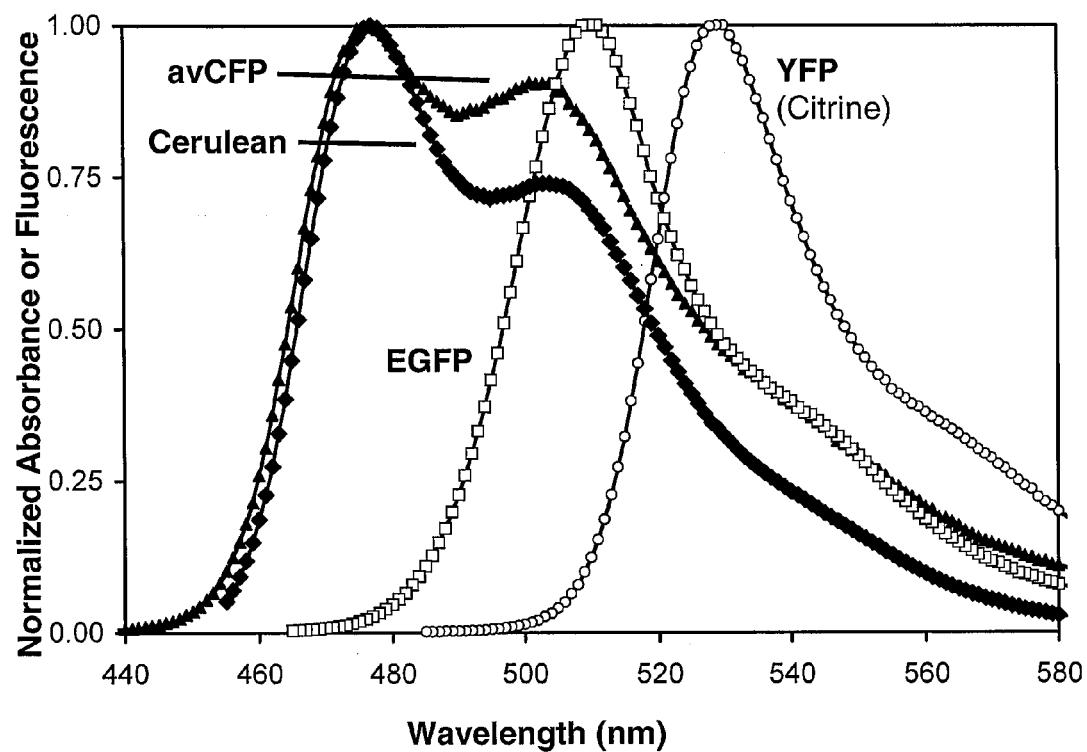
FIG. 2 (prior art) depicts the fluorescent emission spectra of avCFP, Cerulean, avGFP, and Citrine (a YFP). Note that both avCFP and Cerulean have strikingly broad emission peaks. A broad emission peak is undesirable when bandpass filters, which are typically used in fluorescence microscopy, are used to collect the fluorescence emission.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

Aspects of the present invention relate to novel proteins that fluoresce at cyan wavelength to create a variant that is optimized for use in fluorescence imaging. Three naturally occurring homologues of *Aequorea* GFP (cFP484 from *Clavularia* sp., amFP486 from *Anemonia majano*, and dsFP483 from *Discosoma striata*) with tyrosine-derived chromophores and emission peaks between ~480-490 nm that had been identified in coral (Matz, 1999) were initially considered.

As used herein, the terms "CFP" and "cyan fluorescent protein" refer to any GFP homologue with a fluorescence emission peak at less than or equal to 495 nm. As further used herein, a prefix is added to "CFP", when referring to CFPs from specific organisms, to indicate the name of the organism from which the gene encoding the protein was originally derived. As an example, as used herein, the term "cFP484" refers to a fluorescent protein ("FP") of the species *Clavularia* sp. ("c") with a major emission maximum of 484 nm. The term "TFP" or "teal fluorescent protein" refers to a CFP of the present invention, having a tyrosine derived chromophore.

To identify amino acid positions of a TFP, a numbering system is used in which the N-terminal residue is labeled 1, the second residue from the N-terminus is labeled 2, and so on until the last residue of the protein is reached at the C-terminus. If residues are added or deleted from the N-terminus of the protein, the identity of each subsequent residue could change if consistently numbered from the N-terminus. Therefore, employed herein, was a numbering system in which the residues of the chromophore-forming residues in the wild-type protein are glutamine 66, tyrosine 67, and glycine 68. Preceding and subsequent amino acids were labeled consistently with the chromophore numbering amino acids.

The naturally occurring homologues of *Aequorea* GFP mentioned above have emission peak shapes and fluorescent brightness comparable to *Aequorea* GFP and are likely tetramers and unsuitable for use as non-perturbing genetic labels (Campbell, 2002). In one example, the inventors chose cFP484 (International Application Publication No. WO0127150; Matz 1999) as the template from which to initiate directed evolution. cFP484 is a preferred starting point as it is the least divergent from a hypothetical 'consensus' sequence (FIG. 3); it has the highest fluorescent brightness; and it has a single cysteine residue while dsFP483 and amFP486 each have five (Matz, 1999).

To prepare proteins of the current invention, a fully-synthetic designed gene library with a theoretical diversity of $\sim 5 \times 10^5$ cFP484 variants (Table 1) was prepared; followed by screening. Such an approach has not been previously used for fluorescent proteins. In previous work, genes have been resynthesized with human codon usage. Libraries of gene variants have then been created by random mutation of the gene, or targeted diversification at specific positions within the gene.

Preferred features of the library included: mammalian codon usage, deletion of 40 non-homologous residues from the N-terminus, addition of the 7 N-terminal and 7 C-terminal residues of *Aequorea* GFP, semi-degenerate codons encoding potential 'tetramer-breaking' mutations at 3 external positions, and semi-degenerate codons encoding potential 'rescuing' mutations at 11 internal positions. Sequencing of random clones revealed that 12% of the genes had mutations only at desired positions and that the true library diversity was $\sim 4 \times 10^6$ variants. The library was used to transform *E. coli* and the resulting colonies were screened for fluorescence. Fluorescent colonies represented $\sim 0.5\%$ of all colonies and were approximately equally divided between colonies that fluoresced at $\sim 490$ nm and colonies that fluoresced at $\sim 510$ nm. The most brightly fluorescent protein identified after extensive screening was a dimer with 8 mutations relative to wild type and an emission peak at 486 nm.

These proteins have been described herein as 'teal fluorescent protein' (TFP), with a preceding 'd' for dimeric or 'm' for monomeric, and a succeeding numerical identifier, to identify variants described herein. Following this convention, the dimeric protein identified in the initial screen was designated dTFP0.1 and the 170% brighter version resulting from one round of directed evolution was designated dTFP0.2 (Table 2 and 3). Substitution of dimer interface residues Ser162 and Ser164 with lysine produced a monomeric version (FIG. 4), mTFP0.3, which retained only 15% of the brightness of its dimeric precursor. After multiple successive rounds of screening libraries (generated by random or saturation mutagenesis) for variants with improved brightness and high 480/530 nm emission ratio, mTFP0.7 was obtained that had a fluorescent brightness equivalent to Cerulean (Table 2). However, imaging an mTFP0.7-actin fusion in live HeLa cells by confocal microscopy, led to a fluorescent signal that rapidly vanished upon illumination with the 458 nm laser, due to a rapid in vitro photo-conversion to a non fluorescent state (Table 2 and 3).

TABLE 1

Rationale for design of the synthetic gene library

| Residue number | Mutated to | Codon | Rationale |
|---|---|---|---|
| His42 | His, Asn, Gln, Lys | MAS | Mutations beneficial to tetrameric DsRed variants (Bevis, 2002). Not conserved in coral CFPs. |
| Leu44 | Leu, Val, Ala, Pro | SYC | Mutations beneficial to tetrameric DsRed variants (Bevis, 2002). Not conserved in coral CFPs. |
| Gln66 (residue of chromophore) | Gln, Lys, Met, Leu | MWG | Mutations beneficial to *Aequorea* GFP (Heim, 1995) and monomeric RFPs (Shaner, 2004). Lys or Gln present in coral CFPs. |
| Arg70 | Lys, Arg | ARG | Mutations beneficial to monomeric RFPs (Campbell, 2002). Lys or Arg present in coral CFPs. |
| Ala71 | Ala, Val | GYC | Mutations beneficial to monomeric RFPs (Campbell, 2002). Ala or Cys present in coral CFPs. |
| Leu72 | Leu, Phe, Ile | HTC | Phe in 2 coral CFPs and Leu in 1 coral CFP. |
| Phe83 | Leu, Phe, Ile | HTC | Mutations beneficial to monomeric RFPs (Campbell, 2002; Shaner, 2004). Phe in 2 coral CFPs and Leu in 1 coral CFP. |
| Ile104 | Ile, Thr | AYC | May disrupt A-B interface interactions |
| Phe124 | Leu, Phe, Ile | HTC | Mutations beneficial to dimeric RFPs (Campbell, 2002). Strict conservation in coral CFPs. |
| Asp125 | Lys, Arg | ARG | Likely to disrupt A-B interface interactions. |
| Met127 | Lys, Arg | ARG | Likely to disrupt A-B interface interactions. |
| Met150 | Met, Leu | MTG | Mutations beneficial to monomeric RFPs (Campbell, 2002). Met in 2 coral CFPs and Leu in 1 coral CFP. |
| His163 | His, Gln | CAS | Mutations beneficial to dimeric and monomeric RFPs (Campbell, 2002; Shaner, 2004). His in 2 coral CFPs and Ala in 1 coral CFP. |
| Ser179 | Ser, Thr | WCC | Mutations beneficial to dimeric RFPs (Campbell, 2002). Thr in 2 coral CFPs and Ser in 1 coral CFP. |

TABLE 2

Fluorescent properties of CFPs and TFPs.

| Protein | Absorbance (nm) | Emission (nm) | $\epsilon^a * 10^{-3}$ (mM$^{-1}$cm$^{-1}$) | $\phi^b$ | Brightness$^c$ (mM$^{-1}$cm$^{-1}$) | pKa | Photo-stability$^d$ | Cameleon FRET efficiency (+/−Ca$^{2+}$) − | Cameleon FRET efficiency (+/−Ca$^{2+}$) + |
|---|---|---|---|---|---|---|---|---|---|
| cFP484$^e$ | 456 | 484 | 35.3 | 0.48 | 17 | ND$^f$ | ND | ND | ND |
| dTFP0.1 | 456 | 485 | 42 | 0.63 | 26 | ND | <1 | ND | ND |
| dTFP0.2 | 456 | 486 | 60 | 0.68 | 41 | ND | <1 | ND | ND |
| mTFP0.3 | 458 | 488 | 19 | 0.31 | 6 | ND | <1 | ND | ND |
| mTFP0.7 | 453 | 488 | 60 | 0.50 | 30 | 4.0 | <1 | ND | ND |
| mTFP1 | 462 | 492 | 64 | 0.85 | 54 | 4.3 | 163$^g$/110$^h$ | 39% | 49% |
| mECFP | 433/451$^i$ | 475/504$^i$ | 33/30$^i$ | 0.41 | 13/12$^i$ | 4.7 | 64$^{h,j}$ | 26% | 39% |
| mCerulean | 433/451$^i$ | 475/503$^i$ | 43/37$^i$ | 0.64 | 27/24$^i$ | 4.7 | 36$^{g,j}$ | 30% | 41% |
| mTFP1-Y67W | 424/440$^i$ | 461/482$^i$ | 13 | 0.02 | 0.3 | ND | ND | ND | ND |
| mTFP1-Y67H | 369$^k$ | NA | 7 | NA | NA | ND | NA | ND | ND |
| G1 | 487 | 503 | 43 | 0.60 | 26 | ND | ND | ND | ND |
| G2 | 487 | 503 | 60 | 0.65 | 39 | ND | 65 | ND | ND |
| G3 | 498 | 515 | 70 | 0.70 | 49 | ND | 5.5 | ND | ND |
| EGFP$^j$ | 488 | 507 | 56 | 0.60 | 34 | 6 | 174$^{h,j}$ | ND | ND |
| tdTFP0.3 | 458 | 489 | 125 | 0.69 | 86 | ND | ND | ND | ND |
| Emerald$^j$ | 487 | 509 | 57.5 | 0.68 | 39 | 6 | 0.69 | ND | ND |
| mWasabi | 493 | 509 | 70 | 0.8 | 56 | 6.5 | 93$^h$ | ND | ND |

$^a$Extinction coefficient.
$^b$Quantum yield.
$^c$Product of $\phi$ and $\epsilon*10^{-3}$. Values for common FP variants have been previously tabulated (Shaner, 2005).
$^d$Time to bleach from an initial emission rate of 1000 photons/s to 500 photons/s.
$^e$Values from ref. (Matz, 1999).
$^f$Not determined.
$^g$Measured with 10% ND filters.
$^h$Measured with no ND filters.
$^i$Values for both 'humps' of mECFP, mCerulean and mTFP1-Y67W are provided.
$^j$Values from ref. (Shaner, 2005).
$^k$This value is the absorption maximum. No significant fluorescence was detected for mTFP1-Y67H.

TABLE 3

Mutations in dimeric and monomeric TFP variants.

| Variant | Library construction strategies | Mutations |
|---|---|---|
| dTFP0.1 | See Supplementary Table 1. | Inside: H42N, L44V, L72F, F124L, M150L, S179T<br>A-B interface: D125K, M127K |
| dTFP0.2 | 2 generations of random mutagenesis. | Inside: D81N<br>Outside: S226P |
| mTFP0.3 | Site-directed mutagenesis at 162 and 164. Saturation mutagenesis at 163. | A-C interface: S162K, S164K |
| mTFP0.4 | Saturation mutagenesis at 66. Semi-saturation mutagenesis at 175. | Inside: Q66C, C175V |
| mTFP0.5 | 3 generations of random mutagenesis. | Inside: S62T, C66G<br>Outside: A80P, N216S<br>A-B interface: K127E, K182R |
| mTFP0.6 | Saturation mutagenesis at 66 + 163, 66 + 197. Semi-saturation mutagenesis at 66 + 147, 66 + 213. | Inside: G66A, L213V<br>Outside: S2N<br>Replace 223-228 with TG |
| mTFP0.7 | 2 generations of random mutagenesis. | Inside: V44I, Y173H<br>Outside: V186A<br>A-B interface: R123H<br>Mutate: N2S |
| mTFP0.8 | Semi-saturation mutagenesis at 62, 63, 64, 65, and 66 with screening for photostability. | Inside: N63T |
| mTFP0.9 | Semi-saturation mutagenesis at 142, 144, 145, 149, 150, and 161 with screening for photostability. | Inside: K142G, L150M (reversion to wild type), I161V<br>A-C interface: E144D, P145A, I149R |
| mTFP1 | 2 generations of random mutagenesis with screening for photostability. | Outside: L141T, V158K, Y221N, G224D |
| G1 | Saturation mutagenesis at 163. | mTFP1-H163M |
| G2 | Random mutagenesis | mTFP1-K139E/H163M |
| G3 | Random mutagenesis | mTFP1-T73A/K139E/H163M |
| G2.1 | Saturation mutagenesis at 66, 161, 199 | mTFP1-A66S/K139E/H163M |
| mWasabi | Random mutagenesis | mTFP1-A66S/K139E/H163M/S216I |

To select for photostable variants, an array of six 460 nm light emitting diodes (Lumileds, San Jose, Calif.) was constructed that provided even illumination of a Petri dish with ~55 mW/cm$^2$; an irradiance that is 1400× more intense than the excitation used in previous screening and sufficient to photoconvert mTFP0.7 within seconds. The fluorescence of libraries of mTFP0.7 variants expressed in bacterial colonies was digitally imaged during exposure to intense illumination and colonies with decreased propensity to photoconvert were identified. Following several rounds of selection for variants that were photostable, bright, and retained a high 480/530 nm emission ratio, we arrived at mTFP1 that has a total of 29 mutations relative to wild type protein. In addition, mTFP1 is 2-fold brighter and more photostable than Cerulean and is insensitive to physiologically relevant changes in pH (Table 2 and FIGS. 5 and 6).

To determine the photostability of mTFP1, photobleaching experiments were done on droplets of purified protein suspended in mineral oil following the protocol of Shaner et al. (2005). This method is designed to approximate the conditions of a typical wide-field microscopy experiment while rigorously accounting for differences in the spectral properties of the fluorescent proteins as well as the optical properties of the microscope. Using this method, the time for bleaching from an initial emission rate of 1,000 photons/sec/molecule down to 500 photons/sec/molecule (t1/2) was determined to be 163 s when 10% neutral density filters were used. With no neutral density filters, the t1/2 was 110 s for mTFP1. For the sake of comparison, the t1/2 for Cerulean with 10% neutral density filters is 36 s and the t1/2 for EGFP with no neutral density filters is 174 s (Shaner, 2005). As previously described herein (Shaner, 2005), Cerulean displays an illumination intensity-dependent fast bleaching component that can decrease the intensity to 60% of its initial value within the first few seconds of imaging under typical conditions (Shaner, 2005 and P. Steinbach, personal communication). No fast bleaching component was observed for mTFP1.

Expression of mTFP1-actin fusion in mammalian cells was performed to demonstrate its suitability for use as non-perturbing fusion partner (FIG. 7). The fusion protein localized correctly and there was no significant decrease in intensity upon illumination with the 458 nm laser.

Typical fluorescence filter sets used to image Cerulean are adequate but suboptimal for mTFP1. In one embodiment, to take advantage of mTFP1's improved brightness, a 445/30 nm excitation filter, a 470 nm beamsplitter, and a 495/30 nm emission filter may be used (FIG. 7B and Table 4). This combination gives a 2.6-fold increase in fluorescent signal relative to mCerulean imaged using a standard CFP set (e.g. a 436/20 nm excitation filter, a 455 nm beamsplitter, and a 480/40 nm excitation filter). This preferred set has been used in combination with a new YFP emission filter (545/30=n), to demonstrate that mTFP1-YC3.3 can be practically employed in live cell FRET imaging. The gene encoding mTFP1-YC3.3 was cloned into a mammalian expression vector with an N-terminal signal sequence and a C-terminal endoplasmic reticulum (ER) retention peptide (Miyawaki, 1997). FRET imaging of transiently transfected HeLa cells on an Zeiss Axiovert 200M equipped with a digital CCD camera revealed a typical pattern of endoplasmic reticulum localization and robust ratiometric responses to induced changes in the free $Ca^{2+}$ concentration. This result demonstrates that the spectral distinction between mTFP1 and mCitrine are sufficient for these proteins to be used as an advantageous new FRET pair that can be imaged on a standard epifluorescence microscope equipped with appropriate bandpass filter sets.

TABLE 4

Experimentally determined relative fluorescence intensities for identical concentrations of mTFP1, mCerulean, and mCitrine imaged on an epi-fluorescence microscope with xenon arc lamp illumination.

| | | | Intensity relative to mCerulean imaged with a HQ436/20 excitation filter and D480/40 emission filter[a] | |
|---|---|---|---|---|
| | Excitation | | | |
| Protein | filter[a] | Beamsplitter[a] | D480/40 | HQ495/30 |
| mTFP1 | D436/20 | 455DCLP | 1.3 | 1.5 |
| | HQ445/30 | 470DCXR | ND[b] | 2.6 |
| mCerulean | D436/20 | 455DCLP | 1.0 | 0.8 |
| | HQ445/30 | 470DCXR | ND[b] | 1.3 |

| | | | | Relative intensity passed by YFP emission filter[a,c] | |
|---|---|---|---|---|---|
| | Excitation | | TFP or CFP | | |
| Protein | filter[a] | Beamsplitter[a] | emission filter[a] | HQ535/30 | HQ545/30 |
| mTFP1 | D436/20 | 455DCLP | HQ495/30 | 0.39 | 0.30 |
| | HQ445/30 | 470DCXR | HQ495/30 | 0.39 | 0.30 |
| mCerulean | D436/20 | 455DCLP | D480/40 | 0.35 | 0.30 |
| | HQ445/30 | 470DCXR | HQ495/30 | 0.41 | 0.34 |
| mCitrine | HQ500/20 | Q515LP | ND[b] | 1 | 0.91 |
| | D436/20 | 455DCLP | ND[b] | 0.12 | 0.07 |
| | HQ445/30 | 470DCXR | ND[b] | 0.15 | 0.09 |

[a]All filters and beamsplitters were purchased from Chroma Technology Corp. Filters are designated with Chroma part numbers.
[b]Not determined.
[c]For mTFP1 and mCerulean, intensities are relative to the intensity in the indicated TFP or CFP emission channel. For mCitrine, all intensities are relative to the intensity obtained with a HQ500/20 excitation filter and HQ535/30 emission filter.

mTFP1's suitability as a FRET donor to Citrine was also demonstrated. Analogous versions of yellow Cameleon 3.3 (YC3.3) containing either mECFP, mCerulean, or mTFP1 were constructed and their FRET efficiency in the absence and presence of $Ca^{2+}$ was determined (Table 2). FRET efficiencies were accurately determined by trypsinolysis under conditions where the fluorescent proteins themselves remain intact but the calmodulin-M13 domain is cleaved. FRET efficiencies (E) for mECFP and mCerulean in Table 2 were calculated using the formula E=1−(fluorescence at 475 nm before trypsinization/fluorescence at 475 nm after trypsinization). For mTFP1, the fluorescence before and after trypsinization was measured at 490 nm. All three reporters increased FRET efficiency upon $Ca^{2+}$-binding but the mTFP1 version was notable for its significantly higher efficiencies in both the $Ca^{2+}$-bound and $Ca^{2+}$-free states. The trend in experimental FRET efficiencies, mECFP<mCerulean<mTFP1, is consistent with our calculated Ro values of 5.0 nm for mECFP, 5.3 nm for mCerulean, and 5.7 nm for mTFP1. It is important to note that the original YC3.3 contained ECFP and had been optimized for maximum FRET difference between the $Ca^{2+}$-bound and $Ca^{2+}$-free states. It is therefore unsurprising that switching to an mTFP1 donor (with a different dipole orientation and increased Ro value) results in a slightly decreased dynamic range. This is almost certainly because the protein was empirically optimized (Miyawaki, 1997 and 2000) for interfluorophore distance changes centered on the Ro of ECFP (where there is the strongest dependence of FRET efficiency on distance). It is believed that if mTFP1-YC3.3 was to be subject to similar systematic optimization, the dynamic range will be significantly improved.

The utility of mTFP1 for use in fluorescence lifetime imaging (FLIM) was demonstrated by measuring the fluorescence lifetimes of mECFP, mCerulean, and mTFP1 under identical in vitro conditions (FIG. 8). In contrast to mCerulean, which is best described as a poor fit of a single lifetime (Rizzo, 2004), mTFP1 is unambiguously best fit as single lifetime ($\tau=3.3$ ns, $\chi2=1.1$). Attempts to fit the mTFP1 lifetime decay data with a double exponential converged to solution in which $\tau1=\tau2=3.2$ ns; strong evidence for the single fluorescent lifetime. Repeating the experiment under 'magic angle' conditions had no effect on the observed lifetimes or statistics. Analogous experiments with mECFP and mCerulean resulted in data that was best fit as double exponentials (for mECFP $\tau1=3.7$ ns (80%), $\tau2=1.7$ ns (20%), $\chi2=1.1$; for mCerulean $\tau1=3.7$ ns (80%), $\tau2=1.9$ ns (20%), $\chi2=0.99$). As previously reported (Rizzo, 2004), mCerulean could also be adequately fit with a single exponential ($\tau=3.5$ ns, $\chi2=1.1$), though the residuals were consistently unsatisfactory.

The approach described herein is advantageous in that it permits the discovery of mutants with combinations of mutations that are only beneficial when they occur together. Such variants could not be discovered by a stepwise approach, since it is possible that the individual mutations are not beneficial (or might even be detrimental) by themselves. For example, dTFP0.1 contains six mutations (H42N, L44V, L72F, F124L, M150L, S179T) in the interior of the protein. Through the use of random mutagenesis, such a combination of mutations would be so exceptionally rare that it would never be discovered by any sort of conventional library screening procedure. In addition, even six rounds of random mutagenesis (with an average of one mutation per gene in each round) would probably not lead to this same variant, unless each mutation in isolation resulted in an improvement.

The engineered proteins described herein differ from the wild-type protein in a number of respects. For example, the proteins of the present invention are dimers or monomers, and are brighter than the wild-type protein. The proteins also lack the first forty amino acids of cFP484, and the long N-terminal sequence of cFP484. Furthermore, the monomeric versions of TFP described herein lack the last six amino acids of cFP484. The corresponding sequences of *Aequorea* GFP have been appended to the N- and C-termini of the TFP variants.

The chromophore of cFP484, from which the monomers of the present invention were ultimately derived, was obtained from the amino acid sequence glutamine-tyrosine-glycine (QYG). The tyrosine and glycine are absolutely essential, and are present in all naturally-occurring fluorescent proteins of all colors. The preceding residue, glutamine, is also very important, but tends to vary among different colors. Nevertheless, different proteins of the same color can have different residues at this position. For example, the other two naturally-occurring cyan fluorescent proteins have a glutamine at this position. In certain of the monomers of the present invention, mutations have been introduced at this position, and particular residues have been found to be preferable to the wild-type glutamine residue. By way of example, mTFP0.4 has a cysteine, mTFP0.5 has a glycine, and mTFP0.1 has an alanine.

Tryptophan residues located in the vicinity of the chromophore sequence do not have a particular significance with respect to the chromophore structure. The engineered cyan fluorescent proteins, avCFP and Cerulean, have a chromophore structure that is derived from the sequence threonine-tryptophan-glycine.

The proteins of the present invention are advantageous, relative to cFP484, in that: (1) they are dimers or monomers; (2) they have a higher extinction coefficient; (3) they have a higher quantum yield; (4) they have mammalian codon usage; (5) high brightness; (6) improved photostability; (7) efficient intra- and inter-molecular FRET with a yellow or orange acceptor fluorescence protein; (8) dual color imaging in combination with an orange or red fluorescent protein and (9) a single fluorescence lifetime. For dual color imaging in combination with a YFP, mTFP1 could provide a brighter fluorescent signal than existing *Aequorea*-derived CFPs but the bleedthrough into the acceptor emission channel may be only slightly better (or possibly worse) depending on the specific filter combination in place. In addition, these proteins have N- and C-terminal sequences corresponding to the N- and C-terminal sequences of *Aequorea* GFP. This facilitates subcloning, since any DNA primer that can be used to perform PCR on the widely-available *Aequorea* GFP will also work with the TFPs of the present invention. These proteins are also optimized for expression at 37° C., and may have lower toxicity to live cells. Furthermore, these proteins have a narrow emission peak; this is advantageous, relative to *Aequorea*-derived CFP. It is believed that these proteins will be useful in research, particularly in the areas of cell biology, physiology, oncology, and biochemistry.

In view of the foregoing, the present invention provides an isolated nucleic acid composition comprising a nucleic acid sequence encoding a non-oligomerizing *Clavularia* teal fluorescent protein (TFP) variant having a tyrosine-derived chromophore. Also provided is any fragment or derivative of the isolated nucleic acid composition of the invention. The complete DNA sequence of *Clavularia* sp. fluorescent protein FP484 may be obtained from GenBank Accession No. AF168424.

The recently reported crystal structure of amFP486 revealed the presence of a positively charged histidine near the chromophore that may limit charge transfer in the excited state and thereby give rise to the blue-shift Arg70, Glu148, His197, and Glu215. Without being bound by a theory, it is likely that the Arg/Lys degeneracy at position 70 was responsible for the 50/50 split between green and cyan FPs in the initial library.

Additional mutagenesis experiments indicate that particular amino acids dictate the color of the mTFP1 chromophore. Two histidine residues (His163 and His197), which are in close proximity to the chromophore, are approximately equal determinants of the blue shifted fluorescence emission of mTFP1.

Figure 23:
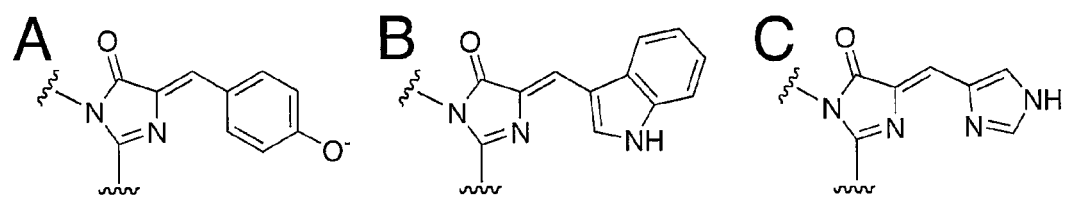
FIG. 23 shows the chromophore structures of mTFP1 and its hue-shifted variants: (A) the chromophore structure shared by EGFP, mTFP1, and mWasabi, (B) the chromophore structure shared by ECFP and the mTFP1-Y67W variant, (C) the chromophore structure shared by EBFP and the mTFP1-Y67H variant.
Figure 24:
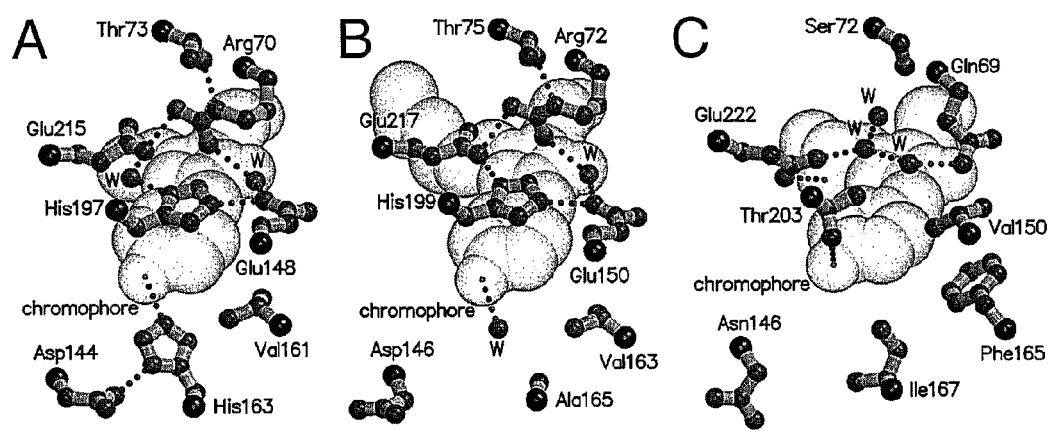
FIG. 24 shows the chromophore environment of mTFP1, amFP486, and avGFP-S65T: (A) Shown in space filling representation is the chromophore of mTFP1 (Protein data bank code 2HQK (Ai et al., 2006). The side chains of residues in close proximity to the chromophore are shown in ball-and-stick. Hydrogen bonds are indicated with black dotted lines. Cα for each residue is represented as a black sphere. Atoms labeled 'W' are ordered water molecules. (B) The chromophore environment of amFP486 showing the residues that are structurally aligned with the residues represented in (A) (PDB code 2A46) (Henderson et al., 2005). (C) The chromophore environment of avGFP-S65T (and EGFP) showing the residues that structurally align with those represented in (A). (PDB code 1EMA) (Ormo et al., 1996). avGFP-S65T and EGFP differ only by the Phe64Leu mutation which does not significantly modify the conformation of any residues shown in this figure.

Computational studies support the idea that there is a partial transfer of charge from the phenolate moiety to the imidazolinone moiety (FIG. 23A) in the excited state of the avGFP anion (Cinelli et al., 2001; Marques et al., 2003). Since the phenolate is more electron rich in the ground state than in the excited state, factors that contribute charge stabilization tend to increase the energy barrier for charge transfer and shift the excitation and emission peaks to higher energy wavelengths (i.e. towards the blue). The crystal structures of mTFP1 (Ai et al., 2006) and amFP486 (a tetrameric cyan-fluorescing fluorescent protein from *Anemonia majano*) (Henderson et al., 2005) revealed that these homologous blue shifted fluorescent proteins both have a cationic His imidazole (His197 of mTFP1, His199 of amFP486) stacked against the phenolate ring of the chromophore (FIGS. 24A and 24B). Based on a simple electrostatic interpretation of this interaction, this additional positive charge should stabilize the anionic character of the phenolate ring. Other mutagenesis-based studies indicate that the side chain of the residue aligning with residue His163 of mTFP1, or a buried water molecule that occupies the cavity when the side chain is small (as is the case of Ala165 in amFP486 as shown in FIG. 24B), also has an important role in stabilizing anionic character on the phenolate ring (Gurskaya et al., 2001). Henderson et al. (2005) have proposed that the electrostatic interaction with His199 is of greater significance than the interaction with the water molecule in the residue 165 side chain cavity for causing the blue shifted emission of the amFP486 chromophore. The relative importance of His197 and His163 with respect to the blue shift of the mTFP1 chromophore has not been investigated.

If this electrostatic-based mechanism for 'fine tuning' of the emission wavelength is indeed operative in mTFP1, variants with alternative chromophore structures should also be blue shifted relative to their avGFP analogues. Two qualifications are that formation of the excited state still involves charge transfer to the imidazolinone ring and that significant repacking of the side chains lining the chromophore-containing cavity does not occur with the new chromophore structure. Therefore, Tyr67Trp and Tyr67His mutants of mTFP1 were created to investigate if this mechanism for blue shifting the fluorescence could be translated to alternative chromophore structures. The chromophore structures of mTFP1-Y67W and mTFP1-Y67H are chemically identical to that of avGFP-derived ECFP and EBFP, respectively (FIGS. 23B and 23C). Accordingly, the inventors expected that the absorbance and fluorescence emission maxima of mTFP1-Y67W and ECFP (and mTFP1-Y67H and EBFP) would be similar but not necessarily identical. If differences between the spectra of the two proteins were observed, they must be attributable to the effect of the protein environment on the chromophore.

Figure 25:
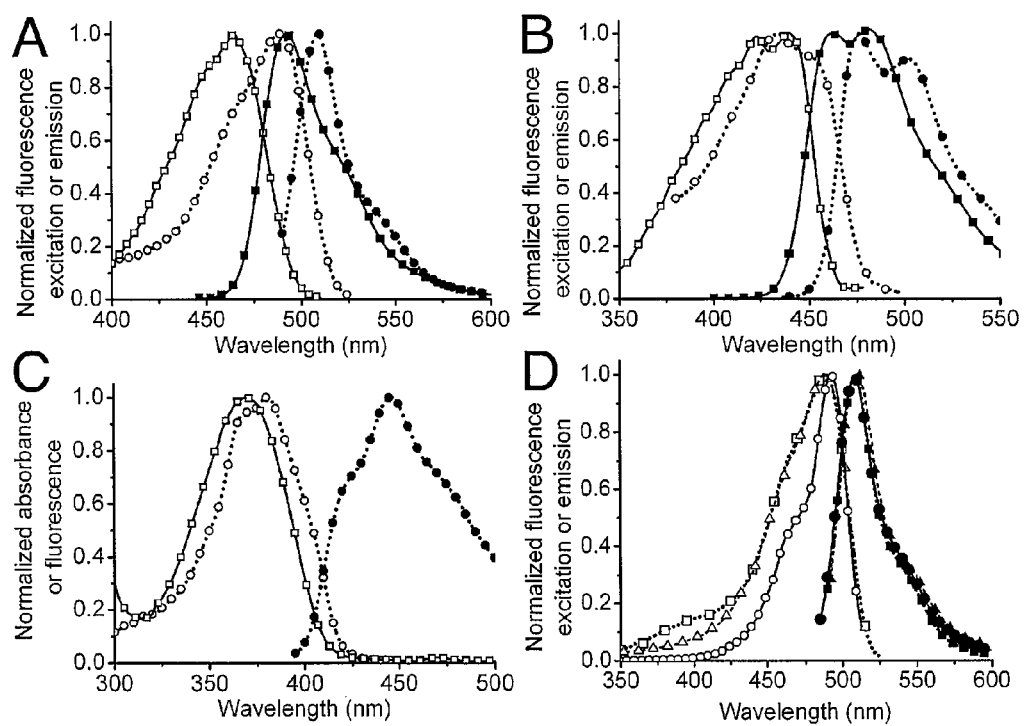
FIG. 25 shows the spectra of hue-shifted variants of mTFP1: (A) Excitation (open symbols) and emission (filled symbols) spectra of EGFP (circle) and mTFP1 (square). (B) Excitation (open symbols) and emission (filled symbols) spectra of ECFP (circle) and mTFP1-Y67W (square). (C) Excitation (open symbols) and emission (filled symbols) spectra of EBFP (circle) and the absorbance (open symbols) spectrum of the nonfluorescent mTFP1-Y67H variant (square). (D) Excitation (open symbols) and emission (filled symbols) spectra of mWasabi (circle), EGFP (square) and Emerald (triangle). Spectra were collected at 1 nm steps, but only every 5th data point is shown for clarity.

Measuring the absorbance and emission spectra of purified mTFP1-Y67W revealed that this protein is fluorescent, exhibits the typical double-humped peaks associated with a tryptophan-derived chromophore, and is 15 nm blue shifted relative to EGFP (FIG. 24B and Table 1). The purified mTFP1-Y67H variant exhibited no significant fluorescence, but did have a strong absorbance peak that was blue shifted by 20 nm relative to avGFP-derived EBFP (FIG. 25C and Table 1). The protein-chromophore interactions responsible for blue shifting the absorbance and emission maxima (i.e. raising the energy of the excited state) of mTFP1 are thus not intrinsically dependent on the presence of a tyrosine-derived chromophore. In the crystal structure of mTFP1, the doubly protonated imidazole of His163 makes a hydrogen bond with the phenolate oxygen of the chromophore (FIG. 24A). An analogous interaction is not possible in the mTFP1-Y67H or mTFP1-Y67W variants. In contrast, the close stacking of the His197 imidazole against the chromophore phenolate is an interaction that could be preserved in the mTFP1-Y67W or mTFP1-Y67H variants. The hydrogen bond with His163 does not appear to be significant with respect to the blue shift of mTFP1 and it is either the close stacking of the His197 imidazole and/or a hydrogen bond-independent electrostatic effect of His163 that is responsible for the blue shift.

In order to ascertain the relative importance of His163 and His197 in blue shifting mTFP1 fluorescence, variants were examined in which the identity of one residue is changed through the use of site-directed mutagenesis. His199 of amFP486, which is structurally analogous to His197 of mTFP1, is stacked against the chromophore and has multiple critical roles that dictate the spectroscopic properties (FIG. 24B) (Henderson et al., 2005). Since this might have made interpretation of the effects of mutation at this position challenging, the inventors focused on His163 since it is not strictly conserved between the natural cyan-fluorescing proteins and thus less likely to have multiple critical roles. Saturation mutagenesis of mTFP1 at position 163 was performed and the library was screened using a colony-based fluorescence imaging system. Screening revealed that the library contained both brightly cyan-fluorescing and green-fluorescing members. DNA sequencing revealed that the bright cyan-fluorescing members of the library had a histidine at position 163 and were thus identical to mTFP1. The brightest green-fluorescing member had a methionine at position 163 and a fluorescence emission maximum at 503 nm (Table 1). The fact that the emission maximum of mTFP1-H163M is 11 nm red shifted from that of mTFP1 provides strong support for His163 contributing to the blue shift of the mTFP1 chromophore by an electrostatic mechanism.

It was investigated whether His163 is solely responsible for the blue shift of mTFP1 or if His197 also plays a role. One would need to determine the fluorescence emission maximum of mTFP1 in the absence of the electrostatic effects due to the proximity of charged His163 and His197. The emission maximum of EGFP had been used as a reference point for the default emission of the tyrosine-derived chromophore. However, there are a number of differences between the chromophore containing cavities of EGFP and mTFP1 (Henderson et al., 2005), the most important being the presence of His197 in mTFP1 (compare FIGS. 24A and 24C). A threonine residue occupies the structurally analogous position 203 in EGFP (Ormo et al., 1996) and it is well established that substituting aromatic amino acids at this position results in red shifted fluorescence emission due to a π-stacking interaction with the chromophore (Heim et al., 1996). It has previously been reported that the Thr203His mutant has a fluorescence emission at 517 nm when excited at 475 nm (Patterson et al., 2002). Unlike the positively charged imidazole of His197 in mTFP1, the imidazole of His203 in EGFP-T203His expected to be in the neutral charge state. Based on this comparison with EGFP variants, a value of approximately 517 nm was selected as the default emission maximum for the mTFP1 chromophore in the absence of electrostatic interactions with His163 and His197.

It was found that the Thr73Ala substitution red shifts the fluorescence of mTFP1-K139E/H163M from 503 nm to 515 nm. In the crystal structure of mTFP1, the hydroxyl group of Thr73 is hydrogen-bonded to the guanidium group of Arg70: the key participant of the salt-bridge network (Arg70/Glu148/Glu215/His197) responsible for maintaining the imidazole of His197 in the positively charge state (FIG. 24A). The loss of the Thr73-Arg70 hydrogen bond in the Thr73Ala mutant perturbs the salt-bridge network and results in formation of a neutral His197 imidazole. This conclusion is supported by the very similar emission maxima of 517 nm and 515 nm observed for EGFP-T203H and mTFP1-T73A/K139E/H163M, respectively. The Thr73Ala mutant effectively separates the electrostatic role of His197 from its additional roles in maintaining the chromophore environment and reveals that the electrostatic effect accounts for a blue shift of 12 nm. This mutagenesis-based study supports the conclusion that His163 and His197 act in concert to blue shift the fluorescence emission of the mTFP1 chromophore through an electrostatic mechanism. The contribution of both residues is effectively identical with 11 nm and 12 nm of blue shift attributed to His163 and His197 respectively.

The mTFP1-H163M (designated G1) template was subjected to directed evolution to create a new green fluorescent protein variant. Error-prone PCR was used to create libraries of genetic variants, the gene libraries were expressed in *E. coli*, and colonies were screened for bright green fluorescence. The brightest green fluorescent colony identified in the first round of screening was found to express a G1 variant with additional mutation Lys139Met (designated G2). This variant was used as the template for a second round of library construction and screening. The brightest variant identified in the second round was mTFP1-T73A/K139M/H163M (designated G3). No further improvements were identified during a third round of screening of randomly mutated variants based on the G3 template. In vitro characterization revealed that relative fluorescent brightness to be 1, 1.5, and 1.9 for G1, G2, and G3, respectively. While both G1 and G2 had fluorescence maxima at 503 nm, G3 was further red shifted to 515 nm.

Further investigation of the G2 and G3 variants revealed that the dimer G2 was 11.8-fold more photostable than the brighter G3 variant. Optimization was conducted based on the G2 template. Saturation mutagenesis at 3 positions chosen based on their proximity to the chromophore (Ala66, Val161, and Ile199) resulted in the identification of a further improved variant containing the Ala66Ser substitution. A subsequent round of random mutagenesis resulted in the identification of the Ser216Ile substitution. Additional rounds of random mutagenesis yielded no further improvements.

The end product designated "mWasabi" is a green fluorescent protein equivalent to mTFP1-A66S/K139E/H163M/S216I. The fluorescence emission maximum of mWasabi is intermediate between that of G1 and G3, suggesting that there has been a perturbation of the salt-bridge network. It has been previously reported that avGFP with a Ser at residue 65 is 5 nm red shifted from avGFP with an Ala at residue 65 (Heim et al., 1996). As observed in the avGFP-S65T structure (FIG. 25C), the hydroxyl group of the Ser at residue 66 of mWasabi could potentially form a new hydrogen bond with Glu215 and partially disrupted its ability to contribute to the critical salt-bridge network.

Therefore, in one embodiment, the invention comprises mTFP1 having at least one of the following additional mutations: alanine 66 replaced with serine; lysine 139 replaced with glutamic acid; histidine 163 replaced with methionine; and serine 216 replaced with isoleucine. In a preferred embodiment, the variant comprises all four further mutations (mWasabi), resulting in the amino acid sequence of SEQ ID NO: 20. The mWasabi TFP variant has a total of four amino acid substitutions relative to mTFP1 (SEQ ID NO: 7). mWasabi includes a tyrosine-derived chromophore polypeptide comprising an amino acid sequence of serine-tyrosine-glycine (SYG).

The present invention also provides a nucleic acid sequence encoding mWasabi comprising the nucleic acid sequence of SEQ ID NO: 19 (Genbank Accession EU024648).

mWasabi is a highly fluorescent species sharing similar advantageous properties as mTFP1, including a high extinction coefficient and high quantum yield, which contribute to a fluorescent brightness equivalent to that of mTFP1 (56 $mM^{-1}cm^{-1}$ for mWasabi compared to 54 $mM^{-1}cm^{-1}$ for mTFP1, Table 1). The photostability of mWasabi was determined using the protocol of Shaner et al. (2005) as previously described. The time for bleaching from an initial emission rate of 1,000 photons/sec/molecule to 500 photons/sec/molecule ($t^{1/2}$) was determined to be 93 s. mWasabi thus has sufficient photostability to enable time-lapse imaging over a lengthy duration.

mWasabi has an absorbance at 493 nm and an emission at 509 nm, thereby emitting in the green spectral region and taking it outside of the definition of a CFP or TFP. However, for the purposes of the present application, mWasabi is considered to be a TFP variant, as it was developed directly from a TFP variant, mTFP1. The conversion of mTFP1 into mWasabi via four mutations surprisingly shifts the emission from 492 nm to 509 nm. EGFP derived from *Aequorea* GFP (SEQ ID NO: 13) and Emerald Green Fluorescent Protein derived from the *Aequorea victoria* jellyfish (Tsien, 1998) are well known green-emitting proteins. EGFP is hampered by a lower extinction coefficient and lower quantum yield, hence lower overall brightness compared to mWasabi which is 1.6-fold brighter than EGFP. Emerald has an extremely rapid photobleaching component which may adversely affect quantitative imaging (Shaner, 2005).

Figure 26:
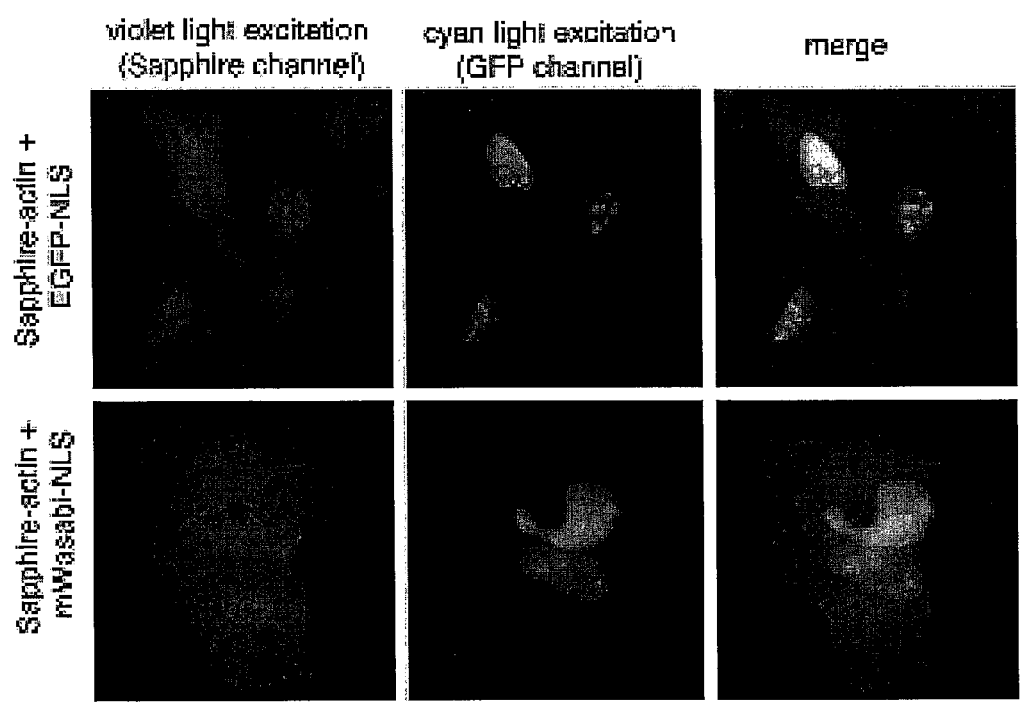
FIG. 26 shows two color imaging with Sapphire/EGFP and Sapphire/mWasabi. Shown in the upper row of panels are HeLa cells that have been transfected with plasmids for expression of both Sapphire-actin and EGFP-NLS. Shown in the lower row of panels are identically treated HeLa cells expressing Sapphire-actin and mWasabi-NLS.

EGFP and its descendents have their major absorption peaks at approximately 488 nm (Cubitt et al., 1999; Waldo et al., 1999; and Pedelacq et al., 2006). However, due to the breadth of this peak and the fact that in some variants a significant fraction of the protein exists as the UV-excitable neutral chromophore, EGFP and related variants are efficiently excited with violet light (approximately 400 nm). This residual excitation unnecessarily complicates multiple color imaging in combination with a Sapphire-type variant (Tsien, 1998; Ehrig et al., 1995; Heim et al., 1994) or fluorescence resonance energy transfer (FRET) experiments with a BFP donor (Heim et al., 1996; Mitra et al., 1996). mWasabi has very narrow excitation and emission peaks that are reminiscent of the spectrum of *Renilla* GFP (Ward et al., 1979) and monomeric Azami-Green (Karasawa et al., 2003). Narrower peaks allow for more efficient excitation and gathering of emission when used in combination with bandpass filters, and reduce the degree of bleed-through in multicolor imaging.

mWasabi, EGFP and Emerald have almost identical emission peak shapes (FIG. 25D). The differences in their excitation spectra are pronounced, with mWasabi showing almost no excitable component below 410 nm, suggesting that mWasabi may be superior to EGFP for use in two-color imaging with Sapphire. mWasabi and EGFP were fused with a nuclear localization signal (NLS) and separately co-expressed with Sapphire-β-actin in HeLa cells. Exciting Sapphire with a typical 375-415 nm bandpass excitation filter resulted in significant EGFP fluorescence as observed in the cell nucleus due to residual excitation of EGFP at 400 nm (FIG. 26). In contrast, no significant fluorescence was observed for mWasabi in the cell nucleus when Sapphire was imaged under identical conditions, demonstrating that mWasabi is suitable for multicolor imaging in combination with fluorophores which are excitable with violet light.

In live cell imaging, a fluorescent protein ideally should retain its favorable properties when either fused to a variety of proteins or targeted to a variety of subcellular compartments. Further, the fluorescent protein should not perturb the normal localization or biological function of the protein to which it is genetically fused. Such a perturbation can be caused by oligomerization of the fluorescent protein, a problem that is not relevant to monomeric fluorescent proteins such as mTFP1 and mWasabi. mWasabi is non-oligomerizing, enabling it to be expressed as a fusion to another protein of interest in order to monitor trafficking or interactions of the protein. As used herein, the term "non-oligomerizing" is intended to mean units which do not form trimers or tetramers.

Figure 27:
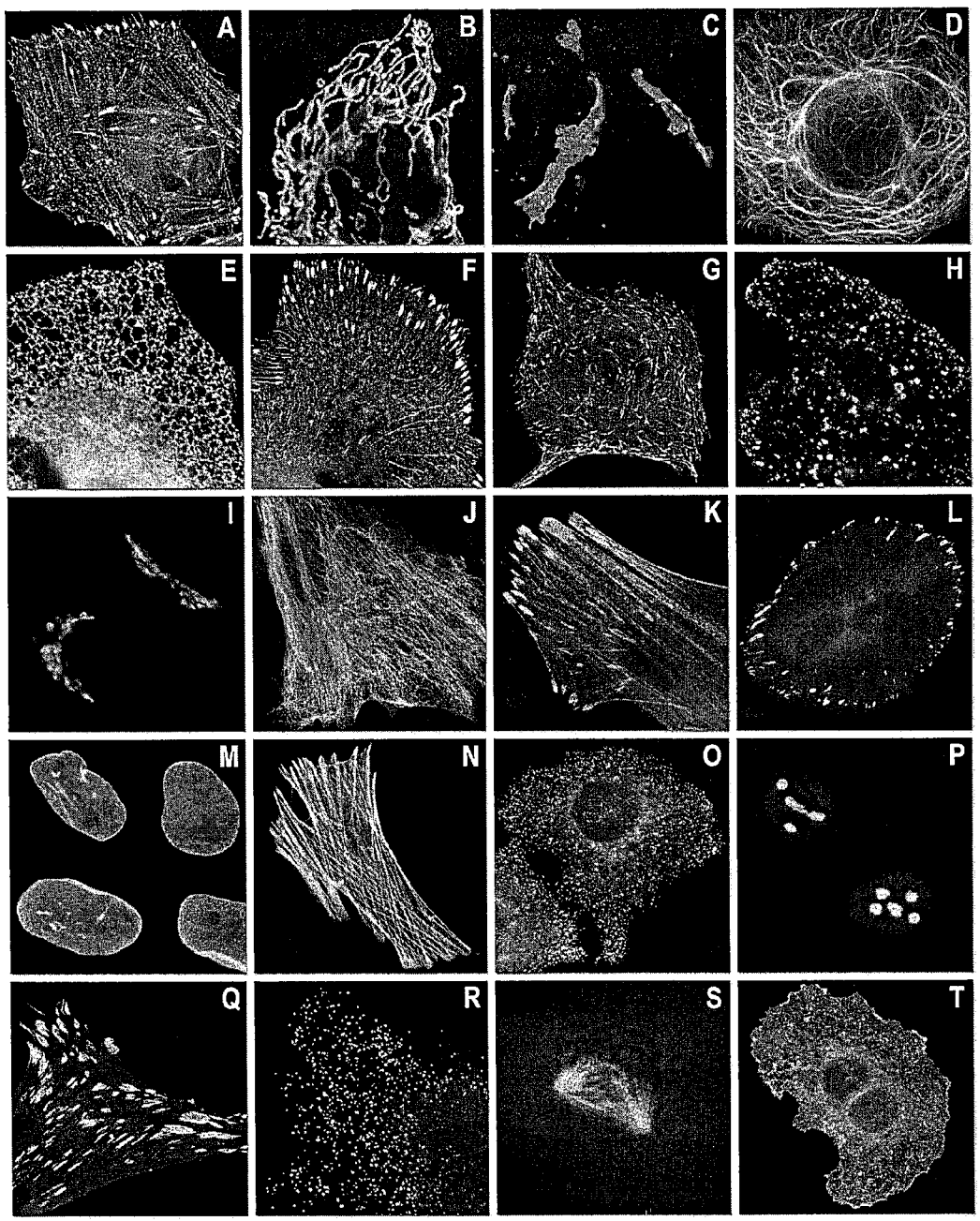
FIG. 27 shows fluorescence imaging of mTFP1 fusion constructs (A-K) N-terminal fusion constructs. For each fusion protein the linker amino acid length is indicated after the name of the targeted organelle or fusion protein. (A) mTFP1-α-actinin-19 (human non-muscle); (B) mTFP1-mitochondria-7 (human cytochrome C oxidase subunit VIII); (C) mTFP1-Cx43-7 (rat α-1 connexin-43); (D) mTFP1-Keratin-17 (human cytokeratin 18); (E) mTFP1-endoplasmic reticulum-3 (calreticulin signal sequence (51 nucleotides) and KDEL retention sequence); (F) mTFP1-paxillin-22 (chicken); (G) mTFP1-EB3-7 (human microtubule-associated protein; RP/EB family); (H) mTFP1-lysosomes-20 (rat lysosomal membrane glycoprotein 1); (I) mTFP 1-Golgi-7 (N-terminal 81 amino acids of human β-1,4-galactosyltransferase); (J) mTFP1-vimentin-7 (human); (K) mTFP1-zyxin-7 (human). (L-T) C-terminal fusion constructs. (L) mTFP1-Focal Adhesion Kinase-5 (chicken protein tyrosine kinase 2); (M) mTFP1-Lamin B1-10 (human); (N) mTFP1-β-Actin-7; (O) mTFP1-Clathrin Light Chain-15 (human); (P) mTFP1-Fibrillarin-7 (human); (Q) mTFP1-vinculin-23 (human); (R) mTFP1-peroxisomes-2 (peroximal targeting signal 1; PTS1); (S) mTFP1-β-tubulin-6 (human); (T) mTFP1-farnesyl-5 (20-amino acid farnesylation signal from c-Ha-Ras). The cell line used for expressing mTFP1 fusion vectors was Gray fox lung fibroblast cells (FoLu) in panels (A, G, K, N, and Q) and human cervical adenocarcinoma cells (HeLa) in the remaining panels.
Figure 28:
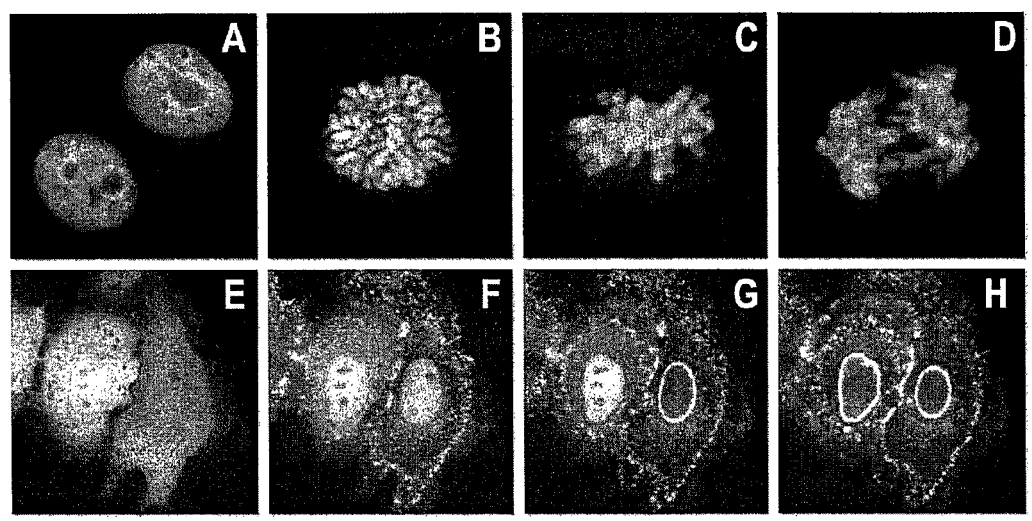
FIG. 28 shows live cell imaging of mTFP1 fusion vectors: (A-D) Laser scanning confocal images of a single HeLa cell expressing mTFP1-H2B-6 (N-terminus; human) progressing through interphase, prophase, metaphase, and anaphase, respectively. (E-H) Spinning disk confocal images selected from a time-lapse series of HeLa cells expressing mTFP1-annexin (A4)-12 (C-terminus; human) during ionomycin-induced translocation to the plasma and nuclear membranes (Piljic et al., 2006). (E) time=0, ionomycin added; (F) time=5 min; (G) time=7 min; (H) time=9 min.

The utility of mTFP1 and mWasabi was investigated in different fusion constructs. To test the range of proteins which would tolerate fusion to mTFP1 and mWasabi, a series of twenty-two different mTFP1 fusions to both the C- and N-terminus of the fluorescent protein were tested (FIGS. 27 and 28). Patterns of fluorescent localization were indistinguishable from those observed with well-established avGFP variants. As shown in FIG. 28, fusions to histone H2B and annexin A4 did not interfere with the normal cellular function of these proteins. A series of 20 similar fusions with mWasabi gave identical results. Importantly, both mTFP1 and mWasabi provide a bright and photostable fluorescent signal with no significant perturbation of the localization or function of the protein of interest.

As used herein, a "nucleic acid" or "polynucleotide" includes a nucleic acid, an oligonucleotide, a nucleotide, a polynucleotide, and any fragment, variant, or derivative thereof. The nucleic acid or polynucleotide may be double-stranded, single-stranded, or triple-stranded DNA or RNA (including cDNA), or a DNA-RNA hybrid of genetic or synthetic origin, wherein the nucleic acid contains any combination of deoxyribonucleotides and ribonucleotides and any combination of bases, including, but not limited to, adenine, thymine, cytosine, guanine, uracil, inosine, and xanthene hypoxanthine. The nucleic acid or polynucleotide may be combined with a carbohydrate, a lipid, a protein, or other materials. A nucleic acid sequence of interest may be chemically synthesized using one of a variety of techniques known to those skilled in the art, including, without limitation, automated synthesis of oligonucleotides having sequences which correspond to a partial sequence of the nucleotide sequence of interest, or a variation sequence thereof, using commercially-available oligonucleotide synthesizers, such as the Applied Biosystems Model 392 DNA/RNA synthesizer.

One nucleic acid composition of the present invention is the nucleotide sequence encoding mTFP0.86 (SEQ ID NO: 2; FIG. 10A). Another nucleic acid composition comprises the sequence encoding mTFP1 (SEQ ID NO: 6, FIG. 10B). A further nucleic acid composition comprises the sequence encoding mWasabi (SEQ ID NO: 19) (GenBank Accession EU024648). Accordingly, in one embodiment of the present invention, the isolated nucleic acid composition comprises a nucleic acid sequence having at least about 60% homology with the nucleotide sequence of SEQ ID NO: 2, SEQ ID NO: 6 or SEQ ID NO: 19. In another embodiment of the present invention, the isolated nucleic acid composition comprises a nucleic acid sequence having at least about 75% homology with the nucleotide sequence of SEQ ID NO: 2, SEQ ID NO: 6 or SEQ ID NO: 19. In still another embodiment of the present invention, the isolated nucleic acid composition comprises a nucleic acid sequence that is substantially the same as, or identical to, the nucleotide sequence of SEQ ID NO: 2, SEQ ID NO: 6 or SEQ ID NO:19. In one embodiment, the nucleic acid composition comprises any nucleic acid sequence which encodes any protein of the present invention, including proteins having the amino acid sequence SEQ ID NO: 3, SEQ ID NO: 7 or SEQ ID NO: 20. In certain embodiments, the nucleic acid sequence may be re-synthesized such that it is compatible with mammalian (e.g., human) codon usage, or the sequence may be resynthesized to be optimised for non-mammalian codon preferences.

The present invention further provides an isolated nucleic acid, including any mimetic or complement thereof, that hybridizes under stringent conditions to the nucleic acid composition described herein. The "complement" of a nucleic acid sequence refers, herein, to a nucleic acid molecule which is completely complementary to another nucleic acid, or which will hybridize to the other nucleic acid under conditions of stringency. Stringent (e.g., high-stringency) conditions are known in the art (see, e.g., Maniatis, 1989; Ausubel, 2001). Stringent conditions are sequence-dependent, and may vary depending upon the circumstances.

The present invention further provides a method of engineering a nucleic acid sequence encoding a non-oligomerizing *Clavularia* teal fluorescent protein (TFP) variant having a tyrosine-derived chromophore, by screening a fully-synthetic gene library. In one embodiment, the gene library comprises the nucleotide sequence of SEQ ID NO: 1 (FIG. 11).

The present invention also provides a vector comprising a nucleic acid sequence encoding the non-oligomerizing TFP variants having a tyrosine-derived chromophore described herein. Also provided is a host cell (e.g., a mammalian cell) comprising the vector.

In one embodiment of the present invention, the vector is a plasmid, although it is to be understood that other types of vectors, such as cosmids and phagemids, may also be used for the purposes of the present invention. The term "plasmid", as used herein, refers generally to circular double-stranded DNA, which is not bound to a chromosome. The DNA may be a chromosomal or episomal-derived plasmid. The plasmid of the present invention may optionally contain a terminator of transcription; a promoter; and/or a discrete series of restriction-endonuclease recognition sites, located between the promoter and the terminator. In the plasmid, a polynucleotide insert of interest (e.g., one encoding a non-oligomerizing *Clavularia* teal fluorescent protein (TFP) variant having a tyrosine-derived chromophore) should be operatively linked to an appropriate promoter, such as its native promoter or a host-derived promoter, such as the *E. coli* lacZ promoters, the trp and tac promoters, the T3 and T7 promoters, or the CMV promoters. Other suitable promoters will be known to the skilled artisan.

The vector of the present invention may comprise cDNA encoding a non-oligomerizing *Clavularia* teal fluorescent protein (TFP) variant having a tyrosine-derived chromophore. As used herein, the term "cDNA" refers to an isolated DNA polynucleotide or nucleic acid molecule, or any fragment, derivative, or complement thereof. The cDNA may be double-stranded, single-stranded, or triple-stranded, it may have originated recombinantly or synthetically, and it may represent coding and/or noncoding 5, and/or 3' sequences.

The vector of the present invention may be useful in a method for expressing the nucleic acid sequence in mammalian cells or non-mammalian cells. In one embodiment, the nucleic acid of the vector is expressed as a tandem genetic fusion to another protein.

The present invention further provides a non-oligomerizing *Clavularia* teal fluorescent protein (TFP) variant comprising a tyrosine-derived chromophore, as well as any derivative, fragment, or homologue thereof. The amino acid sequence of *Clavularia* sp. fluorescent protein FP484 may be obtained from GenBank Accession No. AF168424. The TFP variant of the present invention may be a monomer or a dimer.

In one embodiment of the present invention, the TFP variant includes a chromophore comprising the amino acid sequence tyrosine-glycine (YG). By way of example, the chromophore may comprise the amino acid sequence glutamine-tyrosine-glycine (QYG) as in cFP484. The chromophore may also comprise the amino acid sequence cysteine-tyrosine-glycine (CYG), glycine-tyrosine-glycine (GYG), the amino acid sequence alanine-tyrosine-glycine (AYG), or the amino acid sequence serine-tyrosine-glycine (SYG) as in variants mTFP0.7, mTFP0.75, mTFP0.86 and mWasabi, respectively.

Furthermore, the TFP variant of the present invention may comprise an amino acid sequence having at least about 60% homology with the amino acid sequence of SEQ ID NO: 3 (FIG. 12A), SEQ ID NO: 7 (FIG. 12B) or SEQ ID NO: 20. In one embodiment, the TFP variant comprises an amino acid sequence having at least about 75% homology with the amino acid sequence of SEQ ID NO: 3, SEQ ID NO: 7 or SEQ ID NO: 20. In another embodiment, the TFP variant comprises an amino acid sequence, which is substantially the same as, or identical to, the amino acid sequence of SEQ ID NO: 3, SEQ ID NO: 7 or SEQ ID NO: 20. In one embodiment, the TFP variant of the present invention may comprise at least one of the following mutations: H42N, L44V, L72F, F124L, M150L, and S179T. In another embodiment, the TFP variant of the present invention may also comprise at least one of the following mutations: A66S, K139E, H163M, S216I.

As discussed above, the inventors' variant proteins are advantageous in that they exhibit enhanced brightness. In one embodiment, the TFP variant of the present invention may have a fluorescence emission that is blue-shifted relative to the wild-type cFP484 protein. In one embodiment, the TFP variant of the present invention has a wavelength of maximum fluorescence emission that is less than about 504 nm. In another embodiment, the TFP variant of the present invention has an excitation spectrum ranging from about 350 to 500 nm and an emission spectrum ranging from about 450 to 600 nm. In another embodiment, the TFP variant has an excitation maximum ranging from about 450 to 460 nm and an emission maximum ranging from about 485 to 495 nm. In yet another embodiment, the TFP variant has an excitation maximum of about 493 nm and an emission maximum of about 509 nm.

In one embodiment, the invention may comprise a tandem dimer comprising two TFP dimers, operatively linked by a peptide linker. Thus, the dimers may be fused into a single non-oligomerizing gene product.

An exemplary tandem dimer of the present invention is tdTFP0.3. Accordingly, in one embodiment of the present invention, the tandem dimer is encoded by a DNA sequence comprising the nucleotide sequence of SEQ ID NO: 4 (FIG. 13). In another embodiment of the present invention, the tandem dimer comprises the protein sequence of SEQ ID NO: 5 (FIG. 14).

Additionally, the present invention provides an antibody that specifically binds to a TFP variant, as described herein. The antibody of the present invention may be polyclonal or monoclonal, and may be produced by techniques well known to those skilled in the art. Polyclonal antibody, for example, may be produced by immunizing a mouse, rabbit, or rat with purified protein. Monoclonal antibody then may be produced by removing the spleen from the immunized mouse, rabbit, or rat, and fusing the spleen cells with myeloma cells to form a hybridoma which, when grown in culture, will produce a monoclonal antibody.

The antibodies used herein may be labelled with a detectable marker or label. Labelling of an antibody may be accomplished using one of a variety of labelling techniques, including peroxidase, chemiluminescent labels known in the art, and radioactive labels known in the art. The detectable marker or label of the present invention may be, for example, a non-radioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker or label may be a radioactive marker, including, for example, a radioisotope. The radioisotope may be any isotope that emits detectable radiation. Radioactivity emitted by the radioisotope can be detected by techniques well known in the art. For example, gamma emission from the radioisotope may be detected using gamma imaging techniques, particularly scintigraphic imaging.

The present invention is described in the following Examples, which are set forth to aid in the understanding of the invention, and should not be construed to limit in any way the scope of the invention as defined in the claims which follow thereafter.

EXAMPLES

Example 1

General Methods and Materials

Example 1

General Methods and Materials

The synthetic gene library of *Clavularia* cFP486 variants was commissioned from the DNA Technologies Unit at the NRC Plant Biotechnology Group (Saskatoon, SK). Synthetic DNA oligonucleotides for cloning and construction of subsequent libraries were purchased from Sigma-Genosys™ Canada (Oakville, ON) or Integrated DNA Technologies (Coralville, Iowa). PCR products and products of restriction digest were routinely purified using the QIAquick™ PCR purification kit according to the manufacturers protocols (Qiagen), or by gel electrophoresis and extraction using the GenCatch™ gel extraction kit (Epoch Biolabs) or the QIAquick™ gel extraction kit (Qiagen). Plasmid DNA was purified from overnight cultures by using either the GeneJET™ Plasmid Miniprep Kit (Fermentas, ON) or the QIAprep™ Spin Miniprep kit (QIAGEN, Valencia, Calif.). Restriction enzymes were purchased from either Invitrogen™ or New England Biolabs. The cDNA sequences for all TFP and FP variants and fusion constructs was confirmed by dye terminator cycle sequencing using the DYEnamic™ ET kit (Amersham Biosciences). Sequencing reactions were analyzed at the University of Alberta Molecular Biology Service Unit and the Florida State University Bioanalytical and Molecular Cloning DNA Sequencing Laboratory. The proteins mECFP and mCerulean have the A206K mutation in addition to their characteristic substitutions (Zacharias, 2002; Rizzo, 2004 and 2005). All filters for fluorescence screening and imaging were purchased from Chroma Technology (Rockingham, Vt.), Omega Filters (Brattleboro, Vt.) and Semrock (Rochester, N.Y.).

Example 2

Selection of the Starting Template

Prior to the present invention, there were three reported naturally-occurring fluorescent proteins with tyrosine-derived chromophores and wavelengths of maximum fluorescence emission at less than 490 nm (Matz, 1999): ClavCFP (a.k.a. ClavFP484) from *Clavularia* sp., dsCFP (a.k.a. dsFP483) from *Discosoma striata*, and amCFP (a.k.a. amFP486) from *Anemonia majano*. At least one other CFP, mcCFP (a.k.a. mcCFP477) from *Montastrea cavernosa*, has been recently reported (Sun et al., FEBS Lett., 570:175-83, 2004). One other CFP, asCFP (a.k.a. MiCy) from *Acropara* sp., has a wavelength of maximum fluorescence of 495 nm, and, therefore, is essentially green (as opposed to cyan) in its fluorescence (Karasawa et al., Biochem. J., 381:307-12, 2004). The naturally-occurring CFPs have quantum yields (QY) of 0.24-0.48 and extinction coefficients (EC) of 24,000-40,000 M−1cm−1. All of the naturally-occurring CFPs are oligomers, with some reported to be trimers and some reported to be tetramers. Protein-sequence alignments of ClavCFP, dsFP483, and amFP483 revealed that, of 227 structurally-aligned residues, there are 78 residues that are conserved in all 3 CFPs (FIG. 3). There are an additional 91 residues that are conserved in two of the three CFPs.

Considering only these positions, the inventors determined that ClavCFP is the variant at 19%, dsFP483 at 34%, and amFP486 at 47%, of the 91 positions. Thus, ClavCFP is the closest to a "consensus" sequence. ClavCFP has one cysteine (position 175 with DsRed numbering), while each of dsFP483 and amFP486 has five cysteines. Multiple cysteine residues are undesirable, due to the unpredictable effects of thiol oxidation in applications where the CFP is targeted to an oxidizing subcellular environment—such as the secretary pathway or the bacterial periplasm. Accordingly, the inventors concluded that ClavCFP is a preferred template upon which to base this directed evolution.

Example 3

Library Construction and Mutagenesis

Figure 15A:
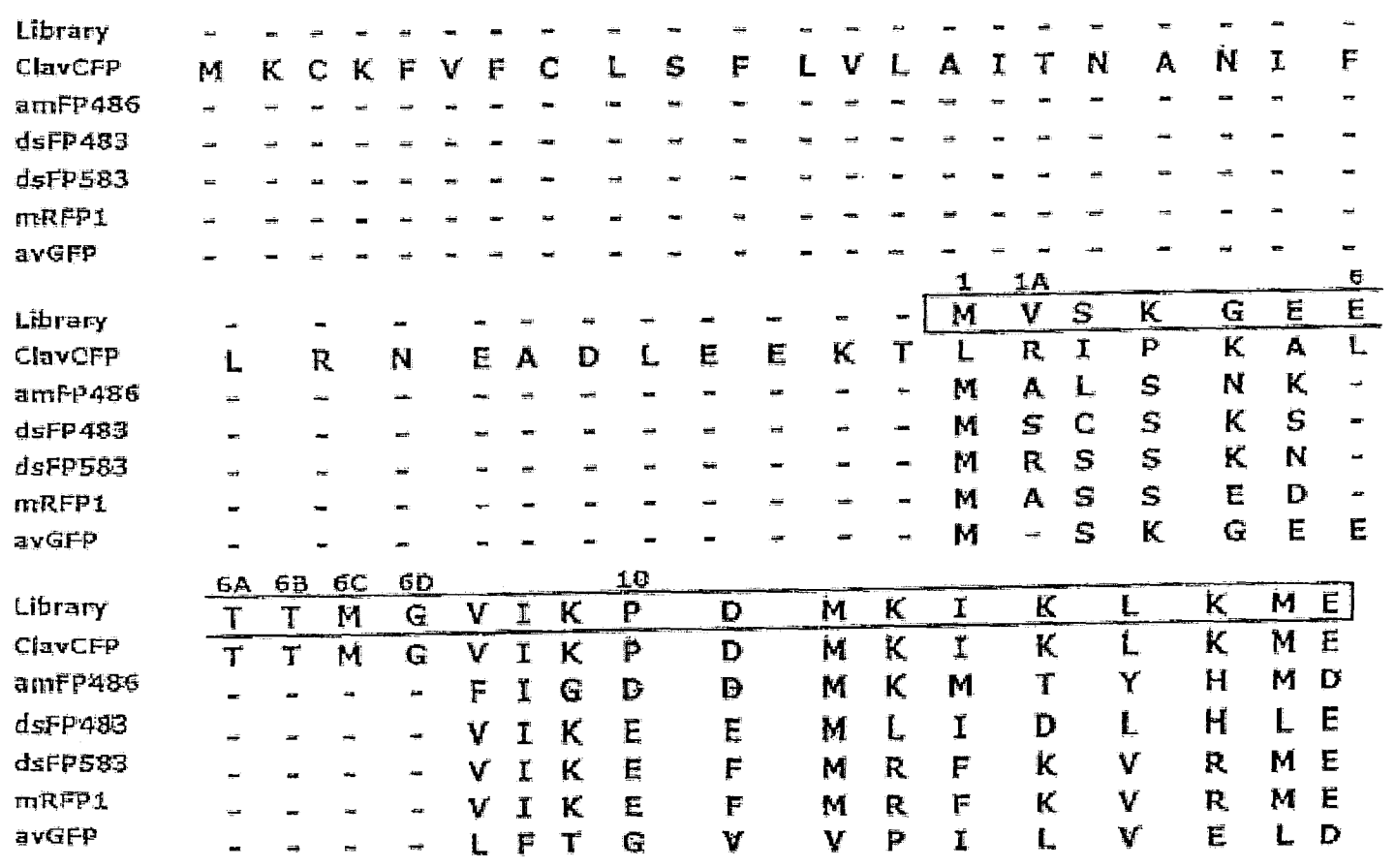
Figure 16:
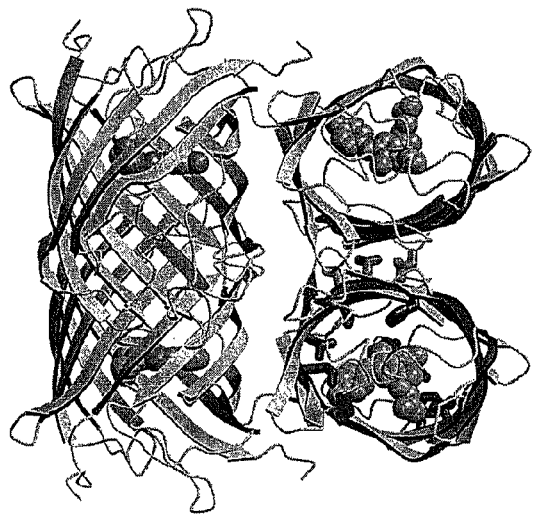
FIG. 16A illustrates degenerate amino acid positions in the synthetic library of FIG. 15, mapped onto the structure of DsRed, PDB ID 1G7K (Yarbrough, 2001). External positions are colored in green, and internal positions are colored in red. Position 66 is part of the chromophore and colored cyan.
FIG. 16B shows residues at which degenerate codons were introduced in the designed library.

The inventors commissioned the synthesis of the gene library encoding the designed protein library from the DNA Technologies Unit at the NRC Plant Biotechnology Group. The important features of the designed gene included: mammalian optimized codon usage, deletion of forty residues from the N-terminus, addition of the seven N-terminal and seven C-terminal residues of avGFP, semi-degenerate codons encoding potential "tetramer-breaking" mutations at three external positions, and semi-degenerate codons encoding potential rescuing mutations at eleven internal positions (FIGS. 11, 15, and 16). Library quality was verified by sequencing 77 independent clones, of which nine (12%) were confirmed to contain mutations at only the desired positions.

The initial synthetic gene library was digested with Xho1 and EcoR1 and ligated into similarly digested pBAD/HisB vector (Invitrogen). Subsequent libraries with saturation mutagenesis at a particular residue were constructed by either by an overlap-extension PCR method (Campbell, 2002) or the Quikchange™ protocol (Stratagene™). Randomly mutated libraries were constructed by error-prone PCR as previously described (Campbell, 2002) under conditions optimal for 3 mutations per 1,000 bp (Fromant, 1995). Full-length gene libraries resulting from overlap-extension PCR or error-prone PCR were ligated into the Xho1 and EcoR1 restriction sites of pBAD/HisB. Regardless of library assembly method, electrocompetent *Escherichia coli* strain DH10B (Invitrogen) was transformed and plated on Luria-Bertani (LB)/agar plates supplemented with ampicillin (0.1 mg/ml) and L-arabinose (0.02%). Plates were incubated for 14 h at 37° C. prior to screening.

Example 4

Screening

The system for imaging the fluorescence of bacterial colonies grown on 10 cm Petri dish is a custom built device similar to one previously described. Briefly, the light from a 175W xenon-arc lamp (Sutter) is passed through a 426 nm to 446 nm bandpass filter (Chroma) and into a bifurcated fiber optic bundle (Newport). Light exiting the fiber optic bundle illuminates (0.04 mW/cm$^2$) a 10 cm dish placed in a recessed holder on the bench top.

For all screening up to the identification of mTFP0.6, colony fluorescence was screened by viewing illuminated plates through a pair of custom goggles fitted with image quality 3 mm thick GG455 glass (Chroma). When viewed through these goggles, colonies fluorescing at 480-490 nm have a distinctly bluish hue and are easily distinguishable from 'greenish' colonies emitting at 500-510 nm. For the identification of mTFP0.7, colony fluorescence was digitally imaged with a Retiga 1300i 12-bit CCD camera (QImaging) fitted with filter wheel (Sutter) that contains both a 480/40 nm and a 530/30 nm bandpass filter. Through the use of custom macros for Image Pro Plus (Media Cybernetics), images in both emission channels were acquired and the fluorescence intensities of all colonies were individually integrated. Colonies with high 480/530 nm intensity ratios and high brightness at 480 nm were selected for further characterization.

For the identification of mTFP0.8, mTFP0.9, and mTFP1, the screening protocol was modified in order to select for photostability. We equipped six Royal Blue (peak emission at 455 nm) Luxeon™ V light emitting diodes (LEDs) (Lumileds Lighting) with narrow beam lenses (Fraen) and positioned them to evenly illuminate (55 mW/cm2) the 10 cm dish in the imaging system described above. Through the use of a custom serial port connection, the LEDs could be switched on and off at computer controlled intervals. Through the use of a custom serial port connection, the LEDs could be switched on and off at computer controlled intervals. An Image Pro Plus macro (Media Cybernetics) was used to automate acquisition and processing. For each plate, fluorescence images were acquired following a series of programmed intervals of intense illumination. Using this system, we could identify colonies with decreased propensity to photo-convert or otherwise photo-bleach.

For all screening protocols, colonies with more intense fluorescence or decreased propensity to photo-convert were picked and cultured overnight in 4 ml LB media containing ampicillin and arabinose. The following day 0.1 ml of each culture was dispensed into a 96-well plate (Nunc™) and the full emission spectra of each variant measured with a Safire2 plate reader (Tecan). Variants with the most blue-shifted and intense emission peak were used as templates in the subsequent round of library construction.

For the green fluorescing variants, the fluorescence emission of the colonies was screened by eye using tinted plastic goggles that block light with wavelength less than either 450 nm or 500 nm, as appropriate. During the directed evolution of green fluorescing variants, colonies with more intense fluorescence when illuminated with 460-490 nm light and viewed with the 500 nm cutoff goggles were picked for further investigation. Colonies of interest were cultured overnight in 4 mL LB medium containing ampicillin (0.1 mg/mL) and L-arabinose (0.2%). The following day 0.1 mL of each culture was dispensed into individual wells of a clear bottom 96-well plate (Nunc) and the full emission spectra of each variant measured with a Safire2 plate reader equipped with monochromators (Tecan). Variants with the most intense and red shifted fluorescence emission were used as templates in the subsequent round of library construction.

Example 5

Protein Purification and Characterization

To prepare proteins in sufficient quantity for characterization, E. coli strains DH10B or LMG194 were transformed with the pBAD/His B expression vector containing the gene of interest. A single colony was used to inoculate a 4 ml culture that was allowed to grow overnight (37° C., 225 rpm) before being diluted into 1 L of LB media containing ampicillin (0.1 mg/ml) and arabinose (0.2%). The culture was grown for 12 h before cells were harvested by centrifugation and lysed by French Press. Proteins were purified by Ni-NTA chromatography (Amersham). Cameleon constructs were further purified by gel filtration chromatography using a HiLoad™ 16/60 Superdex™ 75 pg column (GE Healthcare). Proteins were dialyzed into 50 mM Tris, pH 7.5.

The non-oligomeric structure of mTFP variants was determined by gel filtration chromatography on a HiLoad 16/60 Superdex 75 pg gel filtration column. Samples of the dimeric dTomato and the monomeric mCherry proteins (Shaner, 2004) were expressed and purified as described above and used as size standards. The AKTA basic liquid chromatography system (GE Healthcare) can monitor multiple wavelengths simultaneously. Purified TFP variants were mixed with either dTomato or mCherry and their respective elution profiles monitored separately at 450 nm and 550 nm, respectively.

For mWasabi studies, reference standards for determining the quantum yields of blue- or green-fluorescing FP variants were quinine sulfate in 0.1 M $H_2SO_4$ or EGFP, respectively. Extinction coefficients were calculated using the protein concentration as determined by the BCA method (Pierce) and the chromophore absorbance as determined by UV-visible spectroscopy. For fluorescence pKa measurements, the protein of interest was first dialyzed into dilute buffer (5 mM Tris HCl, pH 7.5) before being diluted into a series of 200 mM phosphate and imidazole buffers at various pH values. Fluorescent intensity was measured using a Safire2 plate reader.

Example 6

Spectroscopy

Figure 17:
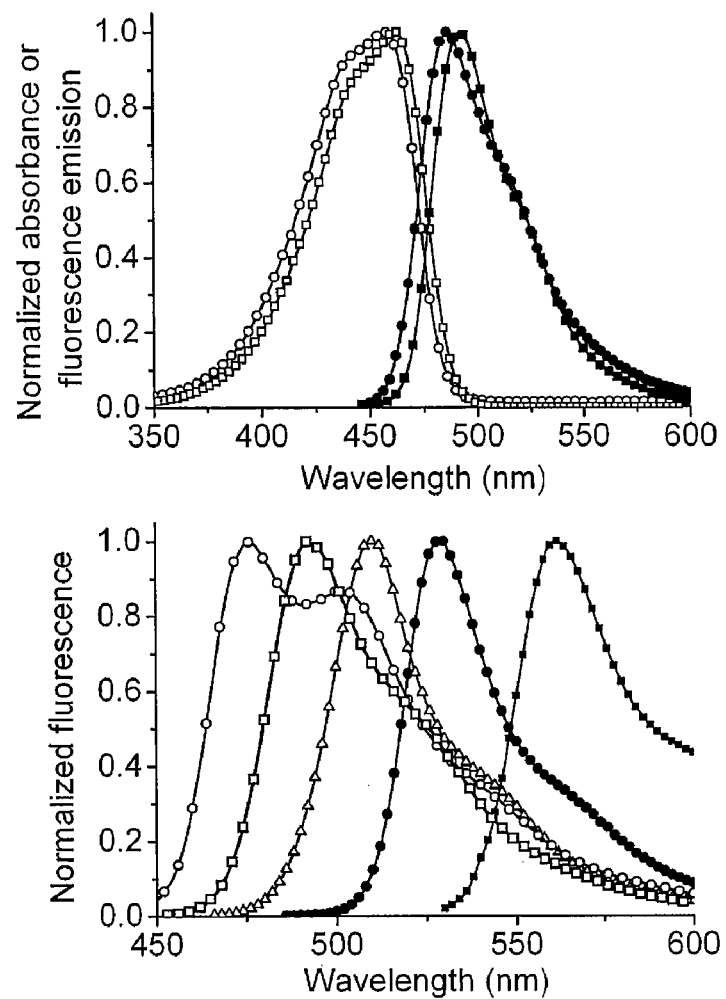
FIG. 17: Absorbance and fluorescence emission spectra of dTFP0.2, mTFP1, and selected fluorescence proteins. (A) Absorbance (open symbols) and fluorescence emission (filled symbols) spectra of dTFP0.2 (○, ●) and mTFP1 (□, ■). (B) Fluorescence emission spectra of mCerulean (○) (Rizzo, 2004 & 2005), mTFP1 (□), EGFP (Δ), Citrine (●) (Griesbeck, 2001), mOrange (■), and mCherry (▲) (Shaner, 2004).

Absorption spectra were recorded on a DU-800 UV-visible spectrophotometer (Beckman). Quantum yields for TFP variants were measured using fluorescein in 10 mM NaOH as the reference standard (Brannon, 1978). Extinction coefficients were measured by the alkali denaturation method (Shaner, 2004; Ward, 1998). A QuantaMaster spectrofluorometer (Photon Technology International) was used to acquire the emission spectra (excitation at 435 nm) shown in FIG. 8 and FIG. 17. All emission spectra have been corrected for the instrument response. Fluorescence lifetimes were determined on a TimeMaster time-resolved spectrofluorometer (Photon Technology International), which uses the stroboscopic optical boxcar technique (James, 1992). Lifetimes were determined in 10 mM Tris pH 8.0 with 1 mM EDTA and 50 mM NaCl at a protein concentration of 0.1 μM. A nitrogen dye laser at 440 nm was used for excitation, and the emission monochromator was set to either 480 nm (for mECFP and mCerulean) or 490 nm for mTFP1. A 480/40 nm bandpass filter was used on the emission channel to further minimize scattered light. Slits were adjusted as necessary to obtain adequate fluorescent intensity when using polarizing filters at 'magic angle' conditions or lower concentrations of fluorescent protein. The photostability of mTFP1 under arc lamp illumination was determined using the method of Shaner et al. (Shaner, 2005).

To determine the pH-dependence of the fluorescence emission of mECFP, mCerulean, and mTFP1, each protein (stock solution of 1 mg/ml in 5 mM Tris pH 7) was diluted 1:100 in a 96-well plate black clear bottom plate (Corning) containing 0.1 ml buffer (100 mM) at pH values ranging from 2 to 9. Full emission spectra at each pH were acquired with a Safire2 plate reader (Tecan). The relative fluorescence at each pH was measured at the peak wavelength.

Example 7

Cameleons and Actin-Fusion for Imaging in Mammalian Cells

To construct expression vectors for cameleon variants, the gene encoding yellow cameleon3.3 (YC3.3) was first inserted into the Xho1 and EcoR1 sites of the pBAD/His B bacterial expression vector (Griesbeck, 2001). The cDNAs encoding mECFP, mCerulean, and mTFP1 were each PCR amplified with primers that added a 5' Xho1 and a 3' Sph1 site. To maintain identical linker lengths, the 3' Sph1 site was appended immediately after the codon encoding Ala227 of mECFP and mCerulean or after the codon encoding the structurally aligned Arg220 of mTFP1. The purified PCR products were digested and ligated into the similarly digested YC3.3 gene. Cameleons expressed in E. coli were expressed and purified as described herein. To create the mTFP1-YC3.3 mammalian cell expression vector, the full-length gene in pBAD/His B was PCR amplified with a 5' primer that appended a HindIII restriction site, a Kozak sequence (gccac-cgccATGc, where ATG is the start codon (SEQ ID NO: 17), and the endoplasmic reticulum (ER) targeting sequence of calreticulin (MLLSVPLLLGLLGLAAAD) (SEQ ID NO: 18). The 3' primer appended the ER retention signal (KDEL) followed by an EcoR1 restriction site. The PCR product was digested with HindIII/EcoR1 and ligated with appropriately digested pcDNA3 (Invitrogen).

To create the mTFP1-actin mammalian expression plasmid, the gene encoding mTFP1 was PCR amplified with a 5' primer encoding an Nhe1 site and a 3' primer encoding an Xho1 site. The purified and digested PCR product was ligated into the pEGFP-actin vector (Clontech™) that had been previously digested with the same restriction enzymes to excise the EGFP coding sequence. DNA was purified by Plasmid Midi™ kit (Qiagen). HeLa cells were cultured in DMEM (Invitrogen) supplemented with 10% FBS (Sigma) at 37° C. Cells in 35 mm imaging dishes were transfected with 4 μg plasmid DNA mixed with 10 μg PEI in 0.5 ml OptiMEM™ (Invitrogen) and serum was added after 3 h. Approximately 14 h later the medium was exchanged for Hanks' Balanced Salt Solution (HBSS) containing no calcium chloride, magnesium chloride, magnesium sulfate, or phenol red (Invitrogen) or PBS and the cells were imaged. HeLa cells expressing mTFP1-β-actin or mTFP1-α-tubulin were imaged using a LSM510 confocal microscope (Zeiss) equipped with a 5 mW 458 nm excitation laser. HeLa cells expressing mTFP1-YC3.3 were imaged with a Zeiss Axiovert 200M epi-fluorescence inverted microscope equipped with a xenon arc lamp and a monochrome Retiga 2000R 12-bit cooled CCD camera (QImaging). The external excitation filter wheel, excitation shutter, and emission filter wheel are controlled through a Lambda 10-3 controller (Sutter). Only dichroic mirrors are housed in the motorized reflector turret. The QED InVivo software package (Media Cybernetics) is used for automated computer control of all microscope hardware and for quantitative image analysis. To create the mTFP1-α-tubulin expression vector, an identical procedure was used to replace the EGFP gene in pEGFP-tub (Clontech) with the gene encoding mTFP1.

To create the Sapphire-actin and mWasabi-NLS vectors, the genes encoding Sapphire (also known as H9-40) (Tsien, 1998; Ehrig et al., 1995; and Heim et al., 1994) and mWasabi were PCR amplified with a 5' primer encoding an NheI site and a 3' primer encoding an XhoI site. The purified and digested PCR products were ligated into pEGFP-actin or pEYFP-Nucleus (Clontech), respectively, which had been previously digested with the same restriction enzymes to excise the FP coding sequence. An analogous nuclear localization construct was made for EGFP. All of the other mTFP1 and mWasabi vectors were constructed using C1 and N1 (Clontech-style) cloning vectors. The FPs were amplified with a 5' primer encoding an AgeI site and a 3' primer encoding either a BspEI (C1) or Not1 (N1) site. The purified and digested PCR products were ligated into similarly digested EGFP-C1 and EGFP-N1 cloning vector backbones. To generate fusion vectors, the appropriate cloning vector and an EGFP fusion vector were digested, either sequentially or doubly, with the appropriate enzymes and ligated together after gel purification. Thus, to prepare mTFP1 and mWasabi N-terminal fusions, the following digests were performed: human non-muscle α-actinin, EcoRI and NotI (vector source, Tom Keller, FSU); human cytochrome C oxidase subunit VIII, BamHI and NotI (mitochondria, Clontech); human zyxin, BamHI and NotI (Clare Waterman-Storer, NIH); rat α-1 connexin-43 and rat β-2 connexin-26, EcoRI and BamHI (Matthias Falk, Lehigh University); human H2B, BamHI and NotI (George Patterson, NIH); N-terminal 81 amino acids of human β-1,4-galactosyltransferase, BamHI and NotI (Golgi, Clontech); human microtubule-associated protein EB3, BamHI and NotI (Lynne Cassimeris, Lehigh University); human vimentin, BamHI and NotI (Robert Goldman, Northwestern University); human keratin 18, EcoRI and NotI (Open Biosystems, Huntsville, Ala.); chicken paxillin, EcoRI and NotI (Alan Horwitz, University of Virginia); rat lysosomal membrane glycoprotein 1, AgeI and NheI (George Patterson, NIH); endoplasmic reticulum (calreticulin signal sequence and KDEL retention sequence), AgeI and EcoRI (Clontech). To prepare mTFP1 and mWasabi C-terminal fusions, the following digests were performed: human α-actin, NheI and BglII (Clontech); human α-tubulin, NheI and BglII (Clontech); human light chain clathrin, NheI and BglII (George Patterson, NIH); human lamin B1, NheI and BglII (George Patterson, NIH); human fibrillarin, AgeI and BglII (Evrogen); human vinculin, NheI and EcoRI (Open Biosystems, Huntsville, Ala.); peroximal targeting signal 1 (PTS1—peroxisomes), AgeI and BspEI (Clontech); chicken protein tyrosine kinase 2, AgeI and BglII (Clare Waterman-Storer, NIH); human annexin (A4), AgeI and BspEI (Alen Piljic, EMBL, Heidelberg); human RhoB GTPase with an N-terminal c-Myc epitope tag (endosomes), AgeI and BspEI (Clontech); and the 20-amino acid farnesylation signal from c-Ha-Ras, AgeI and BspEI (membrane, Clontech). DNA for mammalian transfection was prepared by either the Plasmid Midi or Maxi kit (QIAGEN).

HeLa epithelial (CCL-2, ATCC) and Grey fox lung fibroblast (CCL-168, ATCC) cells were either cultured and transfected according to Ai et al. (2006), or grown in a 50:50 mixture of DMEM and Ham's F12 with 12.5% Cosmic calf serum (Hyclone) and transfected with Effectene (QIAGEN). For dual color imaging, the two expression plasmids were pre-mixed in a 1:1 ratio before transfection. Widefield live cell imaging was performed with a Zeiss Axiovert 200M microscope equipped with appropriate filter sets (Chroma), a Nikon™ TE-2000 inverted microscope equipped with Omega filters, or an Olympus IX71 equipped with Semrock filters. Laser scanning confocal microscopy was conducted on a Nikon C1Si and an Olympus FV1000, both equipped with argon-ion 457 and 488 nm lasers and proprietary filter sets. Spinning disk confocal microscopy was performed on an Olympus DSU-IX81 equipped with a Lumen 200 illuminator (Prior, Boston, Mass.), Semrock filters, and 10-position filter wheels driven by a Lambda 10-3 controller (Sutter, Novato, Calif.).

Sapphire fluorescence was measured using a 375-415 nm bandpass excitation filter, a 475 nm longpass beamsplitter, and 500-550 nm bandpass emission filters. mTFP1 was imaged with a CFP filter set (96188, Nikon) or a custom set composed of a 430-460 nm bandpass excitation filter, a 475 nm longpass beamsplitter, and a 480-520 nm bandpass emission filter. EGFP and mWasabi were imaged using either a standard EGFP filter set (41017, Chroma), a QuantaMax™ Green set (Omega), or a BrightLine GFP set (3035B, Semrock).

Example 8

Photostability Measurements

For photostability measurements of green-fluorescing variants, microdroplets of either the purified protein (100 µM) or *E. coli* culture (previously transformed with the expression plasmid and induced) was mixed with mineral oil and vortexed. Approximately 5 µL of this suspension was sandwiched between a glass slide and a glass cover slip. Individual drops were identified by fluorescence microscopy and subjected to photobleaching according to Ai, et al. (2007). EGFP was subjected to bleaching under identical conditions and used as a reference standard.

Example 9

Development of the Variants

The sequence of mutations and changes that led to the variants described herein can be summarized as follows:
1. cCFP484: initial wild-type sequence;
2. dTFP0.10: wild-type cCFP484 (a.k.a. TFP) with additional mutations H42N, L44V, L72F, F124L, D125K, M127K, M150L, S179T;
    deleted $1^{st}$ 40 residues, and appended MVSKGEE to the start (N-terminus) of the protein;
    appended GMDELYK to the end (C-terminus) of the protein;

3. dTFP0.20: dTFP0.10 with additional mutations D81N, S226P;
4. dTFP0.30: dTFP0.20 with additional mutations Q66G, K182R;
5. tdTFP0.30: genetically fused 2 copies of dTFP0.3, in which GMDELYK was deleted from the C-terminus of the first copy, and MVSKGEE was deleted from the N-terminus of the second copy;
   a linker sequence of TGSTLVSGSGTA was used;
   the S226P mutation was reverted to P in the first copy;
6. mTFP0.3: dTFP0.2 with additional mutations S162K, S164K;
7. mTFP0.4: mTFP0.3 with additional mutations Q66C, C175V;
8. mTFP0.5: mTFP0.4 with additional mutations S62T, C66G, A80P, K127E, K182R, N216S
9. mTFP0.6: mTFP0.4 with additional mutations S2N, G66A, L213V replaced residues L223 to A228 (sequence LLPSQA) with sequence TG;
10. mTFP0.7: mTFP0.6 with additional mutations N2S (reversion), V441, R123H, Y173H, V186A;
11. mTFP0.8: mTFP0.7 with additional mutation N63T
12. mTFP0.9: mTFP0.8 with additional mutations K142G, E144D, P145A, 1149R, L150M (reversion to wide sequence), 1161V;
13. mTFP1.0: mTFP0.9 with additional mutations L141T, V158K, Y221N, G224D;
14. G1: mTFP1.0 with additional mutation H163M;
15. G2: mTFP1.0 with additional mutations K139E/H163M;
16. G3: mTFP1.0 with additional mutations T73A/K139E/H163M;
17. G2.1: mTFP1.0 with additional mutations A66S/K139E/H163M
18. mWasabi: mTFP1.0 with additional mutations A66S, K139E, H163M, S216I.

Discussed below are results obtained by the inventors in connection with the experiments of Examples 2, 3 and 9.

Results of Directed Evolution

Figure 18:
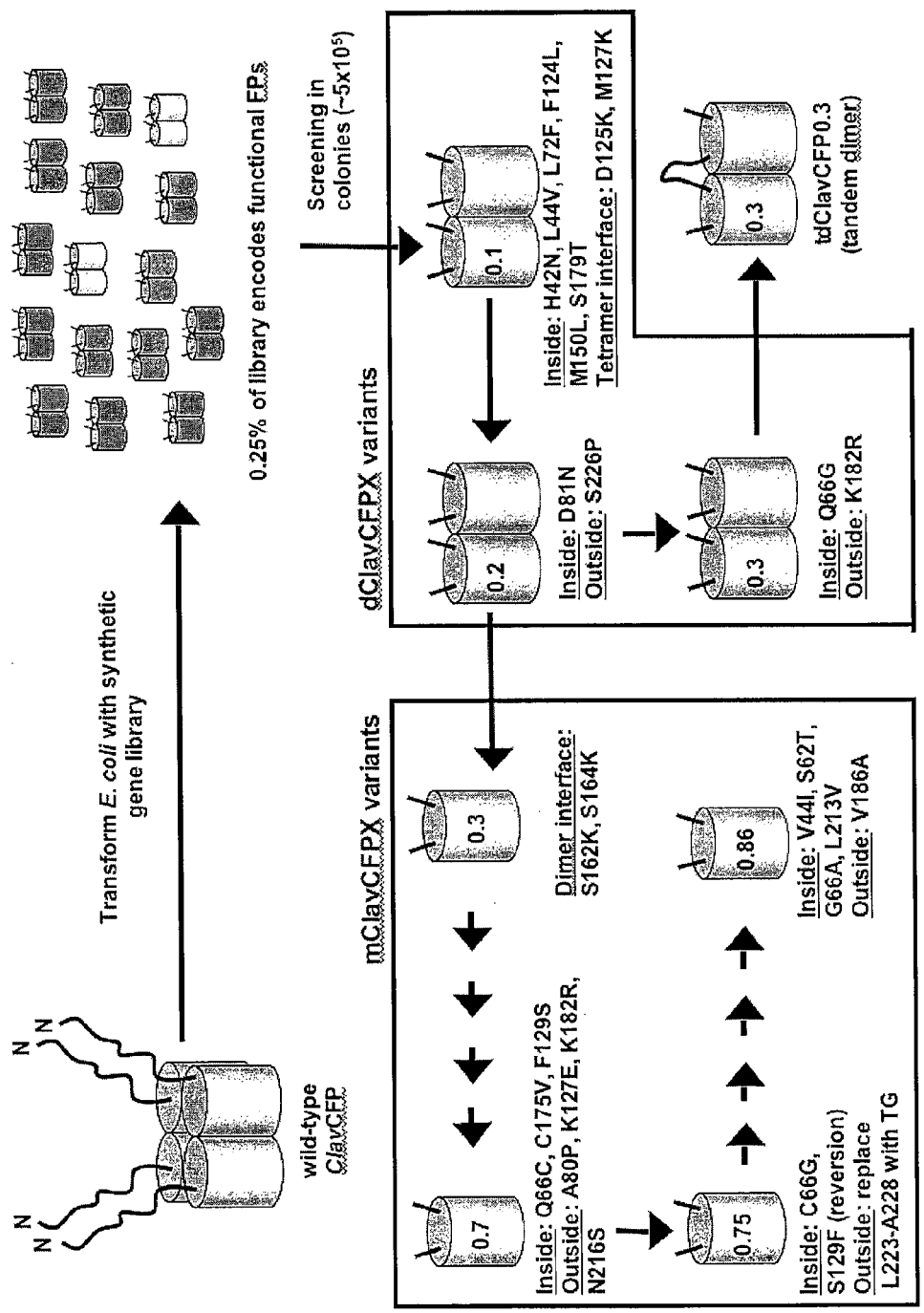
FIG. 18 provides an overview of the library screening and the subsequent directed evolution process. Only 0.25% of the gene library encoded functional fluorescent proteins; of these, approximately 50% were green fluorescent and 50% were cyan fluorescent.
Figure 19:
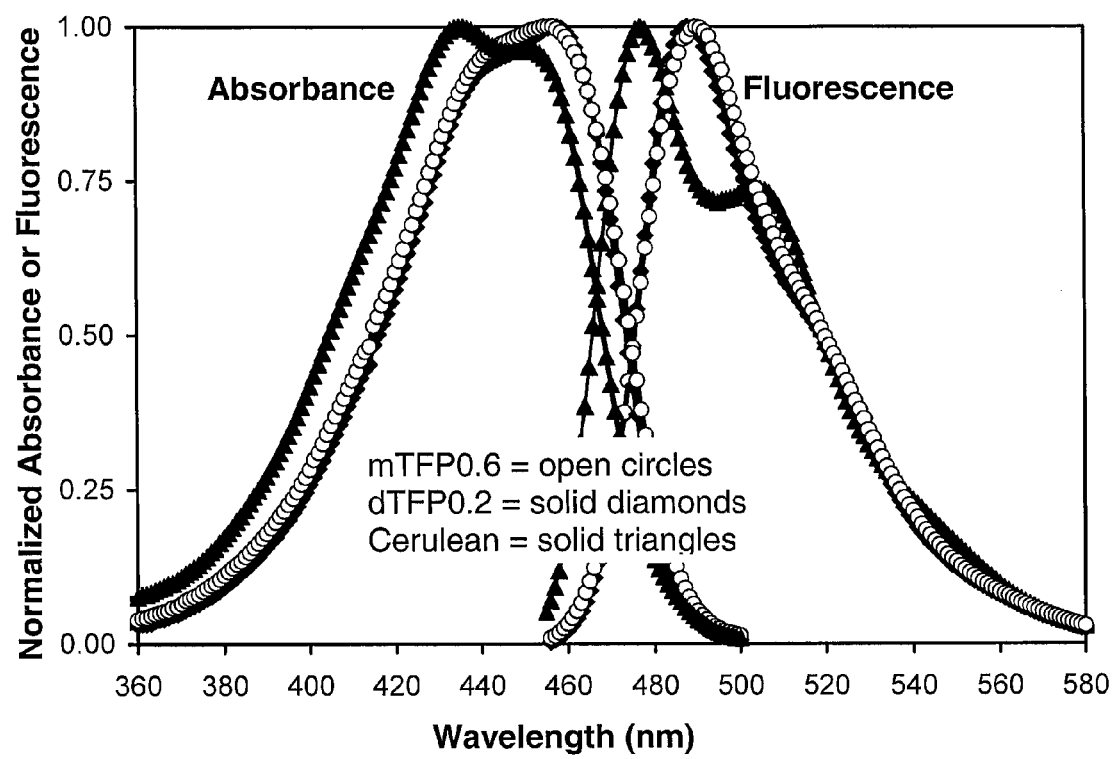
FIG. 19 illustrates fluorescence excitation and emission for Cerulean, dTFP0.2, and mTFP0.7. Note that mTFP0.7 is slightly red-shifted from dTFP0.2, but both proteins have a narrow fluorescence emission compared to Cerulean. The narrow fluorescence emission can be attributed to the different chromophore structure.
Figure 20:
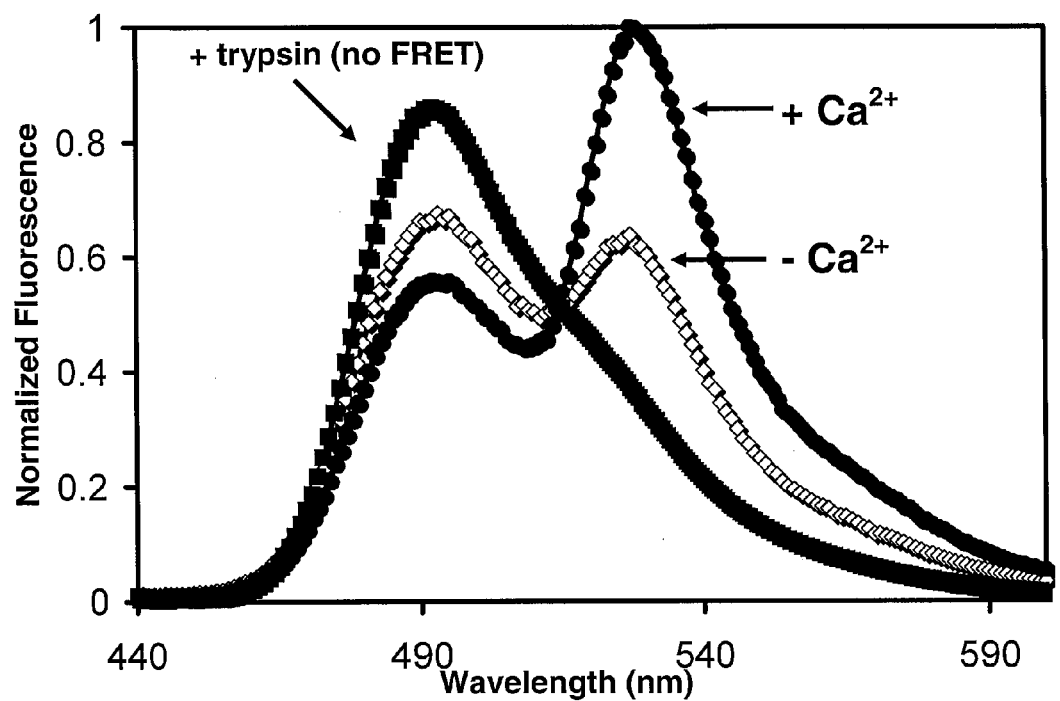
FIG. 20 depicts a demonstration of mTFP0.6 as a Forster (or fluorescence) resonance energy transfer (FRET) donor to Citrine (a YFP) in a ratiometric calcium sensor. The results of this experiment are summarized in Table 5 of the Examples.

Extensive screening of the synthetic gene library resulted in identification of a brightly-fluorescent dimer (quantum yield (QY)=0.73, extinction coefficient (EC)=42,000 M−1cm−1) with eight mutations relative to the wild-type sequence (FIGS. 18 and 19). Directed evolution was used to evolve the dimer to a substantially-brighter variant (QY=0.89, EC=60,000 M−1cm−1). Site-directed mutagenesis of the residues in the predicted dimer interface produced a monomeric (QY=0.41, EC=19,000 M−1cm−1) version that required many rounds of directed evolution in order to rescue and improve the fluorescent brightness. Currently, mTFP0.86 has a QY=0.65 and an EC=59,000 M−1cm−1; mTFP0.86 is 3.6-fold brighter than avCFP, and 1.4-fold brighter than Cerulean (Rizzo, 2004).

Evaluation of MTFP as a FRET Donor

Analogous versions of yellow cameleon 3.3 (YC3.3), containing either ECFP, Cerulean, or an mTFP0.6, were constructed, and their response to Ca2+ was determined (Miyawaki et al., Nature, 388:882-87, 1997). Cameleon is a Ca2+ reporter that has been optimized to maximize the change in ratio between an ECFP donor and a YFP acceptor. Therefore, it is not surprising that substituting mTFP0.6 for ECFP resulted in a decreased % ratio change. However, the high FRET efficiencies observed with mTFP0.6, in both the presence and absence of Ca2+, showed that it is a very good FRET donor to citrine (FIG. 8 and Table 5).

TABLE 5

Summary of ratio changes and FRET efficiency changes for "cameleon-type" calcium sensors, based on either avCFP, Cerulean, or mTFP0.6.

|  | ECFP | | Cerulean | | mTFP0.6 | |
| --- | --- | --- | --- | --- | --- | --- |
|  | yellow/cyan ratio | FRET efficiency | yellow/cyan ratio | FRET efficiency | yellow/cyan ratio | FRET efficiency |
| −Ca$^{2+}$ | 1.48 | 14% | 1.28 | 13% | 0.94 | 25% |
| +Ca$^{2+}$ | 3.59 | 37% | 2.93 | 35% | 1.79 | 38% |
| % ratio change | 242% | | 230% | | 190% | |
| Δ FRET efficiency | 23% | | 22% | | 13% | |

Figure 21:
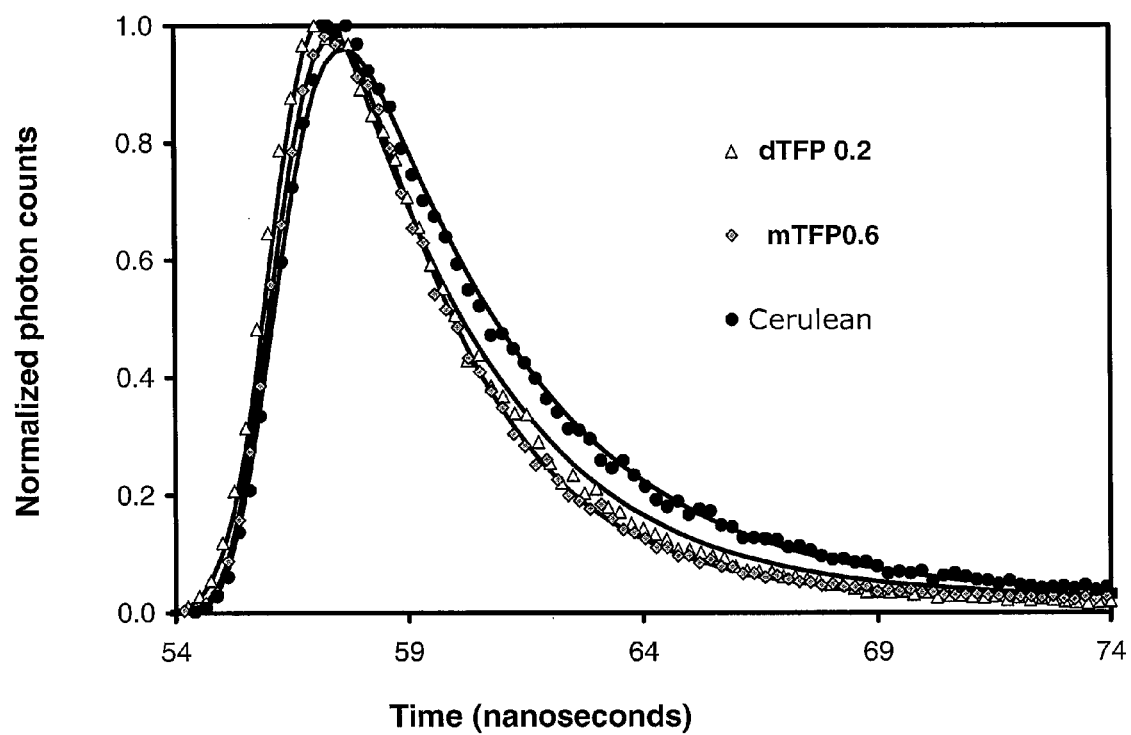
FIG. 21 presents the fluorescence lifetime decay for Cerulean, dTFP0.2, and mTFP0.6.
Figure 22:
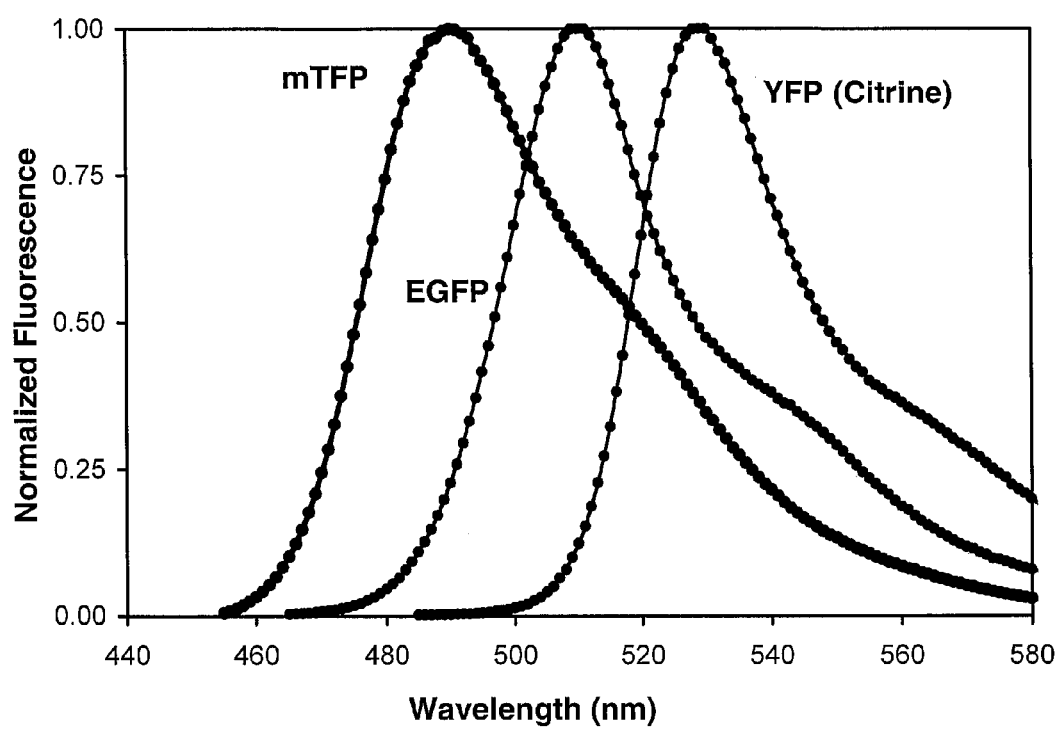
FIG. 22 presents the fluorescent emission spectra of mTFP, avGFP, and Citrine (a YFP).

Both mTFP0.6 (labelled mTFP0.6) and Cerulean can be fitted to a single exponential fluorescence lifetime decay (FIG. 21). The inventors have inserted mTFP0.6 (labelled mTFP0.6) into cameleon-type constructs, and demonstrated that it is an excellent FRET donor to Citrine.

While the foregoing invention has been described in some detail for purposes of clarity and understanding, it will be appreciated by one skilled in the art, from a reading of the disclosure, that various changes in form and detail can be made without departing from the true scope of the invention in the appended claims.

REFERENCES

The following references are referred to by first author's last name and year of publication, in parenthesis, in the above description and are incorporated herein as if reproduced in their entirety.

Ai, H. W., Henderson, J. N., Remington, S. J. and Campbell, R. E. *Biochemistry* 400, 531-540 (2006).
Ai, H. W., Shaner, N. C., Cheng, Z., Tsien, R. Y. and Campbell, R. E. *Biochemistry* 46, 5904-5910 (2007).
Ando, R.; Mizuno, H. and Miyawaki, A. *Science,* 306:1370-73 (2004).
Ausubel et al., eds., *Current Protocols in Molecular Biology* (New York, N.Y.: John Wiley & Sons, Inc., 2001.
Bevis, B. J. and Glick, B. S., *Nat Biotechnol* 20, 83-87 (2002).
Brannon, J. H. and Magde, D., *Journal of Physical Chemistry* 82, 705-709 (1978).
Campbell, R. E.; Tour, O.; Palmer, A. E.; Steinbach, P. A.; Baird, G. S.; Zacharias, D. A. and Tsien, R. Y. *Proc Natl Acad Sci USA* 99, 7877-7882 (2002).
Cinelli, R. A., Tozzini, V., Pellegrini, V., Beltram, F., Cerullo, G., Zavelani-Rossi, M., De Silvestri, S., Tyagi, M. and Giacca, M. *Phys Rev Lett* 86, 3439-3442, (2001).
Cubitt, A. B., Woollenweber, L. A. and Heim, R. *Methods Cell Biol* 58, 19-30, (1999).
Ehrig, T., O'Kane, D. J. and Prendergast, F. G. Green-fluorescent protein mutants with altered fluorescence excitation spectra. FEBS Lett 367, 163-166 (1995).
Fromant, M., Blanquet, S. and Plateau, P., *Anal Biochem* 224, 347-353 (1995).
Griesbeck, O., Baird, G. S., Campbell, R. E., Zacharias, D. A. and Tsien, R. Y., *J Biol Chem* 276, 29188-29194 (2001).
Gurskaya, N. G., Savitsky, A. P., Yanushevich, Y. G., Lukyanov, S. A. and Lukyanov, K. A. *BMC Biochem* 2, 6, (2001).
Heim, R.; Prasher, D. C. and Tsien, R. Y., *Proc. Nat. Acad. Sci., USA,* 91:12501-504, (1994).
Heim, R., Cubitt, A. B. and Tsien, R. Y., *Nature* 373, 663-664 (1995).

Heim, R. and Tsien, R. Y. *Curr Biol* 6, 178-182 (1996).
Henderson, J. N. and Remington, S. J. *Proc. Nat. Acad. Sci., USA*, 102:12712-12717, (2005).
International Application Publication No. WO0127150.
James, D. R., Siemiarczuk, A. and Ware, W. R., *Review of Scientific Instruments* 63, 1710-1716 (1992).
Karasawa, S.; Araki, T.; Nagai, T.; Mizuno, H. and Miyawaki, A. *Biochem. J.*, 381:307-12, 2004.
Karasawa, S.; Araki, T.; Yamamoto-Hino, M. and Miyawaki, A. *J. Biol. Chem.*, 278:34167-171, 2003.
Lukyanov, K. A.; Chudakov, D. M.; Lukyanov, S. and Verkhusha, V. V. *Nat Rev Mol Cell Biol*, 6, 885-891 (2005).
Maniatis et al., *Molecular Cloning: A Laboratory Manual*, 2nd ed. (Cold Spring Harbor: Cold Spring Harbor Laboratory, 1989.
Marques, M. A., Lopez, X., Varsano, D., Castro, A. and Rubio, A. *Phys Rev Lett* 90, 258101, (2003).
Matz, M. V.; Fradkov, A. F.; Labas, Y. A.; Savitsky; A. P.; Zaraisky, A. G.; Markelov, M. L. and Lukyanov, S. A. *Nat Biotechnol* 17, 969-973 (1999).
Matz, M. V.; Fradkov, A. F.; Labas, Y. A.; Savitsky; A. P.; Zaraisky, A. G.; Markelov, M. L. and Lukyanov, S. A. *Nat Biotechnol* 17, 1227 (1999).
Mitra, R. D., Silva, C. M. and Youvan, D. C. Gene 173, 13-17, (1996).
Miyawaki, A.; Llopis, J.; Heim, R.; McCaffery, J. M.; Adams, J. A.; Ikura, M. and Tsien, R. Y. *Nature* 388, 882-887 (1997).
Miyawaki, A. and Tsien, R. Y. *Methods Enzymol*, 327, 472-500 (2000).
Nguyen, A. W. and Daugherty, P. S. *Nat Biotechnol* 23, 355-360 (2005).
Ormo, M. et al. *Science* 273, 1392-1395 (1996).
Patterson, G. H. and Lippincott-Schwartz, J. *Science* 297, 1873-1877, (2002).
Pedelacq, J. D., Cabantous, S., Tran, T., Terwilliger, T. C. and Waldo, G. S. *Nat. Biotechnol.* 24, 79-88, (2006).
Piljic, A. and Schultz, C. *Mol. Biol. Cell* 17: 3318-3328, (2006).
Rizzo, M. A., Springer, G. H., Granada, B. & Piston, D. W. *Nat Biotechnol* 22, 445-449 (2004).
Rizzo, M. A. and Piston, D. W., *Biophys J* 88, L14-16 (2005).
Shaner et al., *Nat. Biotechnol.*, 22:1567-72, 2004.
Shaner, N. C., Steinbach, P. A. and Tsien, R. Y. *Nat Methods* 2, 905-909 (2005).
Shimomura, O. *Febs Letters* 104, 220-222 (1979).
Sun, Y.; Castner, E. W. Jr., Lawson, C. L.; Falkowski, P. G.; *FEBS Lett.*, 570:175-83, (2004).
Tsien, R. Y., *Annu. Rev. Biochem.*, 67:509-44, 1998.
Waldo, G. S., Standish, B. M., Berendzen, J. and Terwilliger, T. C. *Nat. Biotechnol.* 17, 691-695, (1999).
Ward, W. W. in Green Fluorescent Protein: Properties, Applications, and Protocols. (ed. M. K. Chalfie, S.) 45-75 (Wiley, New York; 1998).
Ward, W. W. and Cormier, M. J. *J. Biol. Chem.* 254, 781-788, (1979).
Yang, F., Moss, L. G. & Phillips, G. N., Jr. *Nat. Biotechnol* 14, 1246-1251 (1996).
Yarbrough, D.; Wachter, R. M.; Kallio, K.; Matz, M. V. and Remington, S. J.; *Proc. Natl Acad. Sci., USA*, 98:462-67, 2001
Zacharias, D. A., Violin, J. D., Newton, A. C. & Tsien, R. Y., *Science* 296, 913-916 (2002).
Zhang, J.; Campbell, R. E.; Ting, A. Y. and Tsien, R. Y., *Nat. Rev. Mol. Cell Biol.*, 3:906-18, 2002.

What is claimed is:

1. An isolated nucleic acid encoding the amino acid sequence of SEQ ID NO: 20.

2. The isolated nucleic acid of claim 1, wherein the nucleic acid comprises the nucleotide sequence of SEQ ID NO: 19.

3. The isolated nucleic acid of claim 1 which is compatible with mammalian codon usage.

4. The isolated nucleic acid of claim 3, which is compatible with human codon usage.

5. The isolated nucleic acid of claim 1, wherein the encoded polypeptide is a monomer or dimer.

6. The isolated nucleic acid of claim 1, wherein the encoded polypeptide has a chromophore capable of fluorescence with an excitation maximum ranging from 350 to 500 nm and an emission spectrum ranging from about 450 to 600 nm.

7. The isolated nucleic acid of claim 6, wherein the encoded polypeptide has a chromophore capable of fluorescence with an excitation maximum of 493 nm and an emission maximum of 509 nm.

8. The isolated nucleic acid of claim 1, wherein the encoded polypeptide comprises a chromophore comprising the amino acid sequence serine-tyrosine-glycine (SYG).

9. A vector comprising the isolated nucleic acid of claim 1.

10. The vector of claim 9, which is a plasmid.

11. The vector of claim 10, wherein the isolated nucleic acid is cDNA.

12. The vector of claim 9 wherein the isolated nucleic acid is expressed as a tandem fusion to another a nucleic acid encoding protein.

13. An isolated host cell comprising the vector of claim 9.

* * * * *

UNITED STATES PATENT AND TRADEMARK OFFICE
CERTIFICATE OF CORRECTION

| | | |
|---|---|---|
| PATENT NO. | : 7,935,801 B2 | Page 1 of 1 |
| APPLICATION NO. | : 11/948524 | |
| DATED | : May 3, 2011 | |
| INVENTOR(S) | : Robert Earl Campbell and Hui-Wang Ai | |

It is certified that error appears in the above-identified patent and that said Letters Patent is hereby corrected as shown below:

Title Pg, Item (75), Inventors: 2nd Inventor should read: -- Hui-Wang Ai, Edmonton (CA) --.

Signed and Sealed this
Fifth Day of July, 2011

David J. Kappos
*Director of the United States Patent and Trademark Office*